Figure 1A:
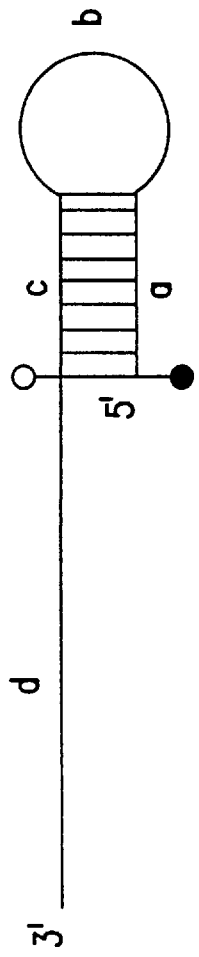

United States Patent [19]
Nazarenko et al.

[11] Patent Number: 5,866,336
[45] Date of Patent: Feb. 2, 1999

[54] NUCLEIC ACID AMPLIFICATION OLIGONUCLEOTIDES WITH MOLECULAR ENERGY TRANSFER LABELS AND METHODS BASED THEREON

[75] Inventors: Irina A. Nazarenko; Satish K. Bhatnagar, both of Gaithersburg; Emily S. Winn-Deen, Potomac; Robert J. Hohman, Gaithersburg, all of Md.

[73] Assignee: Oncor, Inc., Gaithersburg, Md.

[21] Appl. No.: 778,487

[22] Filed: Jan. 3, 1997

Related U.S. Application Data

[63] Continuation-in-part of Ser. No. 683,667, Jul. 16, 1996, abandoned.

[51] Int. Cl.[6] .............................. C12Q 1/68; C12P 17/34; C07H 21/06; C07H 21/00
[52] U.S. Cl. ........................ 435/6; 435/91.2; 536/22.1; 536/24.3; 536/25.32
[58] Field of Search ................... 435/91.2, 6; 536/25.32, 536/22.1, 24.3

[56] References Cited

U.S. PATENT DOCUMENTS

| | | | |
|---|---|---|---|
| 2,998,943 | 9/1961 | Dobbins et al. | 244/14 |
| 3,996,345 | 12/1976 | Ullman et al. | 424/12 |
| 4,160,016 | 7/1979 | Ullman | 424/8 |
| 4,174,384 | 11/1979 | Ullman et al. | 424/8 |
| 4,199,559 | 4/1980 | Ullman et al. | 424/8 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,996,143 | 2/1991 | Heller et al. | 435/6 |
| 5,079,352 | 1/1992 | Gelfand et al. | 536/27 |

(List continued on next page.)

FOREIGN PATENT DOCUMENTS

| | | |
|---|---|---|
| 0 070 685 A2 | 1/1983 | European Pat. Off. . |
| 0 229 943 A2 | 7/1987 | European Pat. Off. . |
| 628 640 A1 | 5/1994 | European Pat. Off. . |
| 0 601 889 A2 | 6/1994 | European Pat. Off. . |
| 0 678 582 A1 | 4/1995 | European Pat. Off. . |
| 4-262799 | 9/1992 | Japan . |
| 4-304900 | 10/1992 | Japan . |
| WO 92/14845 | 9/1992 | WIPO . |
| WO 94/17206 | 8/1994 | WIPO . |
| 95/32306 | 11/1995 | WIPO . |

OTHER PUBLICATIONS

Frommer et al. A genomic sequencing protocol that yields a positive display of 5–methylcytosine residues in individual DNA strands. Pros. Natl. Acad. Sci. U.S.A. vol. 89, pp. 1827–1831, 1992.

Digby, M. et al., 1989, "Human Prostate Specific Antigen (PSA) Gene: Structure and Linkage to the Kallikrein–Like Gene, hGK–1", Nucl. Acids. Res. 17:2137.

(List continued on next page.)

*Primary Examiner*—Kenneth R. Horlick
*Assistant Examiner*—Joyce Tung
*Attorney, Agent, or Firm*—Jonathan M. Cohen; Oncor, Inc.

[57] ABSTRACT

The present invention provides labeled nucleic acid amplification oligonucleotides, which can be linear or hairpin primers or blocking oligonucleotides. The oligonucleotides of the invention are labeled with donor and/or acceptor moieties of molecular energy transfer pairs. The moieties can be fluorophores, such that fluorescent energy emitted by the donor is absorbed by the acceptor. The acceptor may be a fluorophore that fluoresces at a wavelength different from the donor moiety, or it may be a quencher. The oligonucleotides of the invention are configured so that a donor moiety and an acceptor moiety are incorporated into the amplification product. The invention also provides methods and kits for directly detecting amplification products employing the nucleic acid amplification primers. When labeled linear primers are used, treatment with exonuclease or by using specific temperature eliminates the need for separation of unincorporated primers. This "closed-tube" format greatly reduces the possibility of carryover contamination with amplification products, provides for high throughput of samples, and may be totally automated.

38 Claims, 34 Drawing Sheets

U.S. PATENT DOCUMENTS

| | | | |
|---|---|---|---|
| 5,118,801 | 6/1992 | Lizardi et al. | 536/27 |
| 5,119,801 | 6/1992 | Eizenhoefer et al. | 128/24 EL |
| 5,312,728 | 5/1994 | Lizardi et al. | 435/6 |
| 5,348,853 | 9/1994 | Wang et al. | 435/91.2 |
| 5,391,480 | 2/1995 | Davis et al. | 435/6 |
| 5,409,818 | 4/1995 | Davey et al. | 435/91.2 |
| 5,487,972 | 1/1996 | Gelfand et al. | 435/6 |
| 5,532,129 | 7/1996 | Heller | 435/6 |
| 5,538,871 | 7/1996 | Nuovo et al. | 435/6 |
| 5,565,322 | 10/1996 | Heller | 435/6 |
| 5,567,583 | 10/1996 | Wang et al. | 435/6 |
| 5,573,906 | 11/1996 | Bannwarth et al. | 435/6 |
| 5,593,840 | 1/1997 | Bhatnagar et al. | 435/6 |
| 5,607,834 | 3/1997 | Bagwell | 435/6 |
| 5,691,145 | 11/1997 | Pitner et al. | 435/6 |

OTHER PUBLICATIONS

Wilson, R. et al., 1994, "2.2Mb of Contiguous Nucleotide Sequence from Chromosome III of C. elegans", Nature 368:32–38.

Antequera, F. et al., 1990, "High Levels of De Novo Methylation and Altered Chromatin Structure at CpG Islands of Cell Lines", Cell 62:503–514.

Bagasra and Seshamma, 1994, Protocol: In–Situ Amplification and Hybridization, Second Ed., John Wiley and Sons, Somerset, NJ, pp. 1–40.

Bird, A., 1992, "The Essentials of DNA Methylation", Cell 70:5–8.

Cantor, C., 1996, "Lighting Up Hybridization", Nature Biotechnology 14:264.

Cardullo, R. et al., 1988, "Detection of Nucleic Acid Hybridization by Nonradiative Fluoresence Resonance Energy Transfer", Proc. Natl. Acad. Sci. USA 85:8790–8794.

Cimino, G. et al., 1990, "Post–PCR Sterilization: A Method to Control Carryover Contamination for the Polymerase Chain Reaction", Nucleic Acids Res. 19:99–107.

Clegg, R. et al., 1993, "Observing the Helical Geometry of Double–Stranded DNA in Solution by Fluorescence Resonance Energy Transfer", Proc. Natl. Acad. Sci. USA 90:2994–2998.

Clegg, R., 1992, "Fluorescence Resonance Energy Transfer Analysis of the Structure of the Four–Way DNA Junction", Biochemistry 31:4846–4856.

Clementi, M. et al., 1994, "Competitive Polymerase Chain Reaction and Analysis of Viral Activity at the Molecular Level", GATA 11:1–6.

Coghlan, A., 1996, "Brilliant Beacons Colour–Coded Genes", New Scientist, p. 24.

Compton, J., 1991, "Nucleic Acid Sequence–based Amplification" Nature 350:91–92.

Cooper and Hagerman, 1990, "Analysis of Fluorescence Energy Transfer in Duplex and Branched DNA Molecules", Biochemistry 29:9261–9268.

Daubendiek and Kool, 1997, "Generation of Catalytic RNAs by Rolling Transcription of Synthetic DNA Molecules", Nature Biotechnology 15:273–277.

Dexter, D.L., 1953, "A Theory of Sensitized Luminescence in Solids", J. of Chemical Physics 21:836–850.

Förster, V.T., 1949, Z. Naturforschg. 4a:321–327.

Herman, J. et al., 1996, "Methylation–specific PCR: A Novel PCR Assay for Methylation Status of CpG Islands", Proc. Natl. Acad. Sci. USA 93:9821–9826.

Holland, P. et al., 1991, "Detection for Specific Polymerase Chain Reaction Prouct by Utilizing the 5'→3' Exonuclease Activity of *Thermus aquaticus* DNA Polymerase", Proc. Natl. Acad. Sci. USA 88:7276–7280.

Ju, J. et al., 1996, "Energy Transfer Primers: A New Fluorescence Labeling Paradigm for DNA Sequencing and Analysis", Nature Medicine 2:246–249.

Ju, J. et al., 1995, "Fluorescence Energy Transfer Dye–labeled Primers for DNA Sequencing and Analysis", Proc. Natl. Acad. Sci. USA 92:4347–4351.

Landegren, U., 1993, "Molecular Mechanics of Nucleic Acid Sequence Amplification", Technical Focus 9:199–204.

Lee, L. et al., 1993, "Allelic Discrimination by Nick–Translation PCR with Fluorogenic Probes", Nucleic Acids Res. 21:3761–3766.

Li, E. et al., 1993, "Role for DNA Methylation in Genomic Imprinting", Nature 366:362–365.

Li, H. et al., "Eliminating Primers from Completed Polymerase Chain Reactions with Exonuclease VII", Nucleic Acids Res. 19:3139–3141.

Liu, D. et al., 1996, "Rolling Circle DNA Synthesis: Small Circular Oligonucleotides as Efficient Templates for DNA Polymerases", J. Am. Chem. Soc. 118:1587–1594.

Longo, M. et al., 1990, "Use of Uracil DNA Glycosylase to Control Carry–over Contamination in Polymerase Chain Reactions", Gene 93:125–128.

Lyamichev, V. et al., 1993, "Structure–Specific Endonucleolytic Cleavage of Nucleic Acids by Eubacterial DNA Polymerases", Science 260:778–783.

Matayoshi, E., 1990, "Novel Fluorogenic Substrates for Assaying Retroviral Proteases by Resonance Energy Transfer", Science 247:954–958.

Morrison and Stols, 1993, "Sensitive Fluorescence–Based Thermodynamic and Kinetic Measurements of DNA Hybridization in Solution", Biochemistry 32:3095–3104.

Mullis and Faloona, 1987, "Specific Synthesis of DNA in Vitro via a Polymerase–Catalyzed Chain Reaction", Methods in Enzymology 155:335–350.

Newton, C.R. et al., 1989, "Analysis of Any Point Mutation in DNA. The Amplification Refractory Mutation System (ARMS)", Nucleic Acids Research 17:2503–2517.

Nilsson, M. et al., 1994, "Padlock Probes: Circularizing Oligonucleotides for Localized DNA Detection", Science 265:2085–2088.

Okayama, H. et al., 1989, "Rapid, Nonradioactive Detection of Mutations in the Human Genome by Allele–specific Amplification", J. Lab. Clin. Med. 114:105–113.

Orrego, 1990, in Innis et al. (eds), PCR Protocols, A Guide to Methods and Applications, Academic Press, San Diego, CA, pp. 447–454.

Ozaki and McLaughlin, 1992, "The Estimation of Distances Between Specific Backbone–labeled Sites in DNA Using Fluorescence Resonance Energy Transfer", Nucleic Acids Res. 20:5205–5214.

Pfeifer, G. et al., 1989, "Genomic Sequencing and Methylation Analysis by Ligation Mediated PCR", Science 246:810–813.

Sarin, P. et al., 1988, "Inhibition of Acquired Immunodeficiency Syndrom Virus by Oligodeoxynucleoside Methylphosphonates", Proc. Natl. Acad. Sci. USA 85:7448–7451.

Schutzbank and Smith, 1995, "Detection of Human Immunodeficiency Virus Type I Proviral DNA by PCR Using an Electrochemiluminescence–Tagged Probe", J. of Clinical Microbiology 33:2036–2041.

Selvin, P., 1995, "Fluorescence Resonance Energy Transfer", Methods in Enzymology 246:300–334.

Siebert and Larrick, 1992, "Competitive PCR", Nature 359:557–558.

Sommer, S. et al., 1992, "PCR Amplification of Specific Alleles (PASA) is a General Method for Rapidly Detecting Known Single–Base Changes", BioTechniques 12:82–87.

Stein, C.A. et al., 1988, "Physicochemical Properties of Phosphorothioate Oligodeoxynucleotides", Nucleic Acids Research 16:3209–3221.

Steinberg, I., 1971, "Long–Range Nonradiative Transfer of Electronic Excitation Energy in Proteins and Polypeptides", Ann. Rev. Biochem. 40:83–114.

Stryer, L., 1978, "Fluorescence Energy Transfer as a Spectroscopic Ruler", Ann. Rev. Biochem. 47:819–846.

Tyagi and Kramer, 1996, "Molecular Beacons: Probes that Fluoresce upon Hybridization", Nature Biotechnology 14:303–308.

Varani, G., 1995, "Exceptionally Stable Nucleic Acid Hairpins", Annu. Rev. Biophys. Biomol. Struct. 24:379–404.

Walder, R. et al., 1993, "Use of PCR Primers Containing a 3'–terminal Ribose Residue to Prevent Cross–Contamination of Amplified Sequences", Nucleic Acids Res. 21:4339–4343.

Walker, T., Handout from Gene Detection and Quantitation Meeting, San Diego, CA, Jun. 9–11, 1997.

Walker, G.T. et al., 1996, "Strand Displacement Amplification (SDA) and Transient–State Fluorescence Polarization Detection of *Mycobacterium Tuberculosis* DNA" Clinical Chemistry 42:9–13.

Walker and Linn, 1996, "Detection of *Mycobacterium Tuberculosis* DNA with Thermophilic Strand Displacement Amplification and Fluorescence Polarization", Clinical Chemistry 42:1604–1608.

Walker, G.T. et al., 1992, "Isothermal in Vitro Amplification of DNA by a Restriction Enzyme/DNA Polymerase System", Proc. Natl. Acad. Sci. USA 89:392–396.

Walker, G. et al., 1992, Strand Displacement Amplification—An Isothermal, In Vitro DNA Amplification Technique, Nucleic Acids Res. 20:1691–1696.

Wang, G. et al., 1990, "Design and Synthesis of New Fluorogenic HIV Protease Substrates Based on Resonance Energy Transfer", Tetrahedron Letters 31:6493–6496.

Wang, Y. et al., 1995, "Rapid Sizing of Short Tandem Repeat Alleles Using Capillary Array Electrophoresis and Energy–Transfer Fluorescent Primers", Anal. Chem. 67:1197–1203.

Wu and Wang, "A Convenient and Versatile Process for Quantitative PCR: The Amplisensor Assay", Research Communication, Biotronics Corp., Lowell, MA, pp. 1–2.

5' CTGGGGCAGCATTGAACCAGAGGAGTTCTT...CATGTGCCTGCCCGAAAGGCCTTCCCTGTACACCAAGGTG 3'
                                                   ACGGGCTTTCCGGAAGGGACATGTGG 5'
                                                              PSA-1

PSA-P                              PSA-B
       5' GCAGCATTGAACCAGAGGAGTT 3'    5' CCGAAAGGCCTTCCCTGTACACCAAAA 3'

3' GACCCCGTGTAACTTGGTCTCCTCAAGAA...GTACACGGACGGGCTTTCCGGAAGGGACATGTGGTTCCAC 5'

FIG.12

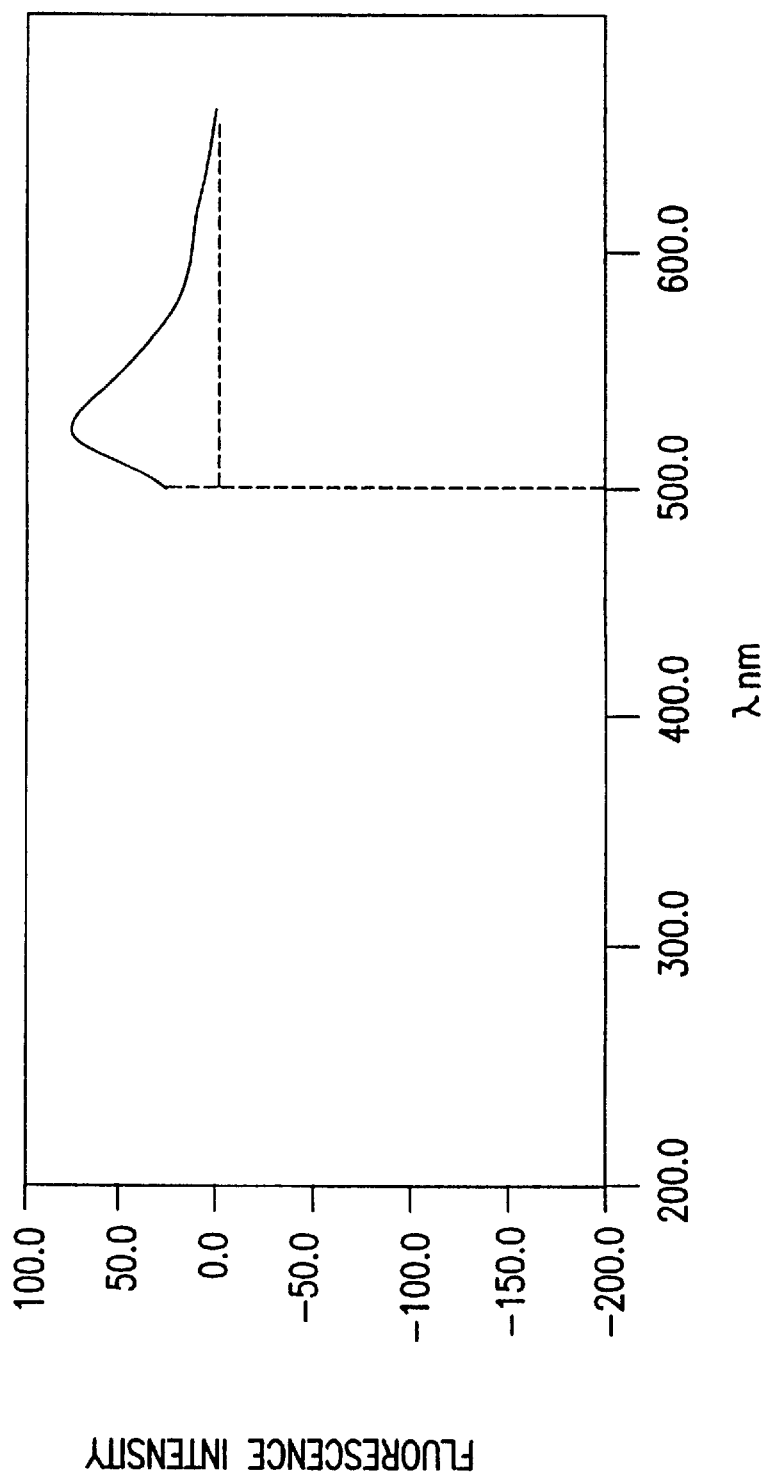

| | 3' SINGLE STRANDED SEQUENCE (nucl) | STEM (bp) | LOOP (bp) | FLUORESCENCE rel (%) |
|---|---|---|---|---|

| | 3' SINGLE STRANDED SEQUENCE (nucl) | STEM (bp) | LOOP (bp) | FLUORESCENCE rel (%) |
|---|---|---|---|---|

| | 3' SINGLE STRANDED SEQUENCE (nucl) | STEM (bp) | LOOP (bp) | FLUORESCENCE rel (%) |
|---|---|---|---|---|

Uup (UPSTREAM)

5' – TGGTTATTAGAGGGTGGGGTGGATTGT –3'    (SEQ ID NO: 19)

Ud (DOWNSTREAM)

```
   T A         DAB
 A     AGTAGCTTACCCAACCCCAAACCACAACCATAA –3'    (SEQ ID NO: 20)
 G     TCATCGA
   T C         FAM
```

Mup (UPSTREAM)

5' – TTATTAGAGGGTGGGGCGGATCGC    (SEQ ID NO: 21)

Md (DOWNSTREAM)

```
   T A         DAB
 A     AGTAGCTGACCCCGAACCGCGACCGTAA –3'    (SEQ ID NO: 22)
 G     TCATCGA
   T C         FAM
```

Wup (UPSTREAM)

5' – CAGAGGGTGGGGCGGACCGC    (SEQ ID NO: 23)

Wd (DOWNSTREAM)

```
   T A         DAB
 A     AGTAGCTCCCGGGCCGCGGCCGTGG –3'    (SEQ ID NO: 24)
 G     TCATCGA
   T C         FAM
```

FIG. 26

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Other
        ( B ) LOCATION: 1
        ( D ) OTHER INFORMATION: 5- carboxyfluorescein (FAM moiety) attached to 1st nucleotide
( A ) NAME/KEY: Other
( B ) LOCATION: 22
( D ) OTHER INFORMATION: DABCYL attached to 22nd nucleotide ( x i ) SEQUENCE DESCRIPTION: SEQ ID NO:1:

GGCTACGAAC CAGGTAAGCC GTA                23

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

GCCGGTGACC AAGTTCAT                18

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

CTGGGGCAGC ATTGAACCAG AGGAGTTCTT                30

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

CATGTGCCTG CCCGAAAGGC CTTCCCTGTA CACCAAGGTG                40

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: PSA-I
        ( B ) LOCATION: 1...26

( x i ) SEQUENCE DESCRIPTION: SEQ ID NO:5:

GGTGTACAGG GAAGGCCTTT CGGGCA                26

( 2 ) INFORMATION FOR SEQ ID NO:6:

( i ) SEQUENCE CHARACTERISTICS:
        ( A ) LENGTH: 22 base pairs
        ( B ) TYPE: nucleic acid (C) STRANDEDNESS: single
(D) TOPOLOGY: linear (i i) MOLECULE TYPE: DNA (i x) FEATURE:
(A) NAME/KEY: PSA-P
(B) LOCATION: 1...22

(x i) SEQUENCE DESCRIPTION: SEQ ID NO:6:

GCAGCATTGA ACCAGAGGAG TT 22

(2) INFORMATION FOR SEQ ID NO:7:

(i) SEQUENCE CHARACTERISTICS:
(A) LENGTH: 27 base pairs
(B) TYPE: nucleic acid
(C) STRANDEDNESS: single
(D) TOPOLOGY: linear (i i) MOLECULE TYPE: DNA (i x) FEATURE:
(A) NAME/KEY: PSA-B
(B) LOCATION: 1...27

(x i) SEQUENCE DESCRIPTION: SEQ ID NO:7:

CCGAAAGGCC TTCCCTGTAC ACCAAAA 27

(2) INFORMATION FOR SEQ ID NO:8:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:8:

AAGAACTCCT CTGGTTCAAT GCTGCCCCAG 30

(2) INFORMATION FOR SEQ ID NO:9:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:9:

CACCTTGGTG TACAGGGAAG GCCTTTCGGG CAGGCACATG 40

(2) INFORMATION FOR SEQ ID NO:10:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: DNA (i x) FEATURE:
(A) NAME/KEY: Other
(B) LOCATION: 1
(D) OTHER INFORMATION: 5- carboxyfluorescein (FAM
moiety) attached to 1st nucleotide
(A) NAME/KEY: Other
(B) LOCATION: 20

(D) OTHER INFORMATION: DABCYL attached to 20th
              nucleotide (xi) SEQUENCE DESCRIPTION: SEQ ID NO:10:

ACCTTCTACC CTCAGAAGGT GACCAAGTTC AT 32

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CCCTCAGAAG GTGACCAAGT TCAT 24

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGTGTACAGG GAAGGCCTTT CGGGAC 26

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1
        (D) OTHER INFORMATION: 5- carboxyfluorescein (FAM
              moiety) attached to 1st nucleotide
        (A) NAME/KEY: Other
        (B) LOCATION: 20
        (D) OTHER INFORMATION: DABCYL attached to 20th
              nucleotide (xi) SEQUENCE DESCRIPTION: SEQ ID NO:13:

ACCTTCTACC CTCAGAAGGT GACCAAGTTC AT 32

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1
        (D) OTHER INFORMATION: 5- carboxyfluorescein (FAM
              moiety) attached to 1st nucleotide
        (A) NAME/KEY: Other
        (B) LOCATION: 24

(D) OTHER INFORMATION: DABCYL attached to 24th nucleotide (xi) SEQUENCE DESCRIPTION: SEQ ID NO:14:

ACCTTCTGTT CACCCTCAGA AGGTGACCAA GTTCAT    36

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1
        (D) OTHER INFORMATION: 5- carboxyfluorescein (FAM moiety) attached to 1st nucleotide
        (A) NAME/KEY: Other
        (B) LOCATION: 24
        (D) OTHER INFORMATION: DABCYL attached to 24th nucleotide (xi) SEQUENCE DESCRIPTION: SEQ ID NO:15:

ACCTTCGATT CACCCTCAGA AGGTGACCAA GTTCAT    36

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1
        (D) OTHER INFORMATION: 5- carboxyfluorescein (FAM moiety) attached to 1st nucleotide
        (A) NAME/KEY: Other
        (B) LOCATION: 22
        (D) OTHER INFORMATION: DABCYL attached to 22nd nucleotide (xi) SEQUENCE DESCRIPTION: SEQ ID NO:16:

ACCTTCTGTA CCCTCAGAAG GTGACCAAGT TCAT    34

(2) INFORMATION FOR SEQ ID NO:17:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1
        (D) OTHER INFORMATION: 5- carboxyfluorescein (FAM moiety) attached to 1st nucleotide
        (A) NAME/KEY: Other
        (B) LOCATION: 22
        (D) OTHER INFORMATION: DABCYL attached to 22nd nucleotide (xi) SEQUENCE DESCRIPTION: SEQ ID NO:17:

ACCTTCTATA CCCTCAGAAG GTGACCAAGT TCAT    34

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Other
        ( B ) LOCATION: 1
        ( D ) OTHER INFORMATION: 5- carboxyfluorescein (FAM moiety) attached to 1st nucleotide
        ( A ) NAME/KEY: Other
        ( B ) LOCATION: 20
        ( D ) OTHER INFORMATION: DABCYL attached to 20th nucleotide ( x i ) SEQUENCE DESCRIPTION: SEQ ID NO:18:

CACCTTCACC CTCAGAAGGT GACCAAGTTC AT    32

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Uup (upstream)
        ( B ) LOCATION: 1...27

( x i ) SEQUENCE DESCRIPTION: SEQ ID NO:19:

TGGTTATTAG AGGGTGGGGT GGATTGT    27

( 2 ) INFORMATION FOR SEQ ID NO:20:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Ud (downstream)
        ( B ) LOCATION: 1...46
        ( A ) NAME/KEY: Other
        ( B ) LOCATION: 1
        ( D ) OTHER INFORMATION: 5- carboxyfluorescein (FAM moiety) attached to 1st nucleotide
        ( A ) NAME/KEY: Other
        ( B ) LOCATION: 20
        ( D ) OTHER INFORMATION: DABCYL attached to 20th nucleotide ( x i ) SEQUENCE DESCRIPTION: SEQ ID NO:20:

AGCTACTCTG ATAAGTAGCT TACCCAACCC CAAACCACAA CCATAA    46

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single ( D ) TOPOLOGY: linear ( i i ) MOLECULE TYPE: DNA ( i x ) FEATURE:
  ( A ) NAME/KEY: Mup (upstream)
  ( B ) LOCATION: 1...24

( x i ) SEQUENCE DESCRIPTION: SEQ ID NO:21:

TTATTAGAGG GTGGGGCGGA TCGC      24

( 2 ) INFORMATION FOR SEQ ID NO:22:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Md (downstream)
  ( B ) LOCATION: 1...41
  ( A ) NAME/KEY: Other
  ( B ) LOCATION: 1
  ( D ) OTHER INFORMATION: 5- carboxyfluorescein (FAM
    moiety) attached to 1st nucleotide
  ( A ) NAME/KEY: Other
  ( B ) LOCATION: 20
  ( D ) OTHER INFORMATION: DABCYL attached to 20th
    nucleotide ( x i ) SEQUENCE DESCRIPTION: SEQ ID NO:22:

AGCTACTCTG ATAAGTAGCT GACCCCGAAC CGCGACCGTA A      41

( 2 ) INFORMATION FOR SEQ ID NO:23:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Wup (upstream)
  ( B ) LOCATION: 1...20

( x i ) SEQUENCE DESCRIPTION: SEQ ID NO:23:

CAGAGGGTGG GGCGGACCGC      20

( 2 ) INFORMATION FOR SEQ ID NO:24:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: DNA ( i x ) FEATURE:
  ( A ) NAME/KEY: Wd (downstream)
  ( B ) LOCATION: 1...38
  ( A ) NAME/KEY: Other
  ( B ) LOCATION: 1
  ( D ) OTHER INFORMATION: 5- carboxyfluorescein (FAM
    moiety) attached to 1st nucleotide
  ( A ) NAME/KEY: Other
  ( B ) LOCATION: 20
  ( D ) OTHER INFORMATION: DABCYL attached to 20th
    nucleotide (x i) SEQUENCE DESCRIPTION: SEQ ID NO:24:

AGCTACTCTG ATAAGTAGCT CCCGGGCCGC GGCCGTGG           38

(2) INFORMATION FOR SEQ ID NO:25:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (i i) MOLECULE TYPE: DNA (i x) FEATURE:
       (A) NAME/KEY: OTHER
       (B) LOCATION: 1
       (C) OTHER INFORMATION: 5- carboxyfluorescein (FAM
             moiety) attached to 1st nucleotide
       (A) NAME/KEY: OTHER
       (B) LOCATION: 20
       (C) OTHER INFORMATION: DABCYL attached to 20th
             nucleotide (x i) SEQUENCE DESCRIPTION: SEQ ID NO:25:

ACCTTCTACC CTCAGAAGGT GACCAA           26

NUCLEIC ACID AMPLIFICATION OLIGONUCLEOTIDES WITH MOLECULAR ENERGY TRANSFER LABELS AND METHODS BASED THEREON

This application is a continuation-in-part of application Ser. No. 08/683,667 filed Jul. 16, 1996, now abandoned, which is incorporated by reference herein in its entirety.

TABLE OF CONTENTS
1. INTRODUCTION
2. BACKGROUND OF THE INVENTION
   2.1. FLUORESCENCE RESONANCE ENERGY TRANSFER (FRET)
   2.2. METHODS OF MONITORING NUCLEIC ACID AMPLIFICATION
3. SUMMARY OF THE INVENTION
   3.1. DEFINITIONS
4. DESCRIPTION OF THE FIGURES
5. DETAILED DESCRIPTION OF THE INVENTION
   5.1. OLIGONUCLECOTIDES
      5.1.1. HAIRPIN PRIMERS
         5.1.1.1. UNIVERSAL HAIRPIN PRIMERS
      5.1.2. LINEAR OLIGONUCLEOTIDES
   5.2. METHODS FOR DETECTION OF AMPLIFICATION PRODUCTS USING HAIRPIN PRIMERS
      5.2.1. METHODS OF USE OF HAIRPIN PRIMERS IN POLYMERASE CHAIN REACTION (PCR)
         5.2.1.1. METHODS OF USE OF HAIRPIN PRIMERS IN ALLELE-SPECIFIC PCR (ASP)
      5.2.2. METHODS OF USE OF HAIRPIN PRIMERS IN TRIAMPLIFICATION
         5.2.2.1. GENERAL STEPS IN TRIAMPLIFICATION REACTIONS
         5.2.2.2. USE OF HAIRPIN PRIMERS IN TRIAMPLIFICATION REACTIONS
      5.2.3. METHODS OF USE OF HAIRPIN PRIMERS IN NUCLEIC ACID SEQUENCE-BASED AMPLIFICATION (NASBA)
      5.2.4. METHODS OF USE OF HAIRPIN PRIMERS IN STRAND DISPLACEMENT AMPLIFICATION (SDA)
   5.3. METHODS OF DETECTION OF AMPLIFICATION PRODUCTS USING 3'-5' EXONUCLEASE AND/OR ELEVATED TEMPERATURE
      5.3.1. USE OF 3'-5' EXONUCLEASE IN AMPLIFICATION REACTIONS
      5.3.2. USE OF TEMPERATURE ELEVATION IN AMPLIFICATION REACTIONS
   5.4. METHODS FOR DETECTION OF AMPLIFICATION PRODUCTS USING LINEAR PRIMERS
      5.4.1. METHODS OF USE OF LINEAR PRIMERS IN POLYMERASE CHAIN REACTION (PCR)
         5.4.1.1. METHODS OF USE OF LINEAR PRIMERS IN ALLELE-SPECIFIC PCR (ASP)
      5.4.2. METHODS OF USE OF LINEAR OLIGONUCLEOTIDES IN TRIAMPLIFICATION
   5.5. METHODS OF USE OF HAIRPIN OR LINEAR PRIMERS IN MULTIPLEX ASSAYS
   5.6. ASSAYING THE METHYLATION STATUS OF DNA USING AMPLIFICATION REACTIONS OF THE INVENTION
   5.7. KITS FOR THE AMPLIFICATION AND DETECTION OF SELECTED TARGET DNA SEQUENCES
6. EXAMPLES: GENERAL EXPERIMENTAL METHODS
   6.1. OLIGONUCLEOTIDE SEQUENCES: SYNTHESIS AND MODIFICATION
   6.2. AMPLIFICATION OF PROSTATE SPECIFIC ANTIGEN (PSA) TARGET DNA
   6.3. 3'-5' EXONUCLEASE TREATMENT
   6.4. ENERGY TRANSFER MEASUREMENTS
7. EXAMPLE 1: DNA POLYMERASE COPIES A DNA TEMPLATE WITH RHODAMINE MODIFICATION
8. EXAMPLE 2: MODIFICATION OF A REVERSE PRIMER DOES NOT AFFECT THE REACTION CATALYZED BY DNA LIGASE
9. EXAMPLE 3: EXONUCLEASE CAN REMOVE A NUCLEOTIDE RESIDUE LABELED WITH RHODAMINE
10. EXAMPLE 4: DETECTION OF AMPLIFICATION PRODUCT BY ENERGY TRANSFER AFTER NUCLEASE TREATMENT
11. EXAMPLE 5: DETECTION OF AMPLIFICATION PRODUCT BASED ON DIFFERENT THERMOSTABILITY OF AMPLIFIED PRODUCT AND BLOCKER/REVERSE PRIMER COMPLEX
12. EXAMPLE 6: CLOSED-TUBE FORMAT USING HAIRPIN PRIMERS FOR AMPLIFICATION AND DETECTION OF DNA BASED ON ENERGY TRANSFER
   12.1. SUMMARY
   12.2. INTRODUCTION
   12.3. MATERIALS AND METHODS
   12.4. RESULTS
   12.5. DISCUSSION
13. EXAMPLE 7: ASSAY FOR THE METHYLATION STATUS OF CpG ISLANDS USING PCR WITH HAIRPIN PRIMERS
   13.1. MATERIALS AND METHODS
   13.2. RESULTS
   13.3. CONCLUSION

1. INTRODUCTION

The present invention relates to oligonucleotides for amplification of nucleic acids that are detectably labeled with molecular energy transfer (MET) labels. It also relates to methods for detecting the products of nucleic acid amplification using these oligonucleotides. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

2. BACKGROUND OF THE INVENTION

2.1. FLOURESCENCE RESONANCE ENERGY TRANSFER (FRET)

Molecular energy transfer (MET) is a process by which energy is passed non-radiatively between a donor molecule and an acceptor molecule. Fluorescence resonance energy transfer (FRET) is a form of MET. FRET arises from the properties of certain chemical compounds; when excited by exposure to particular wavelengths of light, they emit light (i.e., they fluoresce) at a different wavelength. Such compounds are termed fluorophores. In FRET, energy is passed non-radiatively over a long distance (10–100 Å) between a donor molecule, which is a fluorophore, and an acceptor molecule. The donor absorbs a photon and transfers this energy nonradiatively to the acceptor (Förster, 1949, Z. Naturforsch., A4: 321–327; Clegg, 1992, Methods Enzymol., 211: 353–388).

When two fluorophores whose excitation and emission spectra overlap are in close proximity, excitation of one fluorophore will cause it to emit light at wavelengths that are absorbed by and that stimulate the second fluorophore, causing it in turn to fluoresce. In other words, the excited-state energy of the first (donor) fluorophore is transferred by a resonance induced dipole—dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quencher.

Pairs of molecules that can engage in fluorescence resonance energy transfer (FRET) are termed FRET pairs. In order for energy transfer to occur, the donor and acceptor molecules must typically be in close proximity (up to 70 to 100 Å)(Clegg, 1992, Methods Enzymol., 211: 353–388; Selvin, 1995, Methods Enzymol., 246: 300–334). The efficiency of energy transfer falls off rapidly with the distance between the donor and acceptor molecules. According to Förster (1949, Z. Naturforsch., A4:321–327), the efficiency of energy transfer is proportional to $D \times 10^{-6}$, where D is the distance between the donor and acceptor. Effectively, this means that FRET can most efficiently occur up to distances of about 70 Å.

Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

In the 1970's, FRET labels were incorporated into immunofluorescent assays used to detect specific antigens (Ullman et al. U.S. Pat. Nos. 2,998,943; 3,996,345; 4,160,016; 4,174,384; and 4,199,559). Later, in the early 1980's, several patents were received by Heller and coworkers concerning the application of energy transfer for polynucleotide hybridization (U.S. Pat. Nos. 4,996,143, 5,532,129, and 5,565,322). In European Patent Application 82303699.1 (publication number EP 0 070 685 A2 dated Jan. 26, 1983), "Homogeneous nucleic acid hybridization diagnostics by non-radioactive energy transfer," the inventors claim that they can detect a unique single stranded polynucleotide sequence with two oligonucleotides: one containing the donor fluorophore, the other, an acceptor. When both oligonucleotides hybridize to adjacent fragments of analyzed DNA at a certain distance, energy transfer can be detected.

In European Patent Application 86116652.8 (publication number EP 0 229 943 A2 dated Jul. 29, 1987; "EP '943"), entitled "Fluorescent Stokes shift probes for polynucleotide hybridization assays," Heller et al. propose the same schema, but with specified distances between donor and acceptor for maximum FRET. They also disclose that the donor and acceptor labels can be located on the same probe (see, e.g., EP '943: Claim 2 and FIG. 1).

A similar application of energy transfer was disclosed by Cardullo et al. in a method of detecting nucleic acid hybridization (1988, Proc. Natl. Acad. Sci. USA, 85: 8790–8794). Fluorescein (donor) and rhodamine (acceptor) are attached to 5' ends of complementary oligodeoxynucleotides. Upon hybridization, FRET may be detected. In other experiments, FRET occurred after hybridization of two fluorophore-labeled oligonucleotides to a longer unlabeled DNA. This system is the subject of U.S. patent application Ser. No. 661,071, and PCT Application PCT/US92/1591, Publication No. WO 92/14845 dated Sep. 3, 1992 ("PCT '845," entitled "Diagnosing cystic fibrosis and other genetic diseases using fluorescence resonance energy transfer"). PCT '845 discloses a method for detection of abnormalities in human chromosomal DNA associated with cystic fibrosis by hybridization. The FRET signal used in this method is generated in a manner similar to that disclosed by Heller et al. (see PCT '845 FIG. 1). Other publications have disclosed the use of energy transfer in a method for the estimation of distances between specific sites in DNA (Ozaki and McLaughlin, 1992, Nucl. Acids Res., 20: 5205–5214), in a method for the analysis of structure of four way DNA junction (Clegg et al. 1992, Biochem., 31: 4846–4856), and in a method for observing the helical geometry of DNA (Clegg et al., 1993, Proc. Natl. Acad. Sci. USA, 90: 2994–2998).

2.2. METHODS OF MONITORING NUCLEIC ACID AMPLIFICATION

Prior to the present invention, application of energy transfer to the direct detection of genetic amplification products had not been attempted. In prior art methods of monitoring amplification reactions using energy transfer, a label is not incorporated into the amplification product. As a result, these methods have relied on indirect measurement of the amplification reaction.

Commonly used methods for detecting nucleic acid amplification products require that the amplified product be separated from unreacted primers. This is commonly achieved either through the use of gel electrophoresis, which separates the amplification product from the primers on the basis of a size differential, or through the immobilization of the product, allowing washing away of free primer. However, three methods for monitoring the amplification process without prior separation of primer have been described. All of them are based on FRET, and none of them detect the amplified product directly. Instead, all three methods detect some event related to amplification. For that reason, they are accompanied by problems of high background, and are not quantitative, as discussed below.

One method, described in Wang et al. (U.S. Pat. No. 5,348,853; Wang et al., 1995, Anal. Chem., 67: 1197–1203), uses an energy transfer system in which energy transfer occurs between two fluorophores on the probe. In this method, detection of the amplified molecule takes place in the amplification reaction vessel, without the need for a separation step. This method results in higher sensitivity than methods that rely on monolabeled primers.

The Wang et al. method uses an "energy-sink" oligonucleotide complementary to the reverse primer. The "energy-sink" and reverse-primer oligonucleotides have donor and acceptor labels, respectively. Prior to amplification, the labeled oligonucleotides form a primer duplex in which energy transfer occurs freely. Then, asymmetric PCR is carried out to its late-log phase before one of the target strands is significantly overproduced.

A primer duplex complementary to the overproduced target strand is added to prime a semi-nested reaction in concert with the excess primer. As the semi-nested amplification proceeds, the primer duplex starts to dissociate as the target sequence is duplicated. As a result, the fluorophores configured for energy transfer are disengaged from each other, causing the energy transfer process preestablished in all of the primer duplexes to be disrupted for those primers involved in the amplification process. The measured fluorescence intensity is proportional to the amount of primer duplex left at the end of each amplification cycle. The decrease in the fluorescence intensity correlates proportionately to the initial target dosage and the extent of amplification.

This method, however, does not detect the amplified product, but instead detects the dissociation of primer from the "energy-sink" oligonucleotide. Thus, this method is dependent on detection of a decrease in emissions; a significant portion of labeled primer must be utilized in order to achieve a reliable difference between the signals before and after the reaction. This problem was apparently noted by Wang et al., who attempted to compensate by adding a preliminary amplification step (asymmetric PCR) that is supposed to increase the initial target concentration and consequently the usage of labeled primer, but also complicates the process.

A second method for detection of amplification product without prior separation of primer and product is the 5' nuclease PCR assay (also referred to as the TaqMan® assay) (Holland et al., 1991, Proc. Natl. Acad. Sci. USA, 88: 7276–7280; Lee et al., 1993, Nucleic Acids Res., 21: 3761–3766). This assay detects the accumulation of a specific PCR product by hybridization and cleavage of a doubly labeled fluorogenic probe (the "TaqMan" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

In the TaqMan assay, the donor and quencher are preferably located on the 3' and 5'-ends of the probe, because the requirement that 5'-3 hydrolysis be performed between the fluorophore and quencher may be met only when these two moieties are not too close to each other (Lyamichev et al., 1993, Science, 260:778–783). However, this requirement is a serious drawback of the assay, since the efficiency of energy transfer decreases with the inverse sixth power of the distance between the reporter and quencher. In other words, the TaqMan assay does not permit the quencher to be close enough to the reporter to achieve the most efficient quenching. As a consequence, the background emissions from unhybridized probe can be quite high.

Furthermore, the TaqMan assay does not measure the amplification product directly, because the amplification primers are not labeled. This assay measures an event related to amplification: the hydrolysis of the probe that hybridizes to the target DNA between the primer sequences. As a result, this assay method is accompanied by significant problems. First, hybridization will never be quantitative unless the labeled oligonucleotide is present in great excess. However, this results in high background (because the quenching is never quantitative). In addition, a great excess of oligonucleotide hybridized to the middle of the target DNA will decrease PCR efficiency. Furthermore, not all of the oligonucleotides hybridized to the DNA will be the subject of 5'-3' exonuclease hydrolysis: some will be displaced without hydrolysis, resulting in a loss of signal.

Another method of detecting amplification products that relies on the use of energy transfer is the "beacon probe" method described by Tyagi and Kramer (1996, Nature Biotech., 14:303–309) which is also the subject of U.S. Pat. Nos. 5,119,801 and 5,312,728 to Lizardi et al. This method employs oligonucleotide hybridization probes that can form hairpin structures. On one end of the hybridization probe (either the 5' or 3' end) there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, 1996, Nature Biotechnol., 14: 303–306. As a result, the amount of fluorescence will increase as the amount of PCR product increases, and thus may be used as a measure of the progress of the PCR.

However, since this method is based on hybridization of the probe to template between the primer sequences, it has a number of problems associated with it, some of which are similar to those described above in connection with the TaqMan method. First, it is unlikely that the beacon probes will hybridize quantitatively to one strand of double-stranded PCR product, especially when the amplification product is much longer than the beacon probe. Even those probes that are hybridized could be displaced by the second DNA strand over a short period of time; as a result, this method cannot be quantitative.

Efforts to increase the hybridization efficiency by increasing the concentration of beacon probe will result in decreased amplification efficiency, since the necessity for DNA polymerase to displace hybridized beacons during the reaction will slow down the rate of polymerization. An excess of probe will also increase the background. In addition, the ratio between the amplification product and the beacon probes will change as amplification proceeds, and so will change the efficiency of hybridization. Thus the detection of the amplified product may not be quantitative.

Therefore, in view of the deficiencies in prior art methods of detecting amplification products, it is clear that there exists in the art a need for an improved method of detecting amplification products rapidly, sensitively, reliably and quantitatively. The present invention solves this problem by providing nucleic acid amplification primers that are detectably labeled with energy-transfer labels. It also solves this problem by providing methods for detecting amplification products that are adaptable to many methods for amplification of nucleic acid sequences and that greatly decrease the possibility of carryover contamination with amplification products.

Citation of references herein shall not be construed as an admission that such references are prior art to the present invention.

3. SUMMARY OF THE INVENTION

The present invention relates to oligonucleotides for amplification of nucleic acids that are detectably labeled with molecular energy transfer (MET) labels. One or more oligonucleotides of the invention containing a donor and/or acceptor moiety of a MET pair are incorporated into the amplified product of an amplification reaction, such that the amplified product contains both a donor and acceptor moiety of a MET pair. When the amplified product is double-stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The invention also relates to methods for detecting the products of nucleic acid amplification using these labeled oligonucleotides of the invention. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

The nucleic acid amplification oligonucleotides of the invention utilize the principle of molecular energy transfer (MET) between a donor moiety and an acceptor moiety. In a preferred embodiment, the MET is fluorescence resonance energy transfer (FRET), in which the oligonucleotides are labeled with donor and acceptor moieties, wherein the donor moiety is a fluorophore and the acceptor moiety may be a fluorophore, such that fluorescent energy emitted by the donor moiety is absorbed by the acceptor moiety. In one embodiment of the present invention, the acceptor moiety is a fluorophore that releases the energy absorbed from the donor at a different wavelength; the emissions of the acceptor may then be measured to assess the progress of the amplification reaction. In another embodiment, the acceptor moiety is a quencher.

In a preferred embodiment, the amplification primer is a hairpin primer that contains both donor and acceptor moieties, and is configured such that the acceptor moiety quenches the fluorescence of the donor. When the primer as incorporated into the amplification product its configuration changes, quenching is eliminated, and the fluorescence of the donor moiety may be detected.

In one embodiment, the present invention provides nucleic acid amplification primers that form a hairpin structure in which MET will occur when the primer is not incorporated into the amplification product. In a preferred embodiment, a primer forms a hairpin structure in which the energy of a donor fluorophore is quenched by a non-fluorescing fluorophore when the primer is not incorporated into the amplification product.

In another embodiment, the present invention provides oligonucleotides that are linear (non-duplex) and that are separately labeled with donor and acceptor moieties, such that MET will occur when the oligonucleotides are incorporated into the amplification product. For example, the blocking oligonucleotide and the reverse primer complementary to the blocking oligonucleotide can be so labeled in a triamplification reaction.

In yet another embodiment, the donor moiety and acceptor moiety are on a single, linear oligonucleotide used in an amplification reaction.

The present invention also provides a method of directly detecting amplification products. This improved technique meets two major requirements. First, it permits detection of the amplification product without prior separation of unincorporated oligonucleotides. Second, it allows detection of the amplification product directly, by incorporating the labeled oligonucleotide into the product.

The present invention provides a method of directly detecting amplification products through the incorporation of labeled oligonucleotide(s) (e.g., primers, blocking oligonucleotides) wherein instead of separating unincorporated oligonucleotides from amplification product, as in prior art approaches, signal from the remaining free oligonucleotide(s) is eliminated in one (or more) of the following ways:

a) by treatment with a 3'-5' exonuclease;

b) by heating the amplification product to a temperature such that the primer-oligonucleotide duplex dissociates and, as a result, will not generate any signal; or c) by using a primer labeled with both donor and acceptor moieties and that can form a hairpin structure, in which the energy transfer from donor to acceptor will occur only when the primer is not incorporated into the amplification product.

In a further embodiment, the present invention provides a method for the direct detection of amplification products in which the detection may be performed without opening the reaction tube. This embodiment, the "closed-tube" format, reduces greatly the possibility of carryover contamination with amplification products that has slowed the acceptance of PCR in many applications. The closed-tube method also provides for high throughput of samples and may be totally automated. The present invention also relates to kits for the detection or measurement of nucleic acid amplification products. Such kits may be diagnostic kits where the presence of the nucleic acid being amplified is correlated with the presence or absence of a disease or disorder.

3.1. DEFINITIONS

As used herein, the following terms shall have the abbreviations indicated.

ASP, allele-specific polymerase chain reaction bp, base pairs

DAB or DABCYL, 4-(4'-dimethylaminophenylazo) benzoic acid

EDANS, 5-(2'-aminoethyl) aminonapthalene-1-sulfonic acid

FAM or Flu, 5-carboxyfluorescein

FRET, fluorescence resonance energy transfer

JOE, 2'7'-dimethoxy-4'5'-dichloro-6-carboxyfluorescein

HPLC, high-performance liquid chromatography

MET, molecular energy transfer

NASBA, nucleic acid sequence-based amplification

PSA, prostate specific antigen

Rhod, rhodamine

ROX, 6-carboxy-X-rhodamine

R6G, 6-carboxyrhodamine

SDA, strand displacement amplification

TAMRA, N,N,N',N'-tetramethyl-6-carboxyrhodamine

4. DESCRIPTION OF THE FIGURES

Figure 1B:
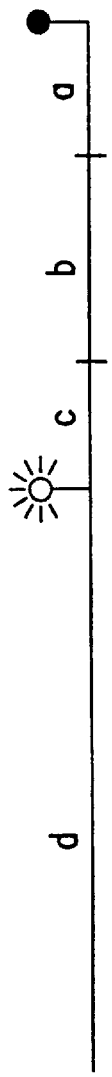

The present invention may be understood more fully by reference to the following detailed description of the invention, examples of specific embodiments of the invention and the appended figures described below:

FIGS. 1A–B illustrate schematically the structure of the hairpin primers of the invention in the (A) closed (quenched) and (B) open (emitting signal) states. ○, donor fluorophore; ●, quencher fluorophore.

Figure 2:
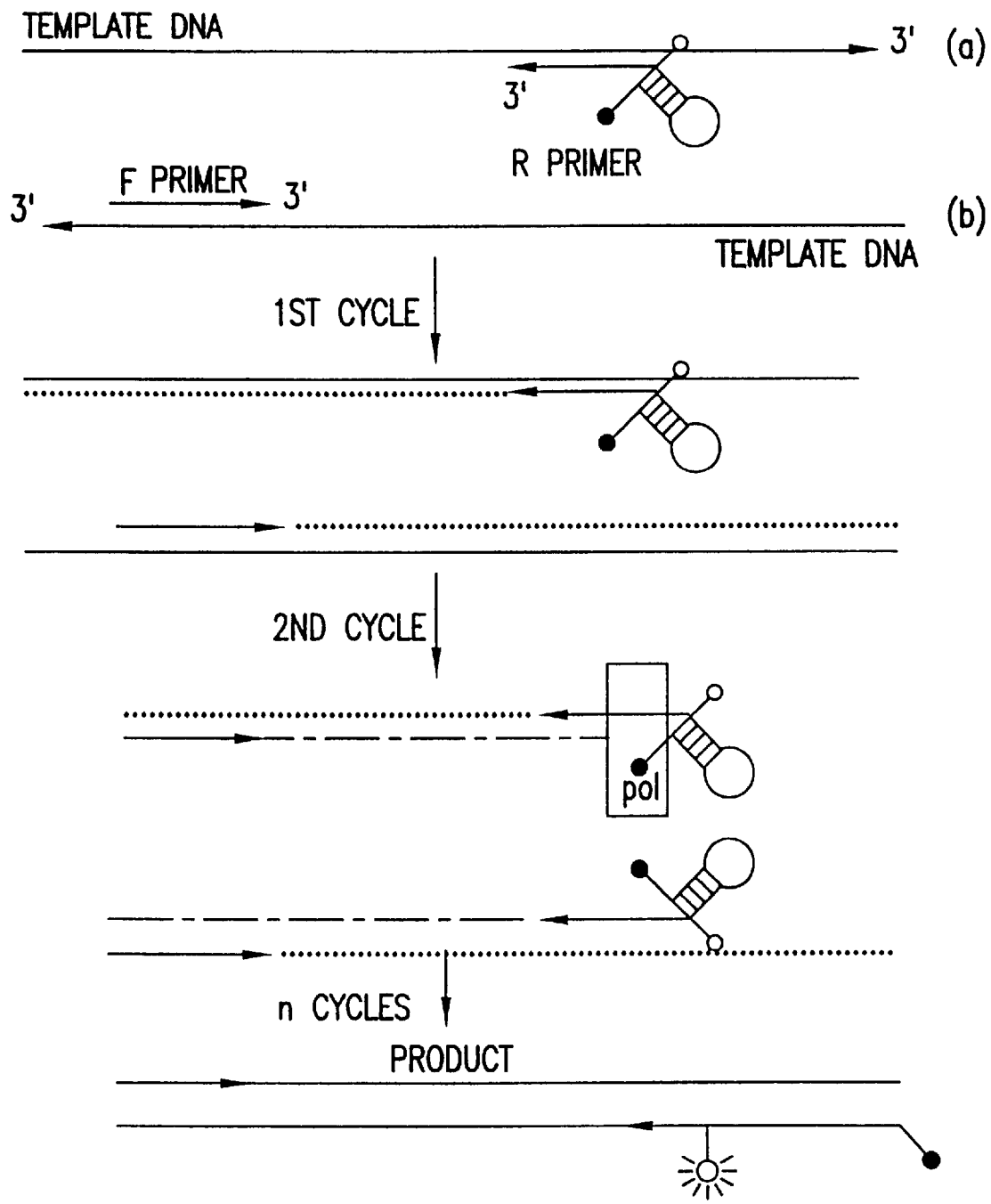

FIG. 2 illustrates schematically the use of hairpin primers to directly measure the amplification products from a PCR in which the employed DNA polymerase lacks 5'-3' exonuclease activity. An energy transfer signal is generated upon the incorporation of the hairpin primer into the double-stranded PCR product. (a) and (b), complementary strands of the target sequence to be amplified; ○ donor fluorophore; ●, quencher; F, forward primer; R, reverse primer.

Figure 3:
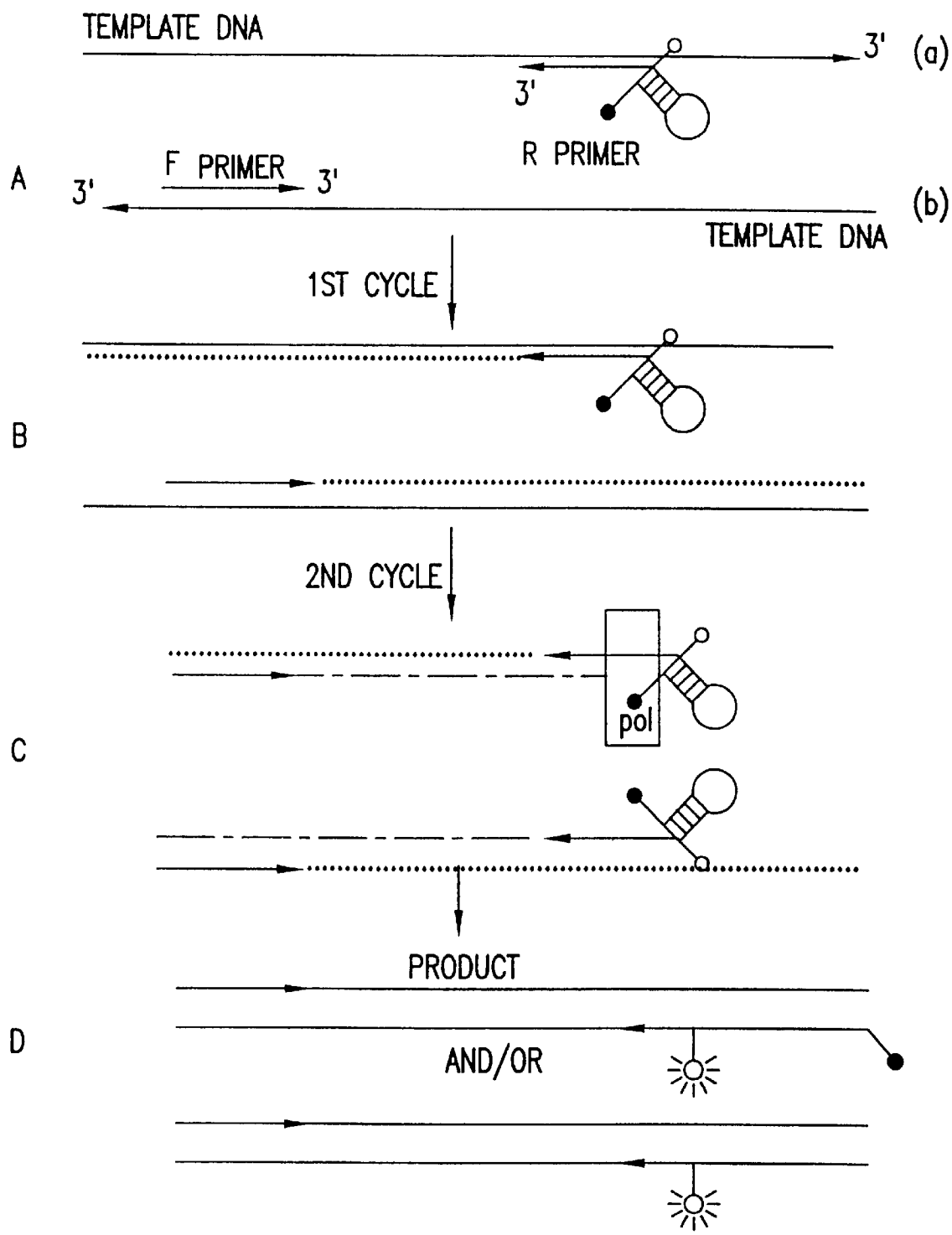

FIG. 3 (Steps A–D) illustrates the amplification products from a PCR in which the employed DNA polymerase has 5'-3' exonuclease activity. (a) and (b), complementary strands of the target sequence to be amplified; ○ donor fluorophore; ●, quencher; F, forward primer; R, reverse primer.

Figure 4:
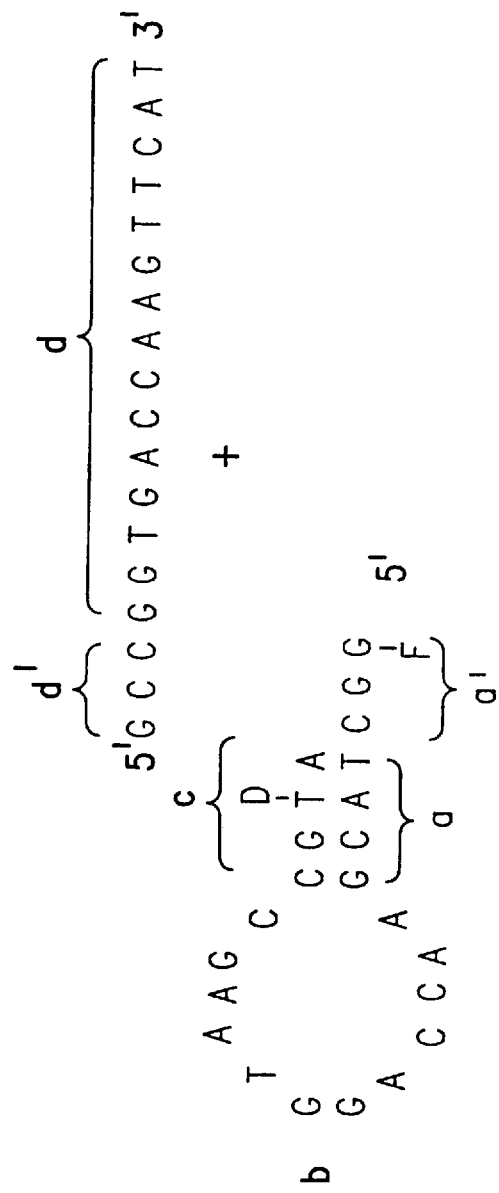

FIG. 4 gives a schematic example of a selected target sequence (SEQ ID NO:1) ligated to a universal hairpin primer (SEQ ID NO:2). (d) is the selected primer sequence of 8–40 nucleotides, preferably ~15 nucleotides, that is complementary to the target nucleic acid sequence to be amplified. (d') is the 5' cohesive end of the selected primer sequence. The cohesive end is 1–10 nucleotides, preferably 3–4 nucleotides, and complementary to the 5' cohesive end (a') of the universal hairpin primer. (b) is a loop on the universal hairpin primer that is long enough provide a distance of 15–25 nucleotides, preferably 20 nucleotides, between the donor (F, FAM) and the quencher (D, DABCYL) when the hairpin is in the "open" configuration. (a) and (c) are the two strands of the stem of the universal hairpin primer. When the selected primer sequence is ligated to the universal hairpin primer, the quencher (DABCYL) will be located on a nucleotide that is internal to the 3' end. The donor (FAM) may be located on a nucleotide either at the 5' end (as shown) or internal to the 5' end. The only requirement is that the donor and quencher are close enough to enable quenching when the hairpin is in the "closed" ("silent") conformation.

Figure 5:
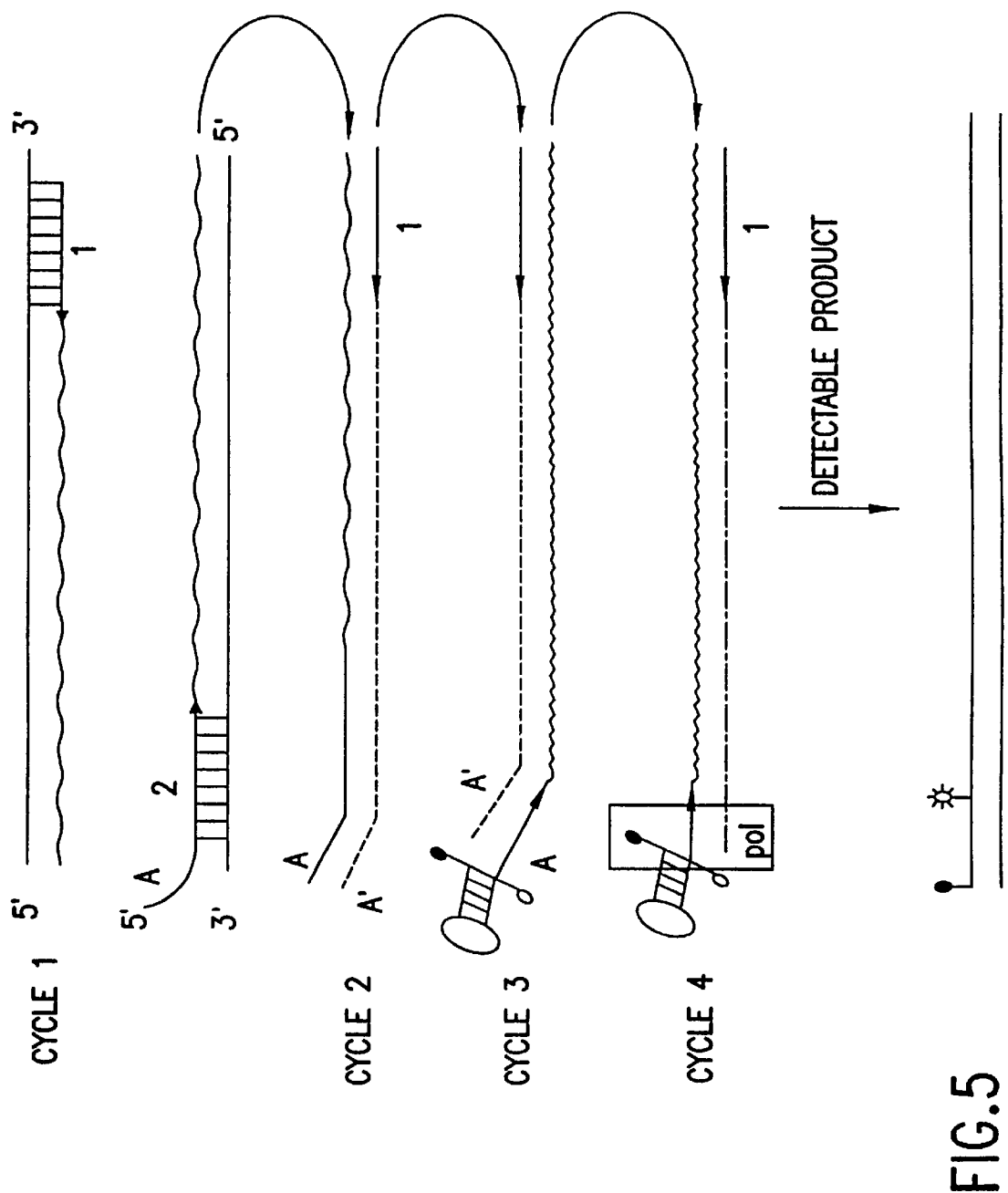

FIG. 5 illustrates schematically the use of a FRET donor-acceptor-labeled hairpin primer in PCR. See Section 5.2.1 for a detailed description of Cycles 1–4.

Figure 6:
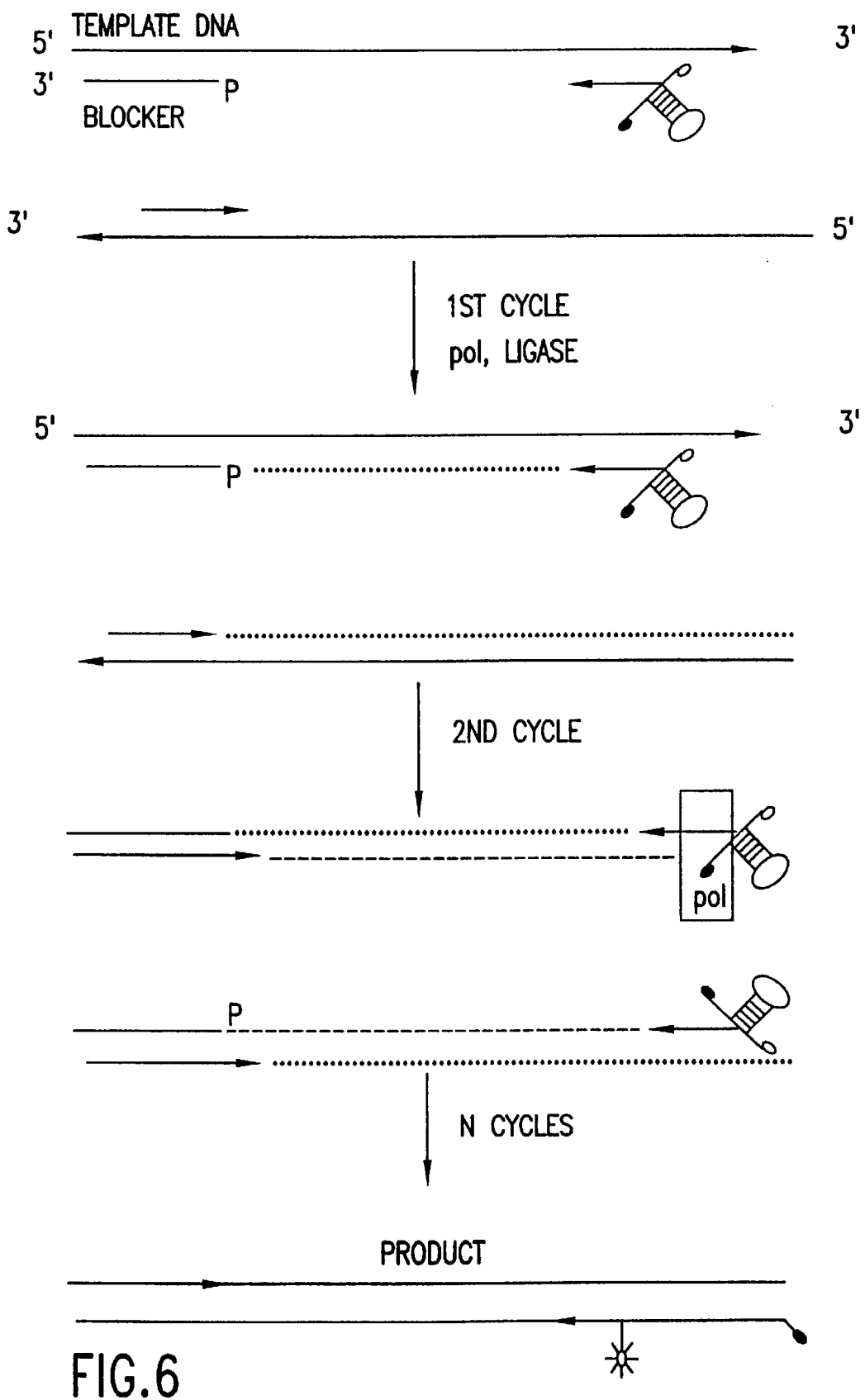

FIG. 6 illustrates schematically the use of a FRET donor-acceptor-labeled hairpin primer in triamplification. In this embodiment of triamplification, unlike in PCR, a third oligonucleotide ("blocker") is ligated to the extended hairpin primer. The fluorescent signal is generated as a result of replication, however, as occurs in PCR.

Figure 7:
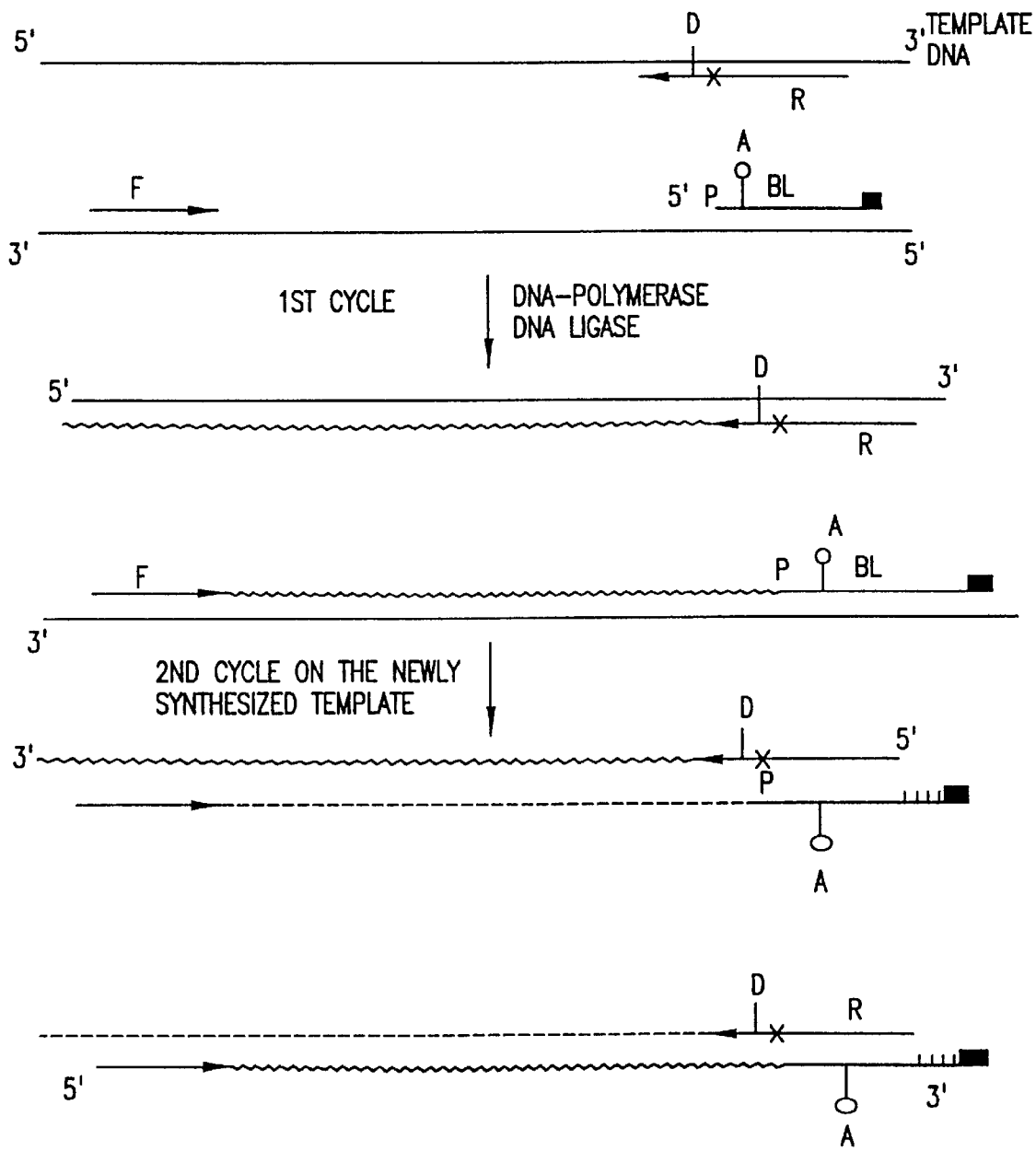

FIG. 7 illustrates schematically triamplification using two linear primers, each labeled with a FRET moiety. BL, blocker; R, reverse primer; F, forward primer; ■, a commercially available 3' modifying group able to protect the oligonucleotide from extension by DNA polymerase or hydrolysis by 3'-5' exonuclease on the 3' end of the blocker; X, 2'-O-methyl-modification in reverse primer; D, donor fluorophore; A○, acceptor fluorophore.

Figure 8A:
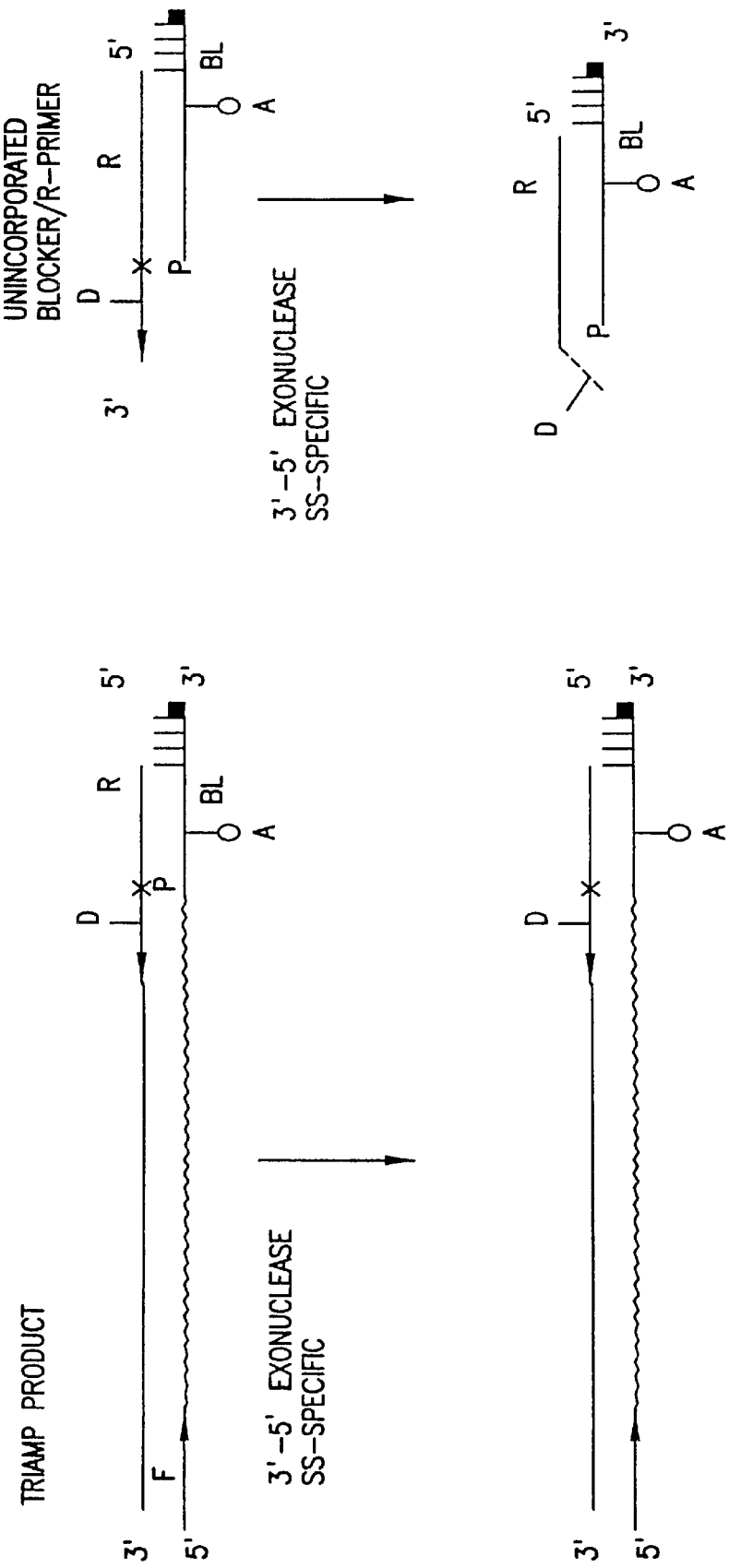
Figure 8B:
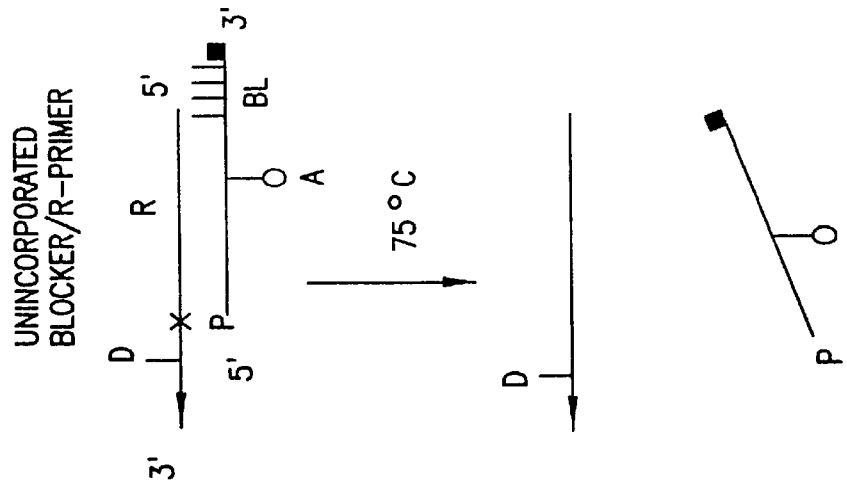

FIGS. 8A–B illustrate the effect of (A) 3'-5' exonuclease and (B) elevated temperature on unincorporated FRET-labeled primers during triamplification. BL, blocker; R, reverse primer; F, forward primer; P, 5' phosphate; ■, protection group on 3'-end of blocker; X, 2'-O-methyl-modification in reverse primer; D, donor fluorophore; A○, acceptor fluorophore.

Figure 9:
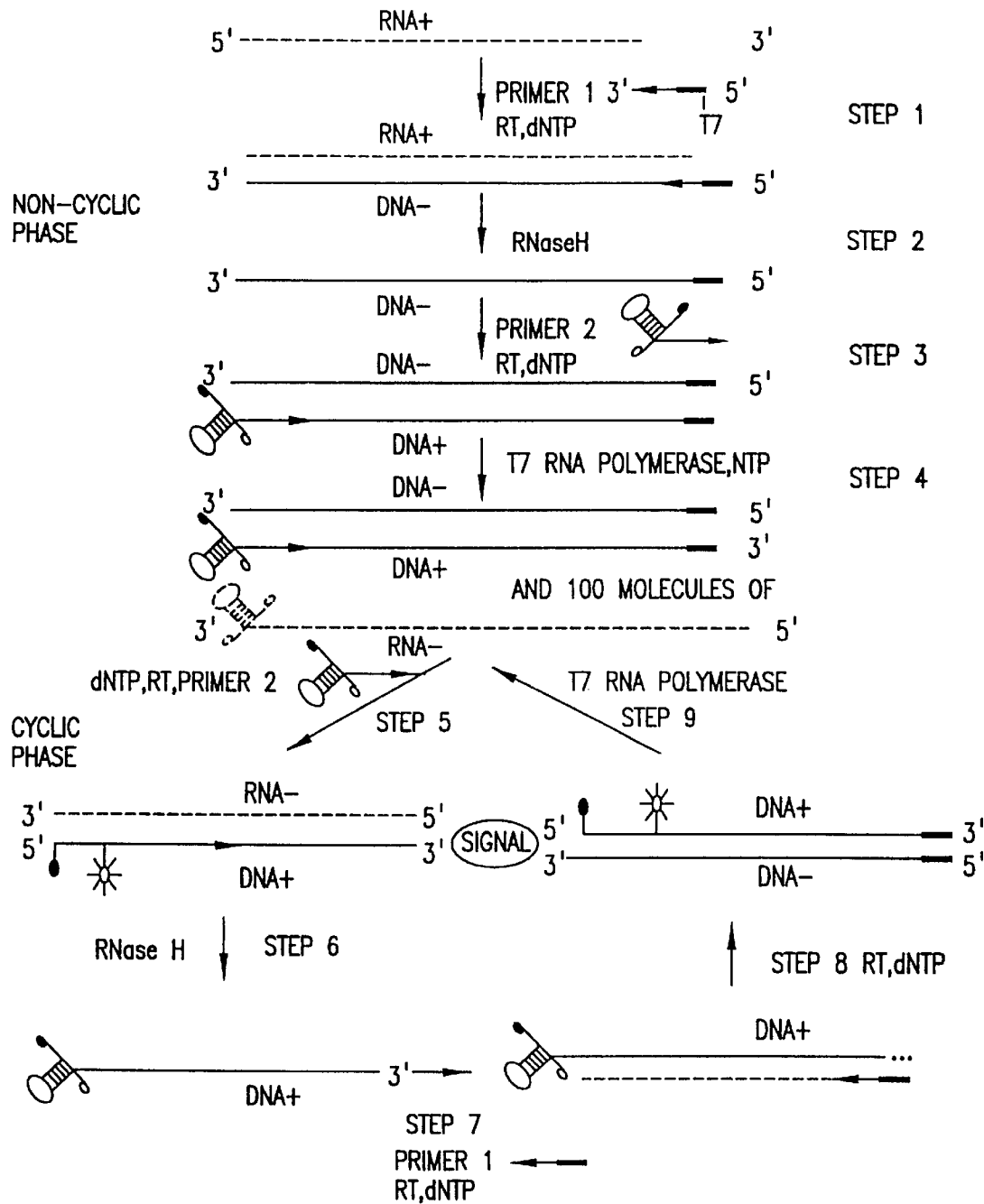

FIG. 9 illustrates schematically the use of hairpin primers in nucleic acid sequence-based amplification (NASBA). NASBA depends on continuous cycling of the reverse transcription and RNA transcription reactions at one temperature. See Section 5.2.3 for a detailed description of Steps 1–9.

Figure 10:
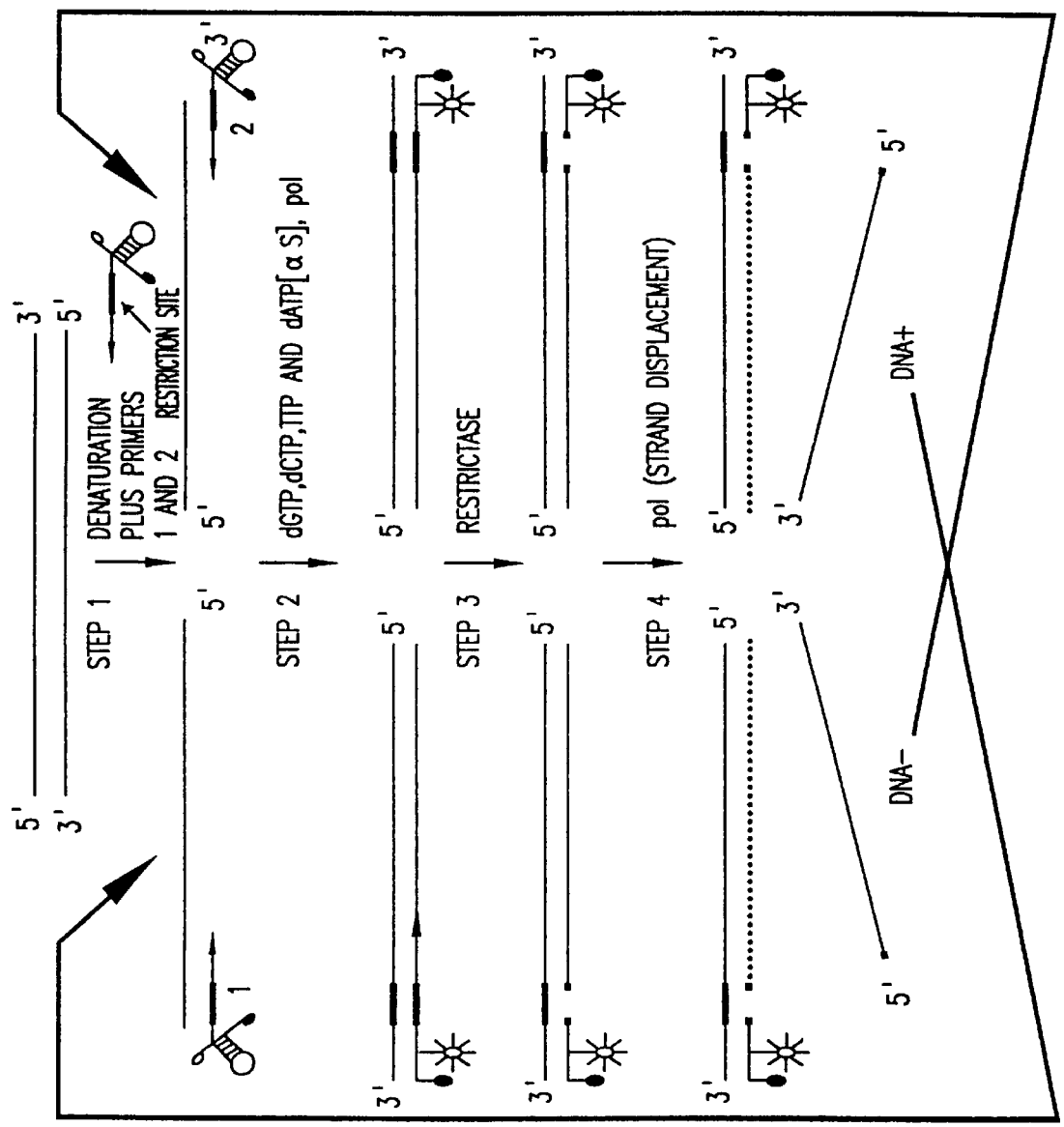

FIG. 10 illustrates schematically the use of hairpin primers in strand displacement amplification (SDA) of a double-stranded DNA target. Primers 1 and 2 differ, being forward and reverse primers, respectively. SDA depends on continuous cycling of the nicking and the polymerization/displacement steps at one temperature. See Section 5.2.4 for a detailed description of Steps 1–4. pol, polymerase; restrictase, restriction endonuclease.

Figure 11A:
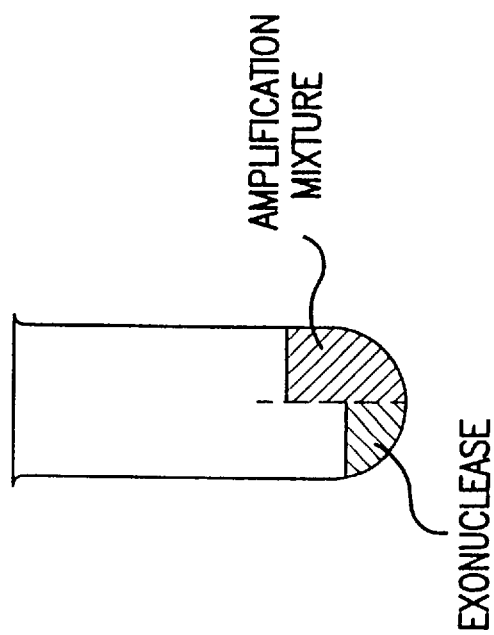
Figure 11B:
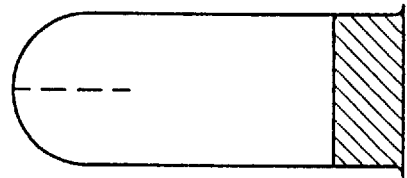

FIGS. 11A–B illustrate a two-chamber amplification tube in "closed-tube" format. The tube can be inverted (FIG. 11B) and used to mix 3'-5' exonuclease with amplification product only when desired, without opening the tube after amplification takes place (see Section 12, Example 6).

FIG. 12 illustrates portions of the two strands (upper strand: SEQ ID NO:3 and SEQ ID NO:4; lower strand: SEQ ID NO:8 and SEQ ID NO:9) of the template, and the oligonucleotides, PSA-I (SEQ ID NO:5), PSA-P (SEQ ID NO:6), and PSA-B (SEQ ID NO:7), used in the amplification of human prostate specific antigen (PSA) DNA as described in all the examples except those employing hairpin primers, the sequences of which are provided in Section 12.

Figure 13A:
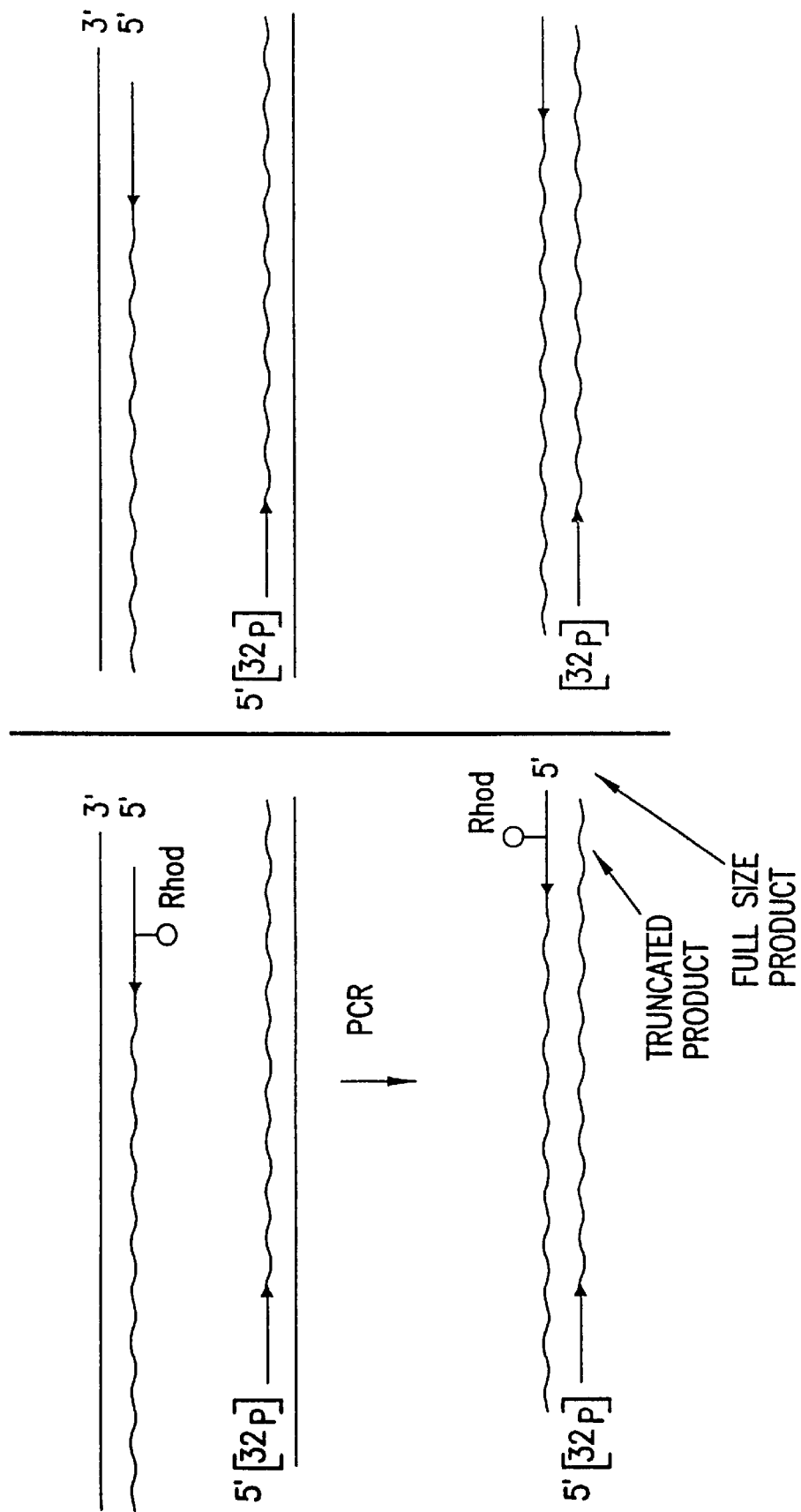
Figure 13B:
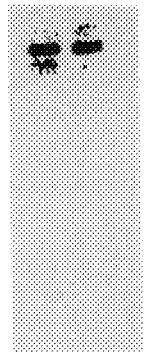
Figure 13C:

FIGS. 13A–C FIG. 13A illustrates schematically the PCR amplification procedure used in the experiment described in Section 7 (Example 1). The left portion of FIG. 13A illustrates a PCR amplification using a rhodamine-modified reverse primer. The right portion of FIG. 13A illustrates a PCR amplification using a non-modified reverse primer. The results are shown on the accompanying denaturing 6% polyacrylamide gel (FIG. 13B) and agarose gel (FIG. 13C). FIG. 13B compares the sizes of the DNA strands that were amplified with [$^{32}$P]-labeled forward primer when non-modified reverse primer (Lane 1) or rhodamine-modified reverse primer (Lane 2) was used. FIG. 13C compares the amounts of double-stranded PCR amplification product obtained with non-modified reverse primer (Lane 1) and rhodamine-modified reverse primer (Lane 2).

Figure 14A:
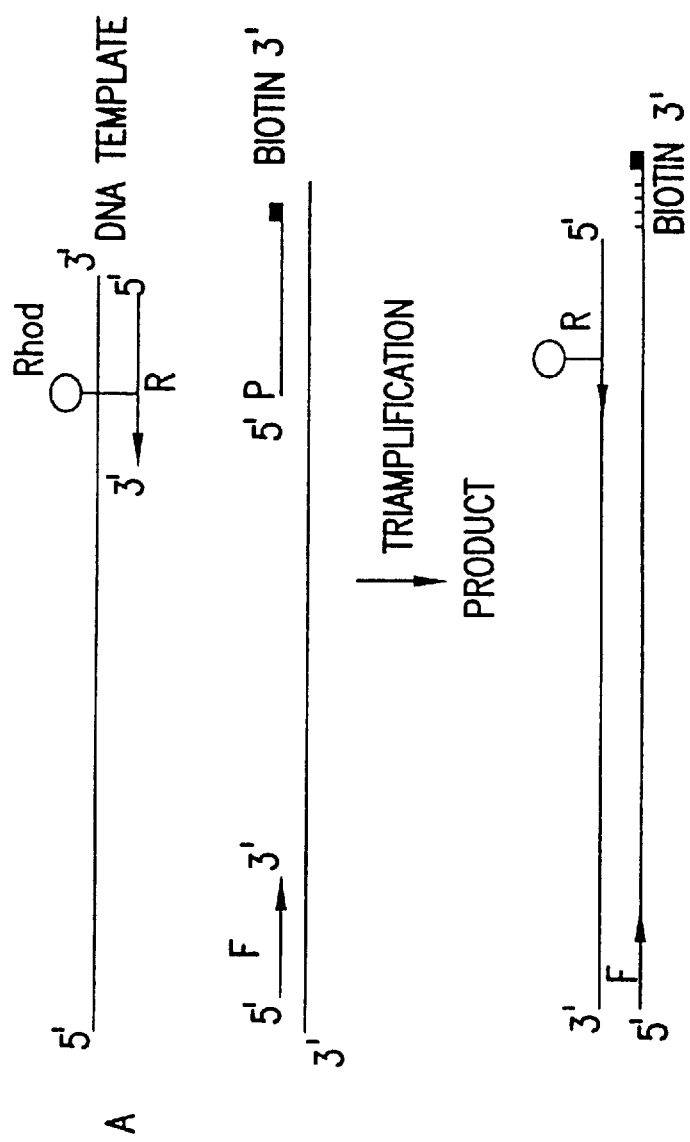
Figure 14B:
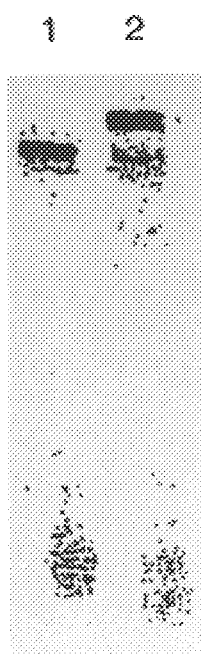

FIGS. 14A–B FIG. 14A illustrates schematically the experimental procedure used in Section 8 (Example 2). The results are shown in the accompanying denaturing 6% polyacrylamide gel (FIG. 14B). Lane 1 of the gel represents a strand of amplified DNA with incorporated [$^{32}$P]-and rhodamine-labeled reverse primer, while Lane 2 represents a strand of amplified DNA with incorporated [$^{32}$P]-labeled forward (F) primer.

Figure 15A:
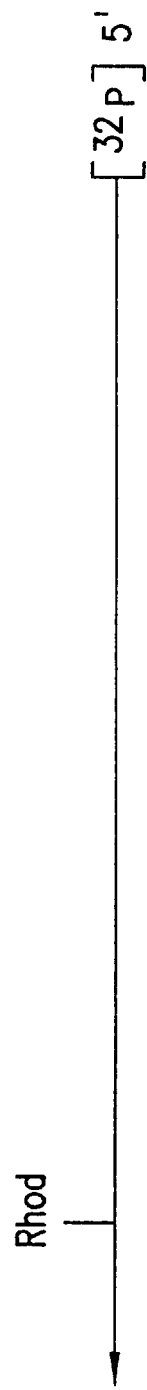
Figure 15B:
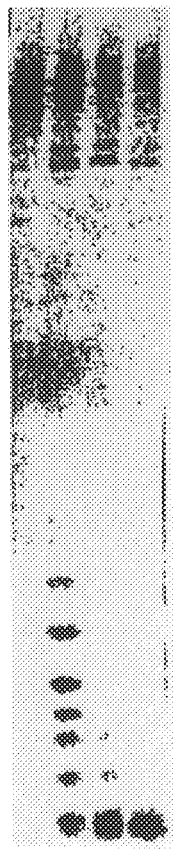

FIGS. 15A–B FIG. 15A illustrates schematically the experimental procedure used in Section 9 (Example 3). The results are shown on the accompanying denaturing 15% polyacrylamide gel (FIG. 15B). Lane 1 of the gel represents [$^{32}$P]- and rhodamine-labeled reverse primer, Lanes 2–4 represent [$^{32}$P]- and rhodamine-labeled reverse primer after incubation with T4 DNA polymerase that has 3'-5' exonuclease activity for 2 minutes (Lane 2), 5 minutes (Lane 3), and 15 minutes (Lane 4).

Figure 16:
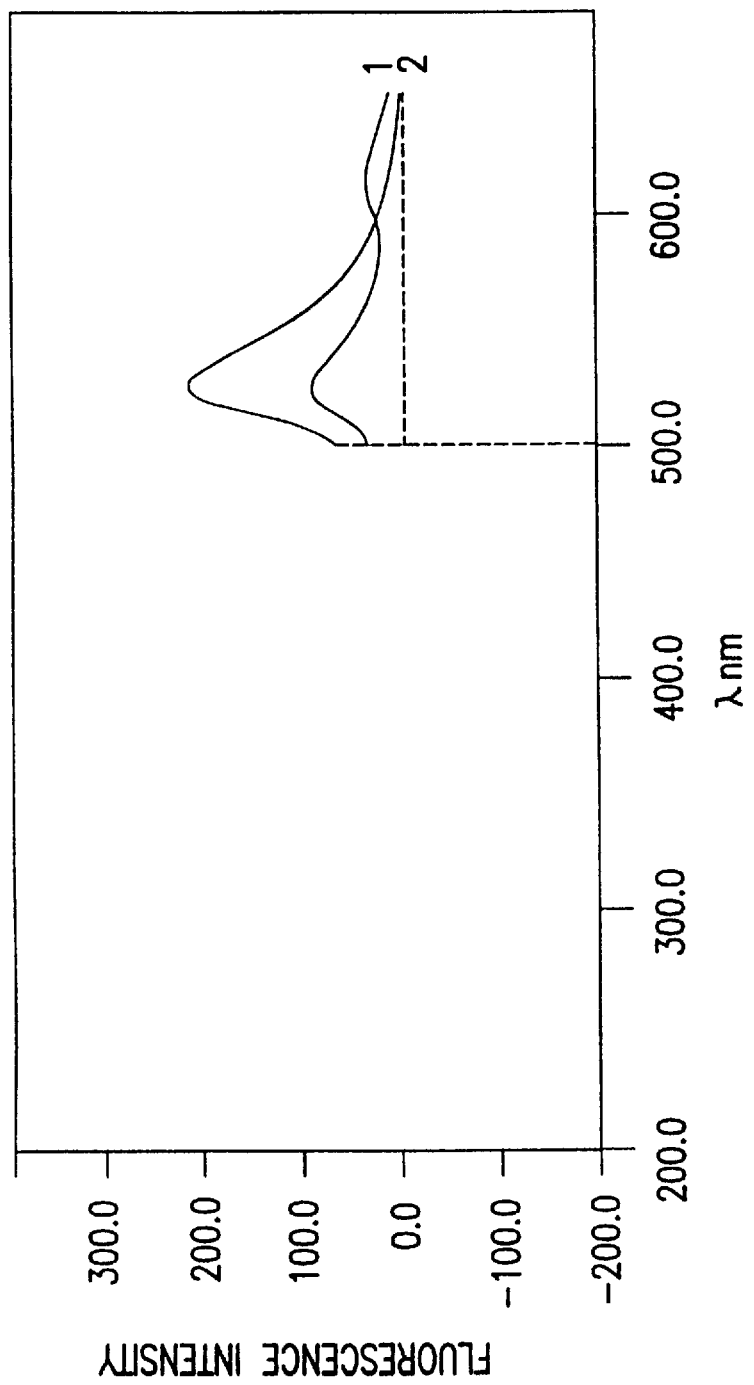

FIG. 16 illustrates the detection of amplification product by FRET after nuclease treatment (Section 10, Example 4). Emission spectrum 1 was obtained after triamplification with DNA template and exonuclease treatment. Spectrum 2 was obtained after triamplification without DNA template and exonuclease treatment (no DNA control).

Figure 17B:
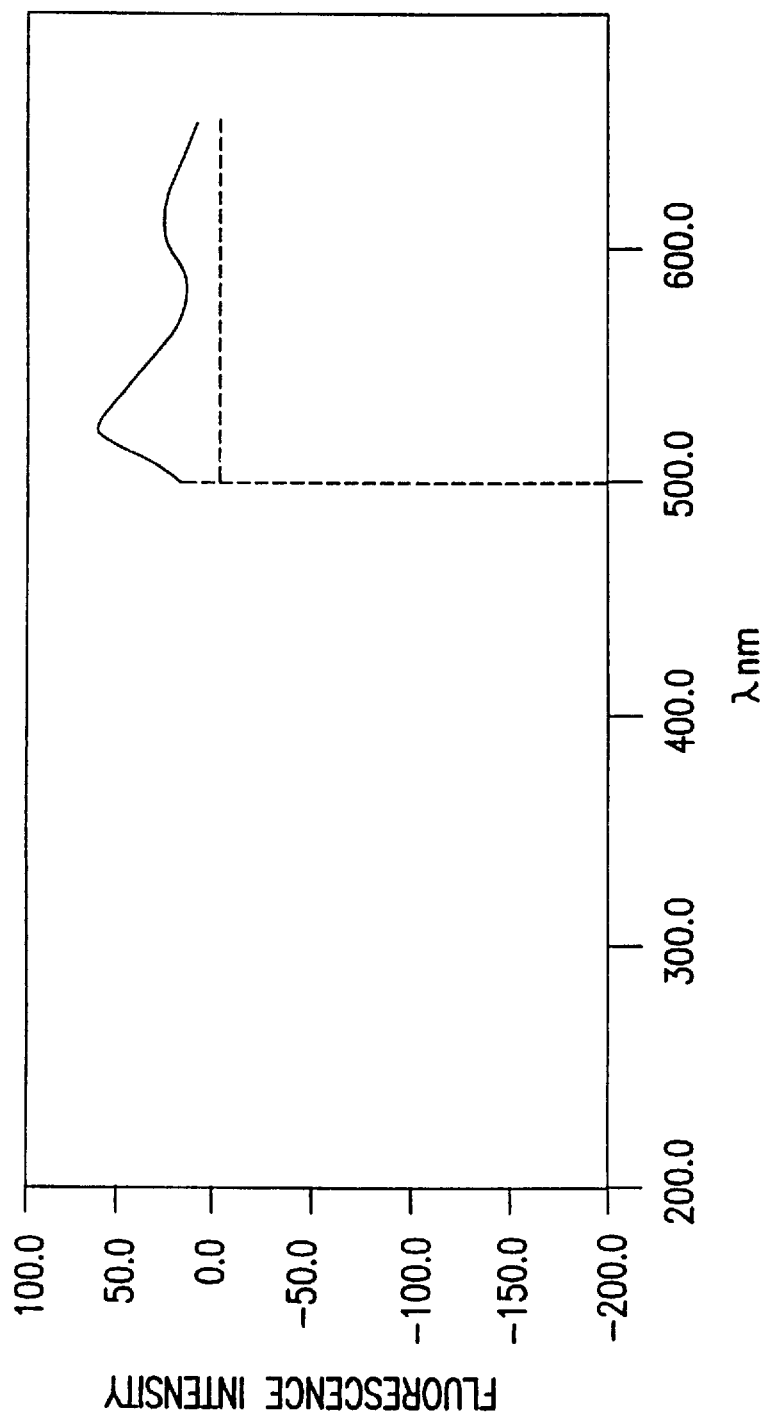

FIGS. 17A–B illustrates the effect of elevated temperatures (75° C.) on FRET following triamplification (A) without and (B) with DNA template (Section 11, Example 5).

Figures 18A, 18B:
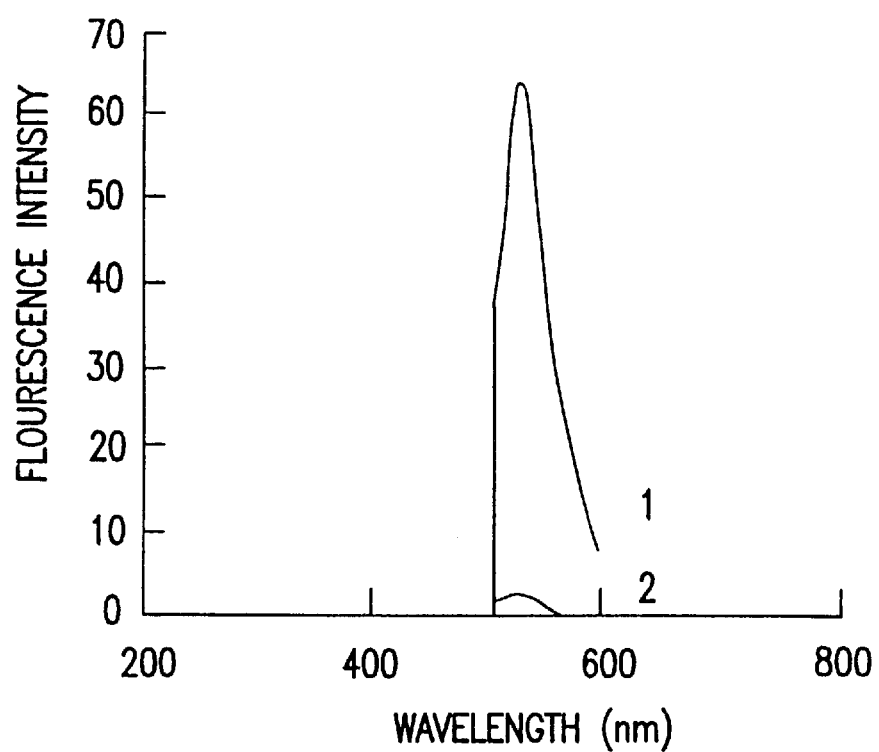

FIGS. 18A–B FIG. 18A depicts the structure of the PSA cDNA upstream hairpin primer (SEQ ID NO:10). The portion of the sequence complementary to the target DNA is shown in bold. FIG. 18B shows an emission spectrum of the fluorescein-labeled hairpin primer in the absence (1) and presence (2) of a DABCYL moiety. The spectra obtained from 0.5 ml of a 40 nM sample of oligonucleotide were measured as described in Section 6.4 using a 488 nm excitation wavelength.

Figure 19:
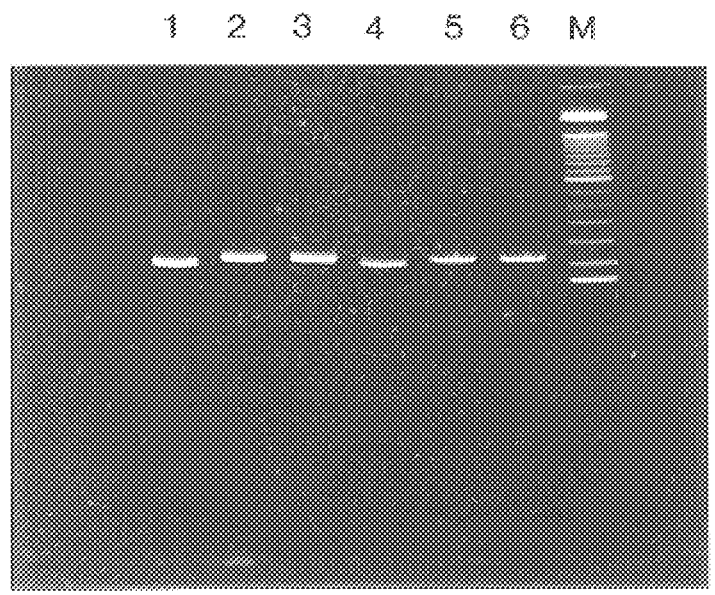

FIG. 19 shows the efficiency of amplification with the hairpin primers. Products of amplification were separated on an MDE gel. An ethidium-bromide stained gel is shown. Lanes 1–3 show the products of amplification of $10^{-9}$M PSA cDNA with unlabeled control linear primer (Lane 1), FAM-hairpin primer (Lane 2), and FAM/DABCYL-hairpin primer (Lane 3). Lanes 4–6 show the products of amplification of $10^{-11}$M PSA CDNA with control primer (Lane 4), FAM-hairpin primer (Lane 5), and FAM/DABCYL-hairpin primer (Lane 6). Lane M contains a 100 bp marker (Gibco BRL).

Figure 20A:
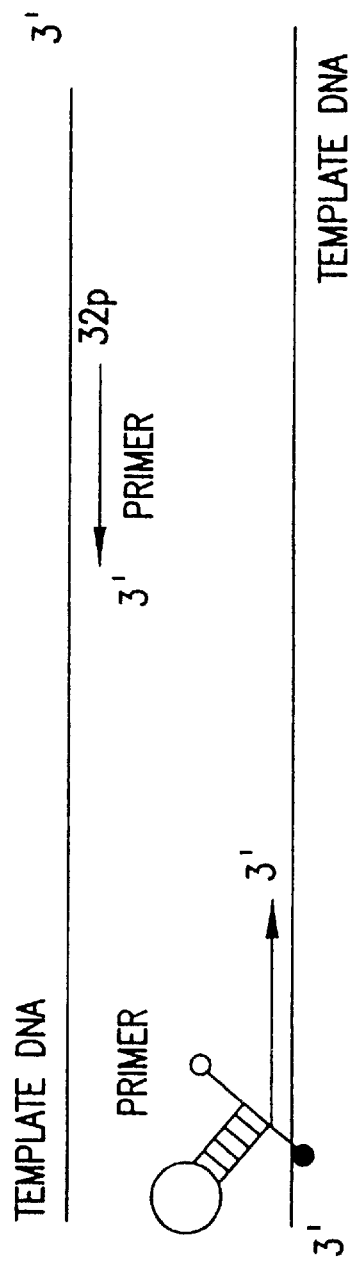
Figure 20B:
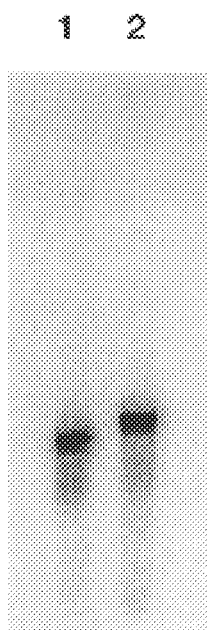

FIGS. 20A–B illustrates schematically and shows the results, respectively, of a PCR amplification in the presence of hairpin primers. PCR amplification of PSA cDNA was performed with two primers: an upstream hairpin primer labeled with FAM and DABCYL, and a downstream primer labeled with $^{32}$P on its 5' end (FIG. 20A). An upstream primer without the hairpin structure was used as a control. The structure of the hairpin primer is presented in FIG. 18A and the sequences of the regular primers are presented in Section 12.3. FIG. 20B is an autoradiogram that shows the size of the PCR product synthesized. [$^{32}$P]-labeled strands of the PCR products were synthesized in the presence of the unlabeled control linear primer (Lane 1) or FAM/DABCYL—labeled hairpin primer (Lane 2) and analyzed on a 6% denaturing polyacrylamide gel.

Figure 21A:
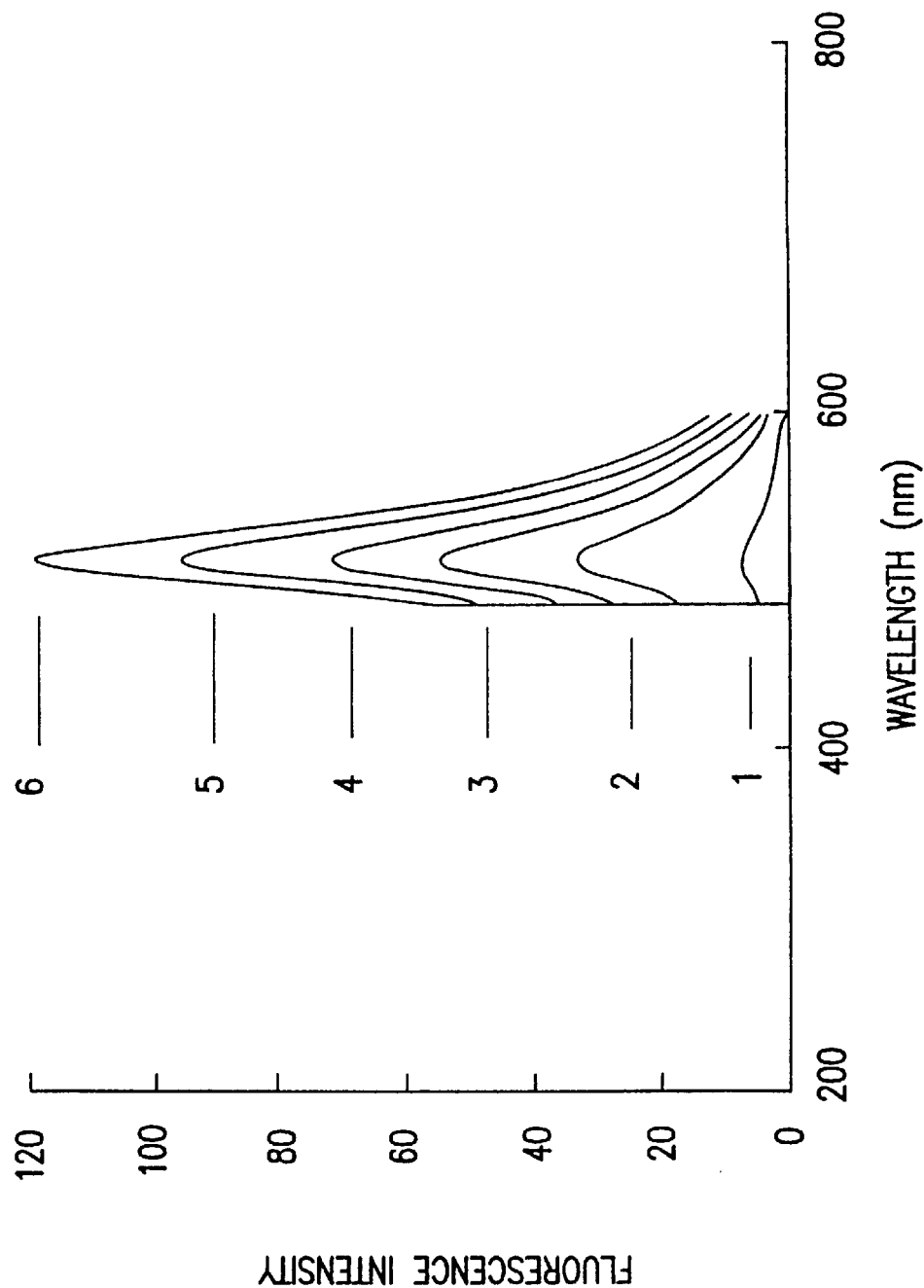
Figure 21B:
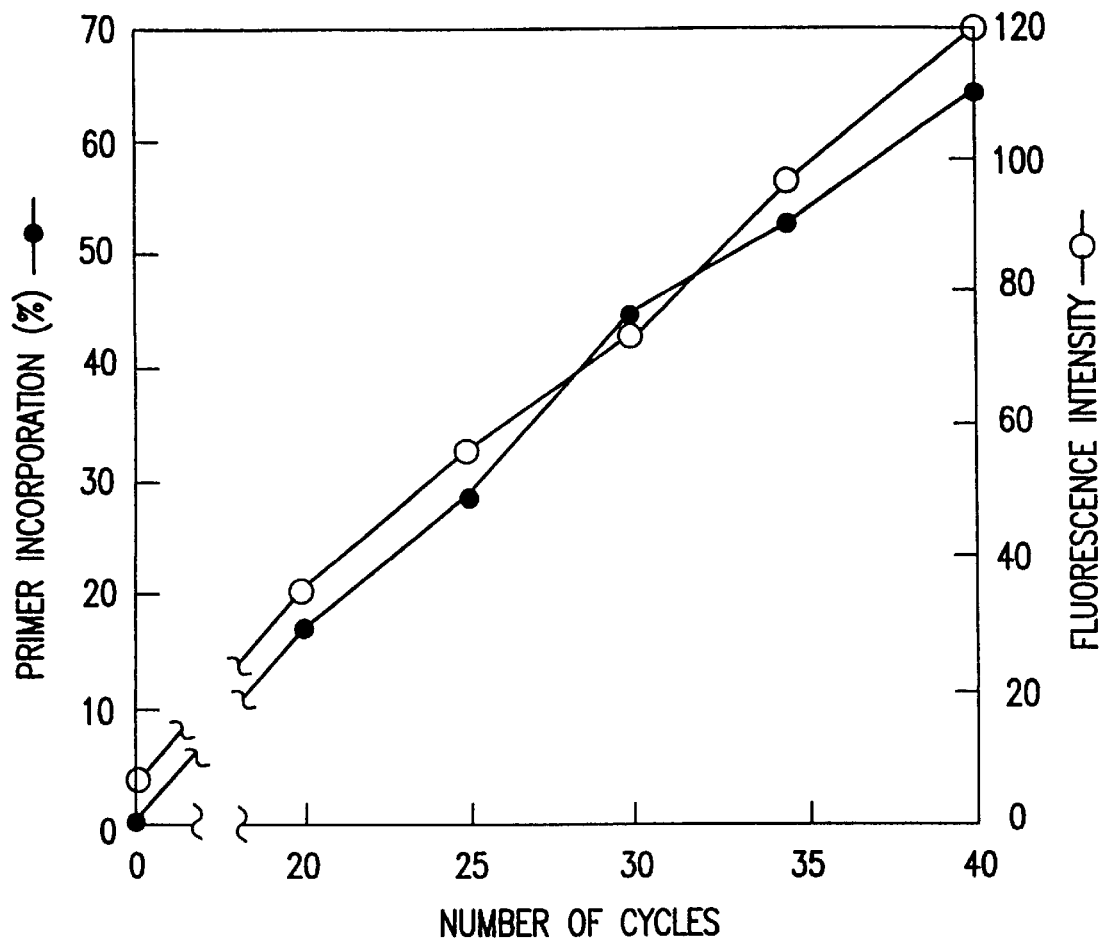

FIGS. 21A–B FIG. 21A shows the fluorescence spectra of the amplification reactions performed with the hairpin primers labeled with FAM/DABCYL. The structure of the FAM/DABCYL labeled hairpin primer is presented in FIG. 18A and the sequence of the regular downstream primer is presented in Section 12.3. Spectra 1–6 show the fluorescence intensity of the amplified PSA cDNA after 0 (1), 20 (2), 25 (3), 30 (4), 35 (5) or 40 (6) cycles. FIG. 21B shows the fluorescence intensity of the amplification reaction mixtures and the fraction of the [$^{32}$P]-labeled primers incorporated into the PCR products plotted against the number of cycles. The incorporation of the [$^{32}$P]-labeled primers into the PCR products was determined by electrophoresis on a 6% denaturing gel and quantitated using the PhosphorImager.

Figure 22:
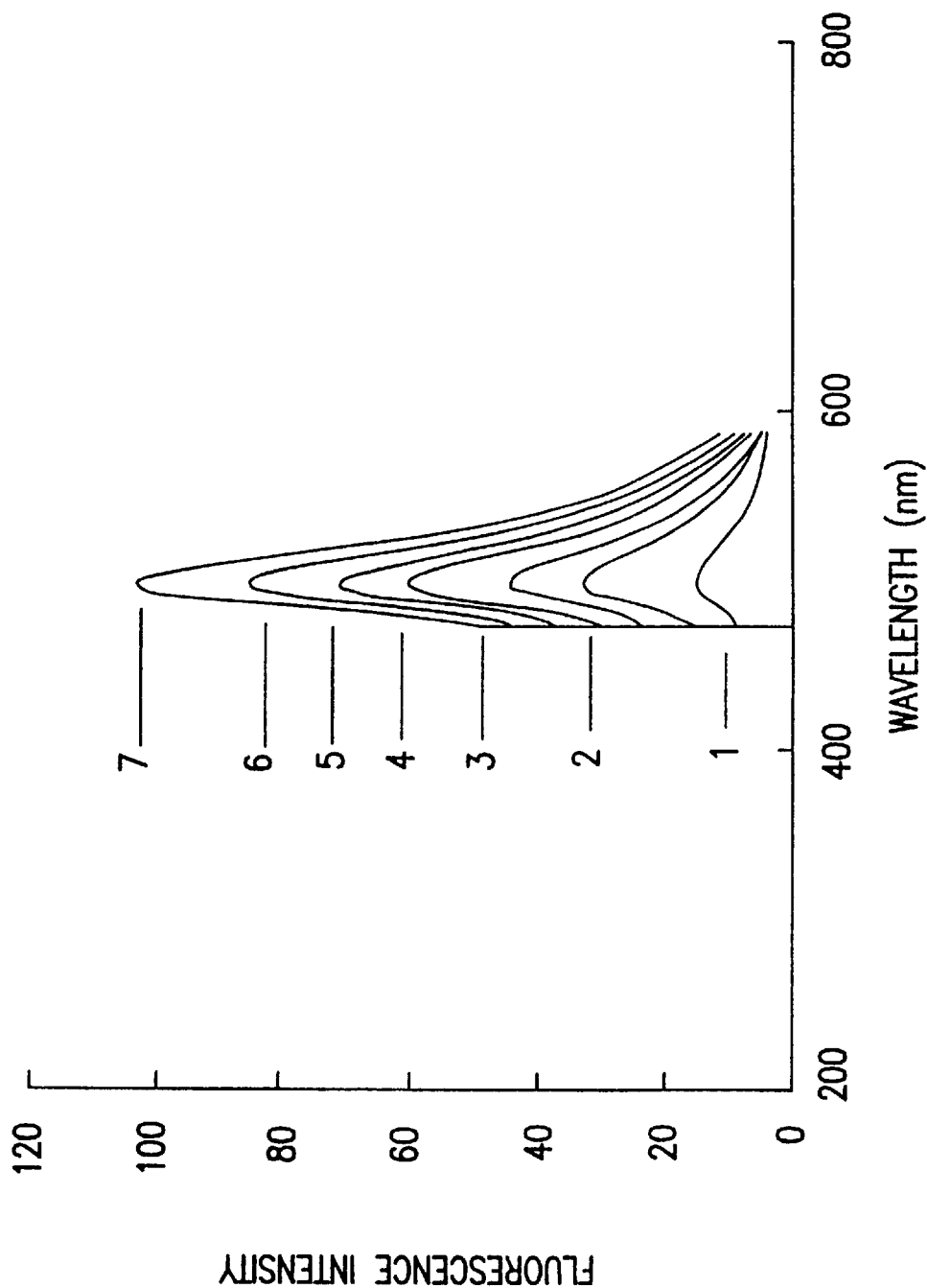

FIG. 22 shows the sensitivity of PCR with hairpin primers. Spectra 1–6 show the results of the amplification when 0 (1), 10 (2), $10^2$ (3), $10^3$ (4), $10^4$ (5), $10^5$ (6) or $10^6$ (7) molecules of cloned PSA CDNA per reaction were used as template DNA for the 40 cycles of PCR. The structure of the FAM/DABCYL labeled hairpin primer is presented in FIG. 18A and the sequence of the regular downstream primer is presented in Section 12.3.

Figure 23:
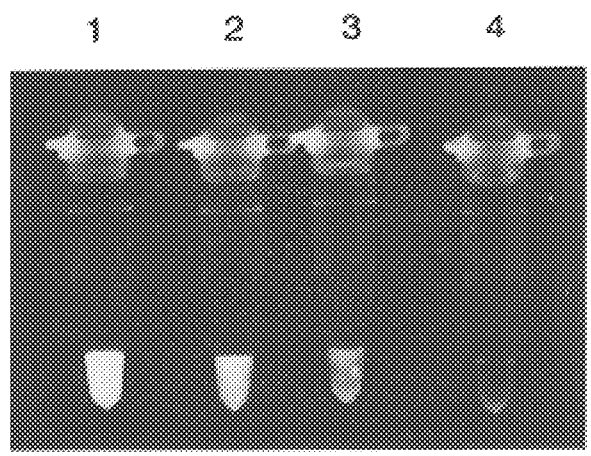
Figure 24A:
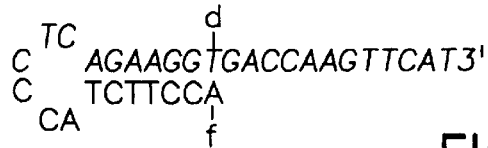
Figure 24B:
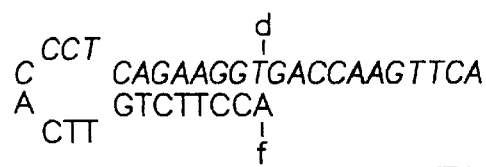
Figure 24C:
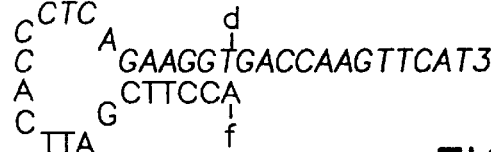
Figure 24D:
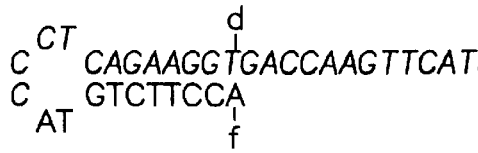
Figure 24E:
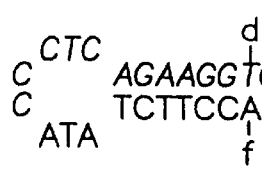
Figure 24F:
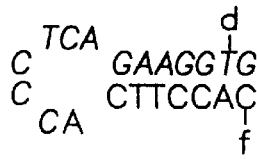
Figure 24G:
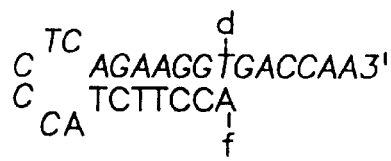

FIG. 23 shows the visible fluorescence of PCR products synthesized with hairpin primers. $10^6$ (Tube 1), $10^4$ (Tube 2), $10^3$ (Tube 3) and 0 (Tube 4) molecules of the cloned PSA cDNA template were used as template DNA for the 40 cycles of PCR with FAM/DABCYL labeled hairpin primers. DNA fluorescence was visualized in 0.2 ml thin-walled PCR tubes using an UV transilluminator image analysis system.

FIGS. 24A–G show the fluorescence intensity of PSA cDNA amplified with different FAM/DABCYL-labeled hairpin primers (FIGS. 24A–G correspond to SEQ ID NOS:13–18, and 25, respectively). All primers had at least an 18-nucleotide sequence complementary to the target, wnich consisted of a 3' single-stranded priming sequence, a 3' stem sequence and part of the loop. Sequences complementary to the target DNA are shown in shadowed bold italics. f, FAM; d, DABCYL; nucl, nucleotide number; rel. (%), percent intensity of fluorescence relative to DNA amplified with Primer A.

Figure 25:
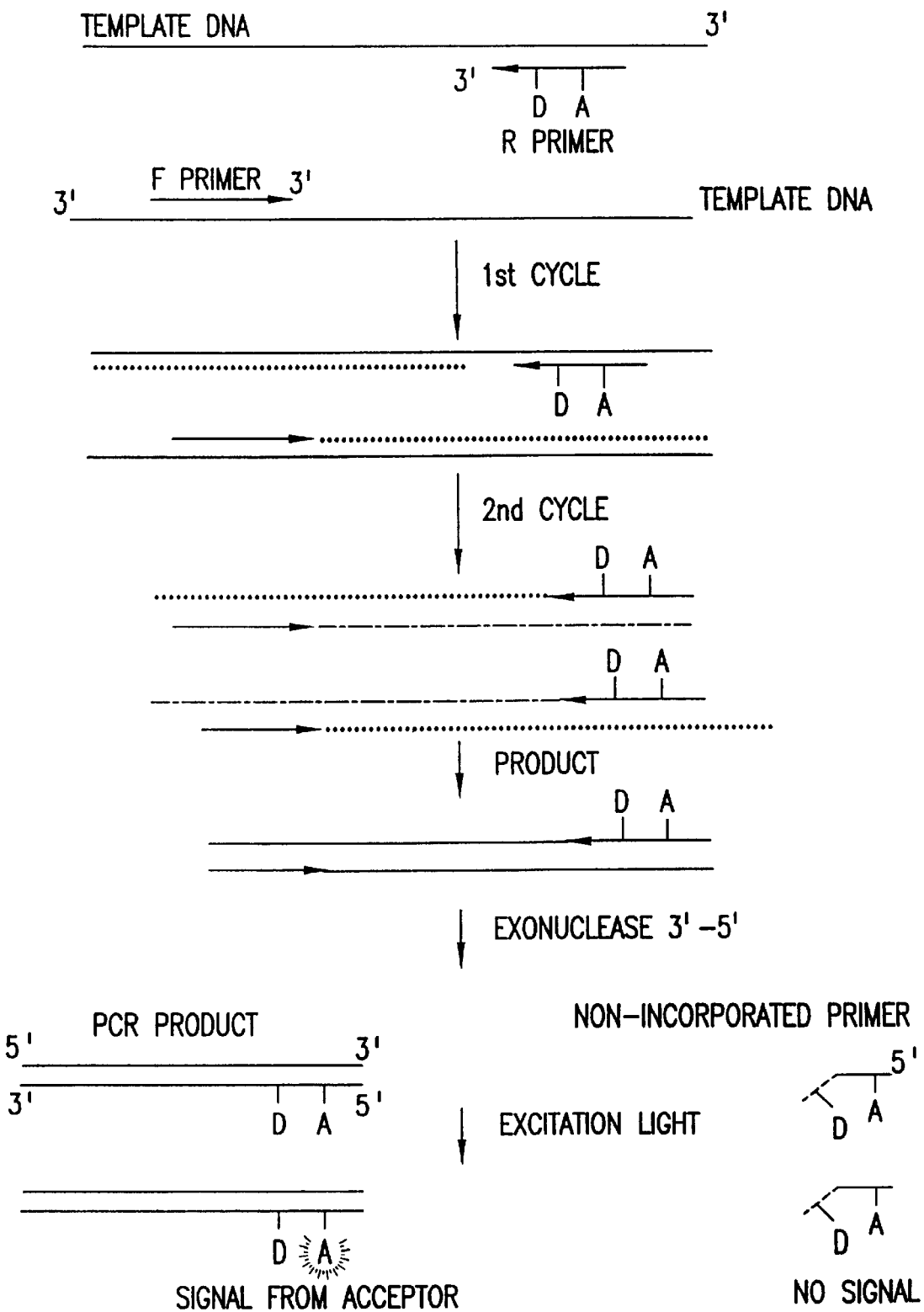

FIG. 25 illustrates schematically the use of linear primers to directly measure the amplification products from a PCR. An energy transfer signal is generated upon the incorporation of the primer into the double-stranded PCR product. After amplification, the signal from unincorporated primer is eliminated by 3'-5' exonuclease hydrolysis. D, donor moiety; A, acceptor moiety; F, forward primer; R, reverse primer.

FIG. 26 illustrates the three sets of PCR primers used in the experiments in Section 13, Example 7. Uup (SEQ ID NO:19) and Ud (SEQ ID NO:20), are the upstream and downstream primers, respectively, for sequences of bisulfite-treated unmethylated DNA. Mup (SEQ ID NO:21) and Md (SEQ ID NO:22), are the upstream and downstream primers, respectively, for sequences of bisulfite-treated methylated DNA. Wup (SEQ ID NO:23) and Wd (SEQ ID NO:24), are the upstream and downstream primers, respectively, for DNA not treated with bisulfite. One of the two primers in each set has a hairpin structure at its 5' end, labeled with a FAM/DAB (DABCYL) FRET pair at the positions illustrated.

5. DETAILED DESCRIPTION OF THE INVENTION

The present invention relates to oligonucleotides for amplification of nucleic acids that are detectably labeled with molecular energy transfer (MET) labels. One or more oligonucleotides of the invention containing a donor and/or acceptor moiety of a MET pair are incorporated into the amplified product of an amplification reaction, such that the amplified product contains both a donor and acceptor moiety of a MET pair. When the amplified product is double-stranded, the MET pair incorporated into the amplified product may be on the same strand or, when the amplification is triamplification, on opposite strands. In certain instances wherein the polymerase used in amplification has 5'-3' exonuclease activity, one of the MET pair moieties may be cleaved from at least some of the population of amplified product by this exonuclease activity. Such exonuclease activity is not detrimental to the amplification methods of the invention.

The invention also relates to methods for detecting the products of nucleic acid amplification using these labeled oligonucleotides of the invention. It further relates to a rapid, sensitive, and reliable method for detecting amplification products that greatly decreases the possibility of carryover contamination with amplification products and that is adaptable to many methods for amplification of nucleic acid sequences, including polymerase chain reaction (PCR), triamplification, and other amplification systems.

The nucleic acid amplification oligonucleotides of the invention utilize the principle of MET between a donor moiety and an acceptor moiety. In a preferred embodiment, the MET is fluorescence resonance energy transfer (FRET), in which the oligonucleotides are labeled with donor and acceptor moieties, wherein the donor moiety is a fluorophore and the acceptor moiety may be a fluorophore, such that fluorescent energy emitted by the donor moiety is absorbed by the acceptor moiety. In one embodiment of the present invention, the acceptor moiety is a fluorophore that releases the energy absorbed from the donor at a different wavelength; the emissions of the acceptor may then be measured to assess the progress of the amplification reaction.

In a preferred embodiment, the amplification primer is a hairpin primer that contains both donor and acceptor moieties and is configured such that the acceptor moiety quenches the fluorescence of the donor. When the primer is incorporated into the amplification product its configuration changes, quenching is eliminated, and the fluorescence of the donor moiety may be detected.

In one embodiment, the present invention provides nucleic acid amplification primers that form a hairpin structure in which MET will occur when the primer is not incorporated into the amplification product. In a preferred embodiment, a primer forms a hairpin structure in which the energy of a donor fluorophore is quenched by a non-fluorescing fluorophore when the primer is not incorporated into the amplification product.

In another embodiment, the present invention provides oligonucleotides that are linear (non-duplex) and that are separately labeled with donor and acceptor moieties, such that MET will occur when the oligonucleotides are incorporated into the amplification product. For example, the blocking oligonucleotide and the primer complementary to the blocking oligonucleotide can be so labeled in a triamplification reaction.

In yet another embodiment, using a pair of linear primers, the donor moiety and acceptor moiety are on a single linear primer used in the amplification reaction. Where the amplification reaction is triamplification, the oligonucleotide labeled with both the donor and acceptor moieties is not the blocking oligonucleotide.

The invention provides a method for detecting or measuring a product of a nucleic acid amplification reaction comprising: (a) contacting a sample comprising nucleic acids with at least two oligonucleotides, a first one of said oligonucleotides comprising a sequence complementary to a preselected target sequence that may be present in said sample, and said first one and a second of said oligonucleotides being a pair of primers adapted for use in said amplification reaction such that said primers are incorporated into an amplified product of said amplification reaction when said target sequence is present in the sample; at least one of said primers being labeled with a first moiety selected from the group consisting of a donor moiety and an acceptor moiety of a molecular energy transfer pair; and wherein the same or a different oligonucleotide is labeled with a second moiety selected from the group consisting of said donor moiety and said acceptor moiety, said second moiety being the member of said group that is not said first moiety, wherein said primer labeled with said first moiety and said oligonucleotide labeled with said second moiety are configured so as to be incorporated into said amplified product, wherein the donor moiety emits energy of one or more particular wavelengths when excited, and the acceptor moiety absorbs energy at one or more particular wavelengths emitted by the donor moiety; (b) conducting the amplification reaction; (c) stimulating light emission from said donor moiety; and (d) detecting or measuring energy emitted by said donor moiety or acceptor moiety.

The nucleic acids in the sample may be purified or unpurified.

A pair of primers, consisting of a forward primer and a reverse primer, for use in PCR or strand displacement amplification, consists of primers that are each complementary with a different strand of two complementary nucleic acid strands, such that when an extension product of one primer in the direction of the other primer is generated by a nucleic acid polymerase, that extension product can serve as a template for the synthesis of the extension product of the other primer. A pair of primers, consisting of a forward primer and a reverse primer, for use in triamplification, consists of primers that are each complementary with a different strand of two complementary nucleic acid strands, such that when an extension-ligation product of one primer in the direction of the other primer is generated by a nucleic acid polymerase and a nucleic acid ligase, that extension-ligation product can serve as a template for the synthesis of the extension-ligation product of the other primer. The amplified product in these instances is that content of a nucleic acid in the sample between and including the primer sequences.

As referred to herein, nucleic acids that are "complementary" can be perfectly or imperfectly complementary, as long as the desired property resulting from the complementarity is not lost, e.g., ability to hybridize.

In a specific embodiment, the invention provides a method for detecting or measuring a product of a nucleic acid amplification reaction comprising (a) contacting a sample comprising nucleic acids with at least two oligonucleotide primers, said oligonucleotide primers being adapted for use in said amplification reaction such that said primers are incorporated into an amplified product of said amplification reaction when a preselected target sequence is present in the sample; at least one of said oligonucleotide primers being a hairpin primer of the invention labeled with a donor moiety and an acceptor moiety; (b) conducting the amplification reaction; (c) stimulating energy emission from said donor moiety; and (d) detecting or measuring energy emitted by said donor moiety.

The present invention also provides a method of directly detecting amplification products. This improved technique meets two major requirements. First, it permits detection of the amplification product without prior separation of unincorporated oligonucleotides. Second, it allows detection of the amplification product directly, by incorporating the labeled oligonucleotide(s) into the product.

The present invention provides a method of directly detecting amplification products through the incorporation of labeled oligonucleotide(s) (e.g., primers, blocking oligonucleotides) wherein instead of separating unreacted oligonucleotides from amplification product, as in prior art approaches, signal from the remaining free oligonucleotide(s) is eliminated in one (or more) of the following ways:

a) by treatment with a 3'-5' exonuclease;
b) by heating the amplification product to a temperature such that the primer-oligonucleotide duplex dissociates and, as a result, will not generate any signal; or
c) by using a primer labeled with both donor and acceptor moieties and that can form a hairpin structure, in which the energy transfer from donor to acceptor will occur only when the primer is not incorporated into the amplification product.

In a further embodiment, the present invention provides a method for the direct detection of amplification products in which the detection may be performed without opening the reaction tube. This embodiment, the "closed-tube" format, reduces greatly the possibility of carryover contamination with amplification products that has slowed the acceptance of PCR in many applications. The closed-tube method also provides for high throughput of samples and may be totally automated. The present invention also relates to kits for the detection or measurement of nucleic acid amplification products. Such kits may be diagnostic kits where the presence of the nucleic acid being amplified is correlated with the presence or absence of a disease or disorder.

For clarity of disclosure, and not by way of limitation, the detailed description of the invention is divided into the subsections set forth below.

5.1. OLIGONUCLEOTIDES

The present invention provides oligonucleotides for nucleic acid amplification that are incorporated into the amplified product and that utilize the principle of molecular energy transfer (MET) and, preferably, fluorescence resonance energy transfer (FRET). The oligonucleotides of the invention are labeled with a donor and/or an acceptor moiety, i.e., a "MET pair." The acceptor moiety may simply quench the emission of the donor moiety, or it may itself emit energy upon excitation by emission from the donor moiety. In a preferred embodiment, the donor moiety is a fluorophore and the acceptor moiety may or may not be a fluorophore, such that fluorescent energy emitted by the donor moiety is absorbed by the acceptor moiety. The labeled oligonucleotides are forward and/or reverse primers, and/or, in the case of triamplification, a blocking oligonucleotide. The oligonucleotides used in the amplification reaction are labeled such that at least one MET pair is incorporated into the amplified product (although 5'-3' exonuclease activity, if present, may subsequently remove a moiety from at least some of the amplified product population).

In one embodiment of the present invention, the acceptor moiety is a fluorophore that releases the energy absorbed from the donor at a different wavelength; use of the emissions of the donor and/or acceptor may then be measured to assess the progress of the amplification reaction, depending on whether the donor and acceptor moieties are incorporated into the amplification product close enough for MET to occur. In another embodiment, the acceptor moiety is a quencher that quenches the fluorescence of the donor when the donor and acceptor moieties are incorporated into the amplification product close enough for MET to occur.

In a further specific embodiment (see Section 5.1.1 infra), an oligonucleotide primer is used that forms a hairpin structure in which FRET will occur, when the primer is not incorporated into the amplification product. In a preferred embodiment, the hairpin primer is labeled with a donor-quencher FRET pair. When the hairpin primer is incorporated into the amplification product, its configuration changes (i.e., it is linearized), quenching is eliminated, and the fluorescence of the donor may be detected.

In yet another embodiment (see Section 5.1.2 infra), the labeled oligonucleotide, that can be a primer or, in the case of triamplification, a blocking oligonucleotide, is a linear molecule that does not form a hairpin configuration. In one embodiment, the donor-acceptor FRET pair is located on the same, single-stranded oligonucleotide primer. In another embodiment, the donor moiety is located on a first oligonucleotide and the acceptor is located on a second oligonucleotide. In a specific embodiment, one of the two FRET-labeled oligonucleotides is a primer for triamplification, and the other FRET-labeled oligonucleotide is a blocker for triamplification (see Section 5.4.2).

The oligonucleotides for use in the amplification reactions of the invention can be any suitable size, and are preferably in the range of 10–100 or 10–80 nucleotides, more preferably 20–40 nucleotides.

The oligonucleotide can be DNA or RNA or chimeric mixtures or derivatives or modified versions thereof, so long as it is still capable of priming the desired amplification reaction, or, in the case of a blocking oligonucleotide, functioning as a blocking oligonucleotide. In addition to being labeled with a MET moiety, the oligonucleotide can be modified at the base moiety, sugar moiety, or phosphate backbone, and may include other appending groups or labels, so long as it is still capable of priming the desired amplification reaction, or functioning as a blocking oligonucleotide, as the case may be.

For example, the oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The oligonucleotides of the present invention may be derived by standard methods known in the art, e.g., by de novo chemical synthesis of polynucleotides using an automated DNA synthesizer (such as is commercially available from Biosearch, Applied Biosystems, etc.) and standard phosphoramidite chemistry; or by cleavage of a larger nucleic acid fragment using non-specific nucleic acid cleaving chemicals or enzymes or site-specific restriction endonucleases.

A preferable method for synthesizing oligonucleotides is conducted using an automated DNA synthesizer by methods known in the art. As examples, phosphorothioate oligonucleotides may be synthesized by the method of Stein et al. (1988, Nucl. Acids Res. 16:3209–3221), methylphosphonate oligonucleotides can be prepared by use of controlled pore glass polymer supports (Sarin et al., 1988, Proc. Natl. Acad. Sci. U.S.A. 85:7448–7451), etc. Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining cligonucleotide that has been separated on. an acrylamide gel, or by measuring the optical density at 260 nm in a spectrophotometer.

Oligonucleotides of the invention may be labeled with donor and acceptor moieties during chemical synthesis or the label may be attached after synthesis by methods known in the art. In a specific embodiment, the donor moiety is a fluorophore. In another specific embodiment, both donor and acceptor moieties are fluorophores. Suitable moieties that can be selected as donor or acceptors in FRET pairs are set forth in Table 1.

TABLE 1

Suitable moieties that can be selected
as donor or acceptors in FRET pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5
    disulfonate (Lucifer Yellow VS)
N-(4-anilino-1-naphthyl)maleimide
anthranilamide
Brilliant Yellow
coumarin and derivatives:
    coumarin
    7-amino-4-methylcoumarin (AMC, Coumarin 120)
    7-amino-4-trifluoromethylcouluarin (Coumaran 151)
cyanosine
4',6-diaminidino-2-phenylindole (DAPI)
5', 5"-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2'7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine TABLE 1-continued Suitable moieties that can be selected
as donor or acceptors in FRET pairs pararosaniline
Phenol Red
B-phycoerythrin
o-phthaldialdehyde
pyrene and derivatives:
    pyrene
    pyrene butyrate
    succinimidyl 1-pyrene butyrate
Reactive Red 4 (Cibacron ® Brilliant Red 3B-A)
rhodamine and derivatives:
    6-carboxy-X-rhodamine (ROX)
    6-carboxyrhodamine (R6G)
    lissamine rhodamine B sulfonyl chloride
    rhodamine (Rhod)
    rhodamine B
    rhodamine 123
    rhodamine X isothiocyanate
    sulforhodamine B
    sulforhodamine 101
    sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Primers are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci., USA 92:4347–4351). These modifications may be used for subsequent incorporation of fluorescent dyes into designated positions of the oligonucleotides.

The optimal distance between the donor and acceptor moieties will be that distance wherein the emissions of the donor moiety are absorbed by the acceptor moiety. This optimal distance varies with the specific moieties used, and may be easily determined by one of ordinary skill in the art using techniques known in the art. For energy transfer in which it is desired that the acceptor moiety be a fluorophore that emits energy to be detected, the donor and acceptor fluorophores are preferably separated by a distance of up to 30 nucleotides, more preferably from 3–20 nucleotides, and still more preferably from 6–12 nucleotides. For energy transfer wherein it is desired that the acceptor moiety quench the emissions of the donor, the donor and acceptor moieties are preferably separated by a distance of less than one nucleotide (e.g., on the opposite strand, complementary nucleotides of a duplex structure), although a 5 nucleotide distance (one helical turn) is also advantageous for use.

In yet another embodiment, the oligonucleotides may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification process.

Oligonucleotides may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Oligonucleotides may be supplementally labeled during chemical synthesis or the supplemental label may be attached after synthesis by methods known in the art.

The oligonucleotides of the invention have use in nucleic acid amplification reactions, as primers, or, in the case of triamplification, blocking oligonucleotides, to detect or measure a nucleic acid product of the amplification, thereby detecting or measuring a target nucleic acid in a sample that is complementary to a 3' primer sequence. Accordingly, the oligonucleotides of the invention can be used in methods of diagnosis, wherein a 3' primer sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target nucleic acid can be genomic or cDNA or mRNA or synthetic, human or animal, or of a microorganism, etc. In another embodiment that can be used in the diagnosis or prognosis of a disease or disorder, the target sequence is a wild type human genomic or RNA or cDNA sequence, mutation of which is implicated in the presence of a human disease or disorder, or alternatively, can be the mutated sequence. In such an embodiment, optionally, the amplification reaction can be repeated for the same sample with different sets of primers that amplify, respectively, the wild type sequence or the mutated version. By way of example, the mutation can be an insertion, substitution, and/or deletion of one or more nucleotides, or a translocation.

5.1.1. HAIRPIN PRIMERS

The present invention provides oligonucleotide primers that form a hairpin structure in which MET will occur when the primer is not incorporated into the amplification product.

Accordingly, in a specific embodiment, the invention provides a hairpin primer that is an oligonucleotide comprising, or alternatively consisting of, the following contiguous sequences in 5' to 3' order: (a) a first nucleotide sequence of 6–30 nucleotides, wherein a nucleotide within said first nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (b) a second, single-stranded nucleotide sequence of 3–20 nucleotides; (c) a third nucleotide sequence of 6–30 nucleotides, wherein a nucleotide within said third nucleotide sequence is labeled with a second moiety selected from the group consisting of said donor moiety and said acceptor moiety, and said second moiety is the member of said group not labeling said first nucleotide sequence, wherein said third nucleotide sequence is sufficiently complementary in reverse order to said first nucleotide sequence for a duplex to form between said first nucleotide sequence and said third nucleotide sequence such that said first moiety and second moiety are in sufficient proximity such that, when the donor moiety is excited and emits energy, the acceptor moiety absorbs energy emitted by the donor moiety; and (d) at the 3' end of said oligonucleotide, a fourth, single-stranded nucleotide sequence of 8–40 nucleotides that comprises at its 3' end a sequence sufficiently complementary to a preselected target sequence so as to be able to prime synthesis by a nucleic acid polymerase of a nucleotide sequence complementary to a nucleic acid strand comprising said target sequence; wherein when said duplex is not formed, said first moiety and said second moiety are separated by a distance that prevents molecular energy transfer between said first and second moiety.

In a specific embodiment wherein the donor and acceptor moieties are a FRET pair, separation of the first and second moiety by a distance that prevents FRET is observed by the failure of the second moiety to quench the fluorescence of the first moiety (when the second moiety is a quencher), or the failure of the second moiety to absorb the fluorescence of the first moiety and then itself to fluoresce (when the second moiety is a fluorophore).

In a specific embodiment, the second nucleotide sequence (the loop structure) and/or the first nucleotide sequence (of the duplex) and/or third nucleotide sequence (of the duplex) do not contain a sequence complementary to the target sequence. Alternatively, the second nucleotide sequence and/or the first nucleotide sequence and/or the third nucleotide sequence or any portion of the foregoing sequences may also contain a sequence complementary to the target sequence.

In a preferred embodiment, a primer forms a hairpin structure in which the energy of a donor fluorophore is quenched by a non-fluorescing acceptor moiety when the primer is not incorporated into the amplification product. One of ordinary skill in the art can easily determine, from the known structures and hydrophobicities of a given FRET pair, the steric arrangement that will bring the pair into closest proximity for MET.

In a specific embodiment, the hairpin primer comprises four parts (FIG. 1): Part (d) is a 3' terminal sequence and comprises a sequence complementary to the target sequence; it is a primer for DNA polymerase. Part (c) is a first stem sequence on the 5' end of the primer sequence. Part (b) forms a single-stranded loop of nucleotides. Part (a) is a second stem sequence, which is complementary to the first stem sequence. Parts (a), (b), and (c) or portions thereof may or may not be complementary to the target DNA to be amplified. Part (d) is preferably 8–30 nucleotides long; Part (c) is preferably 6–30 nucleotides long; Part (b) is preferably 3–20 nucleotides long.

The first stem sequence, Part (c), contains the donor fluorophore and the second stem sequence, Part (a), contains the acceptor (e.g., quencher), or it can be opposite. In a non-incorporated hairpin primer, the emission of the donor will be transferred to the acceptor, since the two moieties will be in close proximity to each other when two stem sequences are in duplex.

The donor and acceptor moieties can be located on either terminal nucleotides of the hairpin stem (duplex region), or internally located. Thus, in one embodiment of the invention, the donor and acceptor (or quencher) moieties are respectively located on the 5' end of the hairpin primer sequence that is complementary to the target and located on the complementary nucleotide residue on the hairpin stem (FIG. 1), or vice versa. Each moiety may alternatively be located on a nucleotide internal within a complementary stem sequence. Alternatively, one of the moieties may be located on an internal nucleotide and the other on the terminal nucleotide at the 5' end. One or both of the moieties may alternatively be located at the other end of the duplex region.

Preferably, donor and acceptor moieties are attached to the complementary strands of the stem, one moiety on the 5' end and the other moiety 5 bp apart on the complementary strand. For example, the two moieties can be offset by a 5 bp (180°) turn of the double helix formed by the two complementary strands of the stem, and will therefore be in closest proximity sterically, and the emission of the donor will be transferred to (and, e.g., quenched by) the acceptor.

Alternatively, the two moieties can be on complementary strands of the stem separated by a distance of less than 1 nucleotide (3.4 Å) when the hairpin is in the closed configuration. Most preferably, the two moieties are on complementary nucleotides on the stem, directly opposite from one another when the hairpin is in the closed configuration.

When a hairpin primer is linearized, the donor moiety must be separated from the acceptor (e.g., quencher) moiety by an intervening sequence that is long enough to substantially prevent MET. Where a FRET pair that consists of donor and acceptor fluorophores is used, the two FRET moieties are separated by an intervening sequence, comprising (a) at least a portion of the first stem sequence, (b) the loop, and (c) at least a portion of the second stem sequence; the intervening sequence being preferably 15–25 nucleotides in length, and more preferably, 20 nucleotides in length.

In one embodiment, the acceptor moiety is a fluorophore that will re-emit the energy provided by the donor at a different wavelength; that is, when the primer is in the closed state, emissions from the acceptor, but not from the donor, will be detected. In a preferred embodiment, the acceptor moiety is a quencher and absorbs the energy emitted by the donor without fluorescing. In either case, the fluorescence of donor may be detected only when the primer is in the linearized, open state i.e., is incorporated into a double-stranded amplification product. Energy transfer in this state will be minimal and the strong emission signal from the donor will be detected.

A critical aspect of the invention is that the transition from the closed to the open state occurs only during amplification. FIGS. 2 and 3 schematically illustrate the use of the hairpin primers of the present invention in PCR. In FIG. 2, the DNA polymerase used in PCR lacks 5'-3' exonuclease activity, whereas in FIG. 3, it has 5'-3' activity. For PCR, either one or both PCR primers can be a hairpin primer.

In FIGS. 2 and 3, (a) and (b) are two complementary strands of the target sequence to be amplified and "R" and "F" are the reverse and forward primers, respectively, for PCR amplification. By way of example and not limitation, the reverse hairpin primer is designed such that there is a donor fluorophore and quencher incorporated into it. Reverse hairpin primer that is not incorporated into the PCR product will have fluorophore and quencher in close proximity; thus the fluorescence from the free reverse primer will be quenched. See Section 5.2.1 infra for methods of use of hairpin primers in PCR.

5.1.1.1. UNIVERSAL HAIRPIN PRIMERS

In one embodiment, the oligonucleotide primer of the invention is a "universal" hairpin primer that can be ligated, either chemically (e.g., using cyanogen bromide) or enzymatically (e.g., using ligase) to any selected primer sequence and used to amplify a target nucleic acid sequence that contains the complement of the primer sequence. The invention provides a "universal" hairpin primer that is an oligonucleotide, the nucleotide sequence of which consists of the following contiguous sequences in 5' to 3' order: (a) a first single-stranded nucleotide sequence of 1 to 10 nucleotides; (b) a second nucleotide sequence of 2–30 nucleotides, wherein a nucleotide within said first nucleotide sequence or said second nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (c) a third, single-stranded nucleotide sequence of 3–20 nucleotides; (d) a fourth nucleotide sequence of 2–30 nucleotides, wherein a nucleotide within said fourth nucleotide sequence is labeled with a second moiety selected from the group consisting of said donor moiety and said acceptor moiety, and said second moiety is the member of said group not labeling said first or second nucleotide sequence, wherein said fourth nucleotide sequence is sufficiently complementary in reverse order to said second nucleotide sequence for a duplex to form between said second nucleotide sequence and said fourth nucleotide sequence such that said first moiety and second moiety are in sufficient proximity such that, when the donor moiety is excited and emits energy, the acceptor moiety absorbs energy emitted by the donor moiety.

An example of a universal hairpin primer is shown in FIG. 4. The universal hairpin primer of the invention comprises a first stem sequence on the 3' end (2–30 nucleotides long, preferably 4–6 nucleotides long), a loop (3–20 nucleotides long, preferably 4–6 nucleotides long), a second stem sequence essentially complementary to the first stem sequence (2–30 nucleotides long, preferably 4–6 nucleotides long), and a 5' single-stranded cohesive ("sticky") end sequence (e.g., 1–10 nucleotides long, preferably 3–4 nucleotides long). In a specific embodiment, the "sticky" end sequence is 5'GGC-3'.

Selected primer sequences that are complementary to a target DNA sequence and that are suitable for ligation to the universal hairpin primer may be derived by standard methods known in the art, e.g., by de novo chemical synthesis of polynucleotides using an automated DNA synthesizer and standard phosphoramidite chemistry; or by cleavage of a larger nucleic acid fragment using non-specific nucleic acid cleaving chemicals or enzymes or site-specific restriction endonucleases.

In order to join a universal hairpin primer to the selected primer sequence, the selected primer sequence should contain a cohesive sequence on the 5' end essentially complementary to the cohesive sequence of the universal hairpin primer (FIG. 4). In one embodiment, the 5' cohesive end on the selected primer sequence is chemically synthesized to complement the 5' cohesive end on the universal hairpin primer. In another embodiment, the 5' cohesive end on the selected primer sequence is produced by the staggered cut of a restriction endonuclease.

A labeling moiety on the universal hairpin primer must not be situated so as to substantially interfere with subsequent ligation at its 3' end to the selected primer sequence. Thus, preferably, a labeling moiety is not located on the 3' terminal nucleotide of the universal hairpin primer (FIG. 4). At the 5' end of the hairpin, a labeling moiety may be located either on the terminal nucleotide at the 5' end (as shown in FIG. 4) or on a nucleotide internal to the 5' end.

The donor (fluorescent) and acceptor (quencher) moieties of a universal hairpin primer such as shown in FIG. 4 must be separated by a distance such that the emissions of the donor moiety are quenched by the acceptor moiety. Preferably, the donor and acceptor moieties are separated by a distance of less than 1 nucleotide (3.4 Å) when the hairpin is in the closed configuration.

In one embodiment, the two FRET moieties are separated by an intervening sequence, comprising a portion of the first stem sequence, the loop, and a portion of the second stem sequence, that is preferably 15–25 nucleotides in length. More preferably, the loop on the universal hairpin is long enough provide a distance of 20 nucleotides between a donor (e.g., FAM) and a quencher (e.g., DABCYL) when the hairpin is in the "open" configuration.

FIG. 4 gives a schematic example of a selected target sequence (8–40 nucleotides, preferably ~15 nucleotides) and a universal hairpin primer prior to their ligation to each other.

5.1.2. LINEAR OLIGONUCLEOTIDES

In another embodiment, the oligonucleotide primers are both linear molecules that cannot form a hairpin configuration. In a specific embodiment, a donor-acceptor FRET pair are both fluorophores located on the same, single-stranded oligonucleotide primer, within distance of each other so that FRET can occur. In this embodiment, the double-labeling with a FRET pair increases the separation between the excitation and the emission frequencies of a label. This increased separation decreases background fluorescence that can interfere with accurate quantitation of the emission signal.

For example, in a specific embodiment, fluorescein may serve as the donor moiety and rhodamine as the acceptor moiety. Fluorescein exhibits peak excitation at 488 nm, but the excitation spectrum is broad and it exhibits some excitation at its emission frequency at 520 nm. This contributes to an emission artifact at 520 nm that decreases the accuracy and sensitivity of quantitative spectrophotometry when using fluorescein as a single label. If a fluorescein moiety is used as a donor and a rhodamine moiety as an acceptor (rhodamine has peak excitation at 520 nm and peak emission at 605 nm), however, excitation will occur at 488 nm and emission will occur at 605 nm, greatly decreasing background artifact.

In another specific embodiment, the donor moiety is located on a first oligonucleotide primer and the acceptor is located on a second, complementary oligonucleotide. In a referred aspect of this embodiment, one of the two FRET-labeled primers is a primer for triamplification, and the other FRET-labeled oligonucleotide is a blocking oligonucleotide (blocker) for triamplification.

5.2. METHODS FOR DETECTION OF AMPLIFICATION PRODUCTS USING HAIRPIN PRIMERS

In a specific embodiment of a hairpin primer of the invention, the acceptor moiety is a fluorophore or quencher that absorbs the energy transmitted by the donor moiety. In a preferred embodiment, the acceptor moiety is a quencher; the primer is configured such that the acceptor moiety on free primer quenches the fluorescence from the donor. When the primer is incorporated into the amplification product, its configuration changes, quenching is eliminated, and the fluorescence of the donor moiety is detected.

The detection method of the present invention may be applied to any amplification system in which an oligonucleotide is incorporated into an amplification product e.g., polymerase chain reaction (PCR) systems (U.S. Pat. Nos. 4,683,195 and 4,683,202), triamplification systems (TriAmp™, Oncor Inc.; U.S. application Ser. No. 08/461, 823, filed Jun. 5, 1995, which is incorporated by reference herein in its entirety; PCT International Publication No. WO 9417206 A1, dated Aug. 4, 1994; PCT International Publication No. WO 9417210 A1, dated Aug. 4, 1994), nucleic acid sequence-based amplification (NASBA) systems (U.S. Pat. No. 5,409,818; Compton, 1991, Nature 350:91–92), and strand displacement amplification (SDA) systems (Walker et al., 1992, Nucl. Acids Res. 20:1691–1696). As a result of amplification, the hairpin primers are incorporated into the double-stranded polynucleotide amplification products. Although various specific embodiments involving a FRET pair are described hereinbelow as involving a preferred FRET pair consisting of a donor fluorophore moiety and a quencher acceptor moiety, it will be understood that such embodiments could also have been described in terms of the acceptor moiety being a fluorophore rather than a quencher.

5.2.1. METHODS OF USE OF HAIRPIN PRIMERS IN POLYMERASE CHAIN REACTION (PCR)

In one embodiment, the hairpin primers of the invention are used to prime a polymerase chain reaction (PCR), thereby becoming incorporated into the amplification product (examples being illustrated in FIGS. 2 and 3A–D). The PCR primers contain hairpin structures on their 5' ends with FRET donor and acceptor moieties located in close proximity (30 nucleotides or less) on the hairpin stem. The primers are designed in such a way that a fluorescent signal from the donor moiety is generated only when the primers are incorporated into an amplification product. The modified hairpin primers do not interfere with the activity of DNA polymerase, and in a preferred aspect, thermostable Pfu polymerase or Taq polymerase can be used. The forward and/or reverse primers can be hairpin primers.

In the example shown in FIG. 3, the hairpin primer has a quencher on its 5' terminal nucleotide, and contains a donor fluorophore on the opposite strand of its duplex, the fluorophore and quencher being a FRET pair. In the first cycle of PCR (FIG. 3B), both primers will hybridize to the respective target strands and will be extended by DNA polymerase. In the second cycle (FIG. 3C) the extended product from the reverse primer will become a template for the forward primer and extended product from the forward primer will become a template for the reverse primer. When the forward primer is extended to the 5' end of the hairpin structure, either of two things can happen, depending on the DNA polymerase used: either the 5'-3' exonuclease activity of the DNA polymerase will hydrolyze the 5' nucleotides with quencher, and/or DNA polymerase will displace the 5'-end of the hairpin and copy the template. In both cases, the quencher and the fluorophore will be separated from each other and a signal will be generated (FIG. 3D).

Hairpin primers may be employed in any amplification method in which the hairpin primer is not complementary to any other oligonucleotide used in the reaction mixture, and in which the hairpin primer is incorporated into a double-stranded DNA amplification product, e.g., PCR, triamplification, nucleic acid sequence-based amplification (NASBA), and strand displacement amplification (SDA) (see infra). Thus, for example, in triamplification involving the use of a hairpin primer, the other, non-hairpin primer is complementary to the blocking oligonucleotide.

In another specific embodiment (FIG. 5), a universal hairpin primer is used, along with two selected linear primers, Primer 1 and Primer 2, to prime a PCR. In this case, the universal hairpin primer is incorporated into the amplification product and is not ligated to one of the two linear primer sequences. In this embodiment, the 3' sequence of the universal hairpin primer is identical to the 5' sequence of one of the pair of linear forward and reverse primers used in the amplification, and this 5' sequence (sequence "A" on Primer 2 in FIG. 5) must not be complementary to the target sequence.

During the first cycle of PCR, Primer 1, which is complementary to a target DNA (+) strand is extended. Primer 2 has a 3' portion that has a sequence complementary to the target (−) strand and a 5' portion, designated "A" in FIG. 5, that has a sequence that is not complementary to the target. Sequence A is preferably 10–25 nucleotides, and more preferably, 12–15 nucleotides in length.

During the second cycle, the product of the extension of Primer 2 (shown by the arrow) becomes a template for Primer 1. Primer 1 is extended and the amplification product now includes a sequence, designated "A'," complementary to sequence A.

During the third cycle, the A sequence of the hairpin primer anneals to the A' sequence of the amplification product from the previous cycle.

During the fourth cycle, the extended hairpin primer becomes a template for Primer 1. During the extension of Primer 1, the hairpin unfolds, the quencher and fluorophore are separated, and a fluorescent signal is emitted from the amplification product. In a similar way, the method can be applied to triamplification. In this case, the hairpin primer is the primer not complementary to the blocker.

5.2.1.1. METHODS OF USE OF HAIRPIN PRIMERS IN ALLELE-SPECIFIC PCR (ASP)

In another embodiment, primers of the invention are used to prime an allele-specific PCR (ASP). In this embodiment, one or both amplification primers may be hairpin primers. In ASP, a target DNA is preferentially amplified if it is completely complementary to the 3' end of a PCR amplification primer. The 3' end of the hairpin primer should terminate at or within one or 2 bases of a known mutation site in a gene (target DNA) to which it has a complementary sequence. Under the appropriate reaction conditions, the target DNA is not amplified if there is a base mismatch (e.g., a nucleotide substitution caused by a mutation) or a small deletion or insertion, at the 3' end of the primer (Okayama et al, 1989, J. Lab. Clin. Med. 114:105–113; Sommer et al., 1992, BioTechniques 12:82–87). Thus, ASP can be used to detect the presence or absence of at least a single mismatch between the hairpin sequence that is complementary to the preselected target sequence and a nucleic acid in the sample; amplification indicates the absence of such a single mismatch.

5.2.2. METHODS OF USE OF HAIRPIN PRIMERS IN TRIAMPLIFICATION

5.2.2.1. GENERAL STEPS IN TRIAMPLIFICATION REACTIONS

Both hairpin primers and linear primers (see Section 5.3.4) can be used in triamplification reactions.

A triamplification reaction is based on three oligonucleotides: two primers and a blocking oligonucleotide (blocker). An example is shown in FIG. 6. The two primers, a forward and a reverse "extending" primers, are complementary to the two strands of a selected target (template) DNA. A third oligonucleotide, a blocker, is partially complementary to one of the two extending primers. Triamplification utilizes two thermostable enzymes: DNA polymerase and DNA ligase. During the repeated steps of polymerization and ligation, one of the extended primers is ligated to the blocker.

In one version of triamplification (the "gap" version), the forward oligonucleotide is a primer substantially complementary to a first segment at a first end of the target sequence to be amplified. The reverse oligonucleotide is a primer substantially complementary to a second segment at a second end of the target nucleic acid sequence on a different strand of the target nucleic acid. The third oligonucleotide (the "blocker" or "blocking oligonucleotide") is substantially complementary to at least a portion of the forward or reverse primer.

A schematic illustration of gap triamplification, which consists of repeated elongation and ligation of the amplification product, is shown in FIG. 7. Blocker may be used at the same or higher concentration than the concentration of forward and reverse primers. Preferably, blocker is used at a 1.2 to 2-fold higher concentration than the concentration of forward and reverse primers. The primer complementary to the blocker preferably is modified to prevent strand displacement during amplification; in a preferred embodiment, this primer contains 2'-O-methyl at the position complementary to the 5' end of the blocker in order to prevent strand displacement.

In the case where linear primers of the invention are used (Section 5.3.4), the blocker is preferably modified in order to protect it from exonuclease hydrolysis (which is used with amplification methods using linear, but not hairpin primers) and from undesirable extension during amplification. In a preferred embodiment, the blocker has biotin on its 3' end in order to protect it from exonuclease hydrolysis and from undesirable extension during amplification.

An alternate version of triamplification, the "non-gap version," is substantially similar to the gap version described above, with the difference that the 5' end of the forward primer is adjacent to the 3' end of the reverse primer.

5.2.2.2. USE OF HAIRPIN PRIMERS IN TRIAMPLIFICATION REACTIONS

In one embodiment of the invention, hairpin primers are used to prime a triamplification reaction, thereby becoming incorporated into the amplification product. When using hairpin primers in triamplification, the hairpin structure is part of whichever primer, either the forward or the reverse primer, that is not complementary to the blocker (FIG. 6). It cannot be used on the primer complementary to the blocker, because, in this case, the blocker will interfere with the formation of the hairpin on the primer that is not incorporated into the amplification product.

The hairpin primer is preferably labeled with a FRET donor-acceptor pair on its stem. During the first cycle of triamplification, the hairpin primer will be extended and ligated to the blocker. During the second cycle, the extended hairpin primer will become a template for the second primer. In the course of extension of the second primer, the hairpin will open, the quencher will be separated from the fluorophore and the donor will emit a fluorescence signal.

5.2.3. METHODS OF USE OF HAIRPIN PRIMERS IN NUCLEIC ACID SEQUENCE-BASED AMPLIFICATION (NASBA)

The primers of the invention may be used to prime nucleic acid sequence-based amplification (NASBA), an example of which is shown in FIG. 9. NASBA uses continuous cycling of reverse transcription and RNA transcription reactions and is conducted at one temperature. It uses three enzymes (reverse transcriptase, RNase H, and T7 RNA polymerase). In one embodiment, the method uses two primers, one of which is a hairpin primer of the invention that is labeled with FRET donor and acceptor (e.g., quencher) moieties. In an alternative embodiment, both primers are hairpin primers of the invention.

Primer 1 has preferably about 20 bases on its 3' end that are complementary to a target RNA and a promoter sequence 5' to the target-complementary sequence that is recognized by T7 RNA polymerase. Primer 2 is a hairpin primer of the invention that is complementary to the RNA (−) sequence and has a hairpin structure on its 5' end that is labeled with energy transfer moieties such as is illustrated by way of example in FIG. 9.

The non-cycling NASBA phase proceeds as follows (FIG. 9). In Step 1, Primer 1 anneals to the RNA target sequence.

Reverse transcriptase uses dNTPs to extend the 3' end of the Primer 1, forming a RNA/DNA hybrid. In Step 2, RNase H hydrolyzes the RNA strand of the hybrid. In Step 3, hairpin Primer 2 anneals to the single DNA strand remaining from the hybrid. Reverse transcriptase synthesizes the second DNA strand, rendering the promoter region double-stranded. In Step 4, the third enzyme in the mixture, T7 RNA polymerase, binds to the promoter sequence and generates up to 100 RNA copies from each template molecule.

The cycling NASBA phase then proceeds as follows. In Step 5, hairpin Primer 2 binds to the RNA template through its 3' end priming sequence, and reverse transcriptase extends it and generates a RNA/DNA hybrid. The 5' end of the hairpin is displaced and copied as a result of replication. The quencher and the fluorophore are now spaced far enough apart that the fluorophore is no longer quenched and its fluorescence will be detectable. In Step 6, RNase H hydrolyzes the RNA strand. The resulting single-stranded DNA is now "silent" (fluorescence is quenched) because the hairpin structure is formed again. In Step 7, Primer 1 binds to the single-stranded DNA. Reverse transcriptase binds to the 3' ends of both the primer and the DNA template. In Step 8, the 3' end of the single-stranded DNA is extended, yielding a double-stranded, transcriptionally active promoter. Simultaneously, the 3' end of Primer 1 is extended. The 5' end of the hairpin is displaced and copied as a result of replication. The quencher and the fluorophore are now spaced far enough apart that the fluorophore is no longer quenched and its fluorescence will be detectable. In Step 9, T7 RNA polymerase generates multiple RNA copies from each template molecule.

Hence in this embodiment, the amplification products of steps 5 and 8 will have incorporated the FRET-labeled hairpin primer and will give a fluorescent signal during the cyclic phase.

In the above example, a hairpin primer is employed in the NASBA process as described by Compton (1991, Nature 350:91–92). However, if polymerase-specific 5'-3' exonuclease activity is present in addition to reverse transcriptase, T7 RNA polymerase and RNase H, the 5' end of the hairpin-primer will be hydrolyzed during replication. A fluorescence signal will be generated not only at steps 5 and 8, but also at steps 6 and 7, since there will be no quencher attached to the DNA template.

5.2.4. METHODS OF USE OF HAIRPIN PRIMERS IN STRAND DISPLACEMENT AMPLIFICATION (SDA)

The hairpin primers of the invention may be used in strand displacement amplification (SDA) of a double-stranded DNA target. The forward and/or reverse primers can be hairpin primers. SDA depends on the continuous cycling of nicking and polymerization/displacement steps and is conducted at one temperature.

In a specific embodiment (FIG. 10), Primer 1 and Primer 2 are both hairpin primers of the invention. Each has a single-stranded priming sequence on the 3' end, a recognition site for the restriction endonuclease, and a FRET-labeled hairpin structure on the 5' end.

SDA proceeds as follows. In Step 1, the target DNA is denatured and Primer 1 and Primer 2 anneal through their 3' sequences. In Step 2: The 3' ends of the primers are extended using dNTPs, one of which is a 5'-[α-thio]triphosphate. A double stranded restriction site is formed with one modified strand (the thio-modified strand is resistant to endonuclease hydrolysis). At the same time, the 5' end of the hairpin primer is displaced and copied as a result of replication. The quencher and the fluorophore are now spaced far enough apart that the fluorophore is no longer quenched and its fluorescence will be detectable. In Step 3, the non-modified strand of the double-stranded DNA is nicked by the restriction endonuclease. In Step 4, DNA polymerase that lacks 5'-3' exonuclease activity extends the 3' end of the nick, displacing the single-stranded DNA target, which will go through the same cycle again.

Hence in this embodiment, the amplification products of Steps 2, 3 and 4 will have incorporated the FRET-labeled hairpin primer and will give a fluorescent signal.

5.3. METHODS OF DETECTION OF AMPLIFICATION PRODUCTS USING 3'-5' EXONUCLEASE AND/OR ELEVATED TEMPERATURE

The methods of the invention described in the following Section (5.3) may be also combined with those methods described in Section 5.4 (employing linear primers) for use during nucleic acid amplification reactions including PCR, triamplification, NASBA and SDA. Since the use of 3'-5' exonuclease or elevated temperature allows detection of amplified product without the need for separation of unincorporated primers (thus allowing a "closed tube" format), such procedures are preferred for use with linear primers. Since the use of hairpin primers allows one to distinguish between amplified produce and unincorporated primers based on type of signal detected, exonuclease treatment or heat is not necessary for use in procedures employing the hairpin primers of the invention.

5.3.1. USE OF 3'-5' EXONUCLEASE IN AMPLIFICATION REACTIONS

As described in certain of the embodiments in Section 5.4 relating to PCR and triamplification, and also for use with NASBA and SDA, after an amplification reaction is complete, 3'-5' exonuclease can be introduced into the reaction vessel to cleave all free primer. Then, the donor label is stimulated with light of the appropriate wavelength. When the acceptor moiety is a fluorophore, the only acceptor label that will emit is that which remains on uncleaved primer that has been incorporated into the amplified product, thus giving an indication of the extent of amplification. The further amplification has proceeded, the greater the signal will be. When the acceptor moiety does not fluoresce and dissipates transfer energy as heat (i.e., quenches), the progress of the amplification reaction may be measured as a decrease in the emissions of the donor.

Figure 8B:
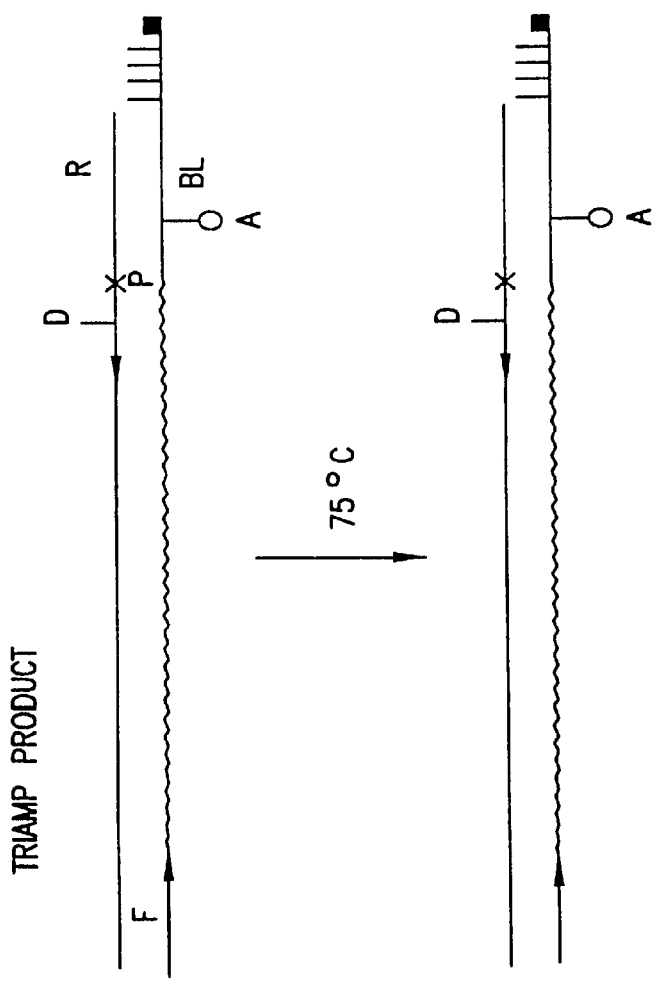

In one embodiment, wherein triamplification is employed (Section 5.4.2), single-strand-specific 3'-5' exonuclease is added to the amplification vessel after the amplification is complete. As shown in FIG. 8, 3'-5' exonuclease treatment hydrolyzes the non-base-paired end of the reverse primer. The 3'-end of the blocker is protected and remains intact.

The interaction of the FRET fluorophores inside the amplified product will not be affected by this treatment for two reasons. First, the 3'-end of the amplified product will be base-paired and thus will not be a good substrate for the exonuclease. Second, the primer that is incorporated into the amplification product is extended on its 3' end and its labeled nucleotide residue will be relatively far from the unprotected 3'-hydroxyl. Therefore, it will take much longer for the nuclease to reach the modified residue. As a result, the only detectable FRET signal will come from the amplified product and will be free of background. Preferably the donor should be on the forward primer, and the acceptor on the blocker, but the converse is also possible.

The use of 3'-5' exonuclease in nucleic acid amplifications using linear primers eliminates the necessity of separating the amplification product from the non-incorporated oligonucleotides after the reaction. In a preferred embodiment, the method of the present invention may be carried out in the vessel in which the amplification reaction proceeds, without opening the vessel in order to allow for separation of amplification product. Polymerase and exonuclease may be mechanically separated during amplification, for example, in a two-chamber reaction tube as shown in FIG. 11A. After amplification, the reaction tube is inverted, as in FIG. 11B, allowing exonuclease to mix with the amplification mixture, resulting in hydrolysis of unreacted labeled primer. This provides for a greatly decreased chance of carryover contamination, and consequently, fewer false positive results in clinical studies. This "closed-tube" format is also readily amenable to automation.

In another embodiment, triamplification or PCR amplification can be performed as described in Sections 5.4.1, 5.4.2 and 6, with the exception that thermostable DNA polymerase is present as a combination of two enzymes, with and without 3'-5' exonuclease activity. The ratio of polymerase to exonuclease can be adjusted such that polymerization predominates during the amplification cycles. After amplification, when the cycling is over, single-stranded template will no longer be generated to which primers can bind. Hence there will be no template/primer complex for DNA polymerase to bind for dNTP incorporation. Therefore, the DNA polymerase will have a chance to bind and digest the unreacted primers using its 3'-5' exonuclease activity.

5.3.2. USE OF TEMPERATURE ELEVATION IN AMPLIFICATION REACTIONS

Background fluorescence of an amplification reaction such as a triamplification reaction can be decreased greatly by increasing the temperature of the amplification vessel, as an alternative to using exonuclease. During detection, the temperature in the vessel is raised sufficiently high enough to cause the short duplex formed between the unused blocker and the reverse primer to dissociate, preventing FRET. At the same time, the much longer amplification product remains double-stranded and generates a FRET signal (see, e.g., Example 5). In this embodiment, detection will preferably be carried out using a thermostable-cuvette or plate-reader fluorimeter. This embodiment also has the advantage that separation of the amplification product from unused primer is not required. Thus, as in the previous embodiment that uses exonuclease treatment, amplification products may be detected directly, without opening the reaction vessel.

5.4. METHODS FOR DETECTION OF AMPLIFICATION PRODUCTS USING LINEAR PRIMERS

Linear primers of the invention can be employed, for example, in PCR, NASBA, strand displacement, and triamplification. When using linear primers in closed-tube format amplification reactions, 3'-5' exonuclease treatment and/or temperature elevation (Section 5.3) is preferably used to distinguish the primers from the amplification product.

5.4.1. METHODS OF USE OF LINEAR PRIMERS IN POLYMERASE CHAIN REACTION (PCR)

In one embodiment, the primers of the invention are used to prime a polymerase chain reaction (PCR) (an example of which is shown in FIG. 25), thereby becoming incorporated into the amplification product. A donor fluorophore moiety is attached to the primer, and an acceptor moiety that is either a fluorophore or a quencher is attached a short distance away from the donor (30 nucleotides or less) on the same primer.

After the PCR amplification is complete, 3'-5' exonuclease is introduced into the reaction vessel. The exonuclease cleaves all free primer in the reaction vessel. The reaction mixture is then exposed to light of the appropriate wavelength to excite the donor moiety.

When the acceptor moiety is a fluorophore, the only acceptor label that will emit light is that which remains on uncleaved primer that has been incorporated into the amplified product, thus giving an indication of the extent of amplification. The further amplification has proceeded, the greater the signal from the acceptor moiety will be. When the acceptor moiety does not fluoresce and dissipates transfer energy as heat (i.e., it quenches), the progress of the reaction may be measured as a decrease in the emissions of the donor.

5.4.1.1. METHODS OF USE OF LINEAR PRIMERS IN ALLELE-SPECIFIC PCR (ASP)

In another embodiment, linear primers of the invention are used to prime an allele-specific PCR (ASP) as is described in Section 5.2.1.1 supra. In this embodiment, one or both amplification primers can be linear primers.

5.4.2. METHODS OF USE OF LINEAR OLIGONUCLEOTIDES IN TRIAMPLIFICATION

In one embodiment, a pair of linear primers of the invention is used in triamplification (the general steps for which are described in Section 5.2.2.1).

As applied to the gap version of triamplification, and in an embodiment wherein the donor and acceptor moieties, respectively, of a MET pair are situated on separate linear oligonucleotides, either the forward or the reverse extending primer, and the third or blocking oligonucleotide are labeled. However, one of the pair of MET donor-acceptor labels should be on the blocker, and the other should be on a single-stranded 3' end of the primer that is complementary to the blocker (see, e.g., FIGS. 7 and 8). In such a specific embodiment employing a FRET pair consisting of donor and acceptor fluorophores, the primer and blocking oligonucleotide are labeled with the donor and acceptor fluorophores, respectively, such that when both oligonucleotides are in close proximity (hybridized to each other) and the donor label is stimulated, FRET occurs and a fluorescence signal is produced at the emission wavelength of the acceptor fluorophore. (Alternatively, the acceptor moiety may be a quencher.) In a specific embodiment, the primer that is not complementary to the blocker is unlabeled with either the donor or acceptor moieties of the FRET pair, or alternatively, is labeled with both moieties (see paragraph below). After triamplification, exonuclease treatment and/or temperature elevation are preferably used to allow detection of amplified product without the need for separation of unincorporated primers (see Sections 5.3.1 and 5.3.2).

In another embodiment using triamplification wherein it is desired to use linear oligonucleotide(s) doubly labeled with both acceptor and donor moieties of a MET pair, and wherein exonuclease treatment (but not temperature elevation) is to be used after the triamplification reaction so as to avoid the need for separation of unincorporated labeled oligonucleotides, the forward and/or the reverse primer can each be labeled with both the donor and acceptor moieties of the FRET pair (within FRET distance of each other) if one of the moieties is on a 3' single stranded extension.

5.5. METHODS OF USE OF HAIRPIN OR LINEAR PRIMERS IN MULTIPLEX ASSAYS

Through the use of several specific sets of primers, amplification of several nucleic acid targets can be performed in the same reaction mixture. In a preferred embodiment, one or both primers for each target can be hairpin primers labeled with a fluorescent moiety and a quenching moiety that can perform FRET. Amplification of several nucleic acid targets requires that a different fluorescent acceptor moiety, with a different emission wavelength, be used to label each set of primers.

During detection and analysis after an amplification, the reaction mixture is illuminated and read at each of the specific wavelengths characteristic for each of the sets of primers used in the reaction. It can thus be determined which specific target DNAs in the mixture were amplified and labeled. In a specific embodiment, two or more primer pairs for amplification of different respective target sequences are used.

5.6. ASSAYING THE METHYLATION STATUS OF DNA USING AMPLIFICATION REACTIONS OF THE INVENTION

Methylation of cytosine located 5' to guanosine is known to have profound effects on the expression of several eukaryotic genes (Bird, 1992, Cell 70: 5–8). In normal cells, methylation occurs predominantly in CG-poor regions, while CG-rich areas, called "CpG-islands," remain unmethylated. The exception is extensive methylation of CpG islands associated with transcriptional inactivation of regulatory regions of imprinted genes (Li et al., 1993, Nature 366: 362–365) and with entire genes on the inactive X-chromosome of females (Pfeifer et al., 1989, Science 246: 810–813).

Aberrant methylation of normally unmethylated CpG islands has been documented as a relatively frequent event in immortalized and transformed cells (Antequera et al., 1990, Cell 62: 503–514), and has been associated with transcriptional inactivation of defined tumor suppressor genes in human cancers (Herman et al., 1996, Proc.Natl. Acad. Sci., USA, 93: 9821–9826). Sensitive detection of CpG island methylation has the potential to define tumor suppressor gene function and provides a new strategy for early tumor detection.

Methylation specific PCR is a sensitive detection method for abnormal gene methylation in small DNA samples (Herman et al., 1996, Proc. Natl. Acad. Sci., USA, 93: 9821–9826). Methylation specific PCR employs an initial bisulfite reaction to modify DNA. All unmethylated cytosines are dominated in a bisulfite reaction and converted to uracils. Methylated cytosines are unaffected by the bisulfite reaction. Consequently, a sequence of DNA that is methylated will differ in sequence, after bisulfite treatment, from an identical sequence that is unmethylated. Hence, different sets of primers may be designed to specifically amplify each of those sequences (e.g, a pair of primers to amplify unmethylated, bisulfite treated DNA will have one or more G residues replaced by an A residue (to be complementary to nucleotides that were formerly unmethylated cytosines), and one or more C residues replaced by a T residue, respectively, for the two primers of the pair, relative to the primer pair for the methylated or untreated DNA).

As in any other PCR-based technique, this method is very sensitive. Any carry-over contamination from sources external to the PCR will cause false positive results. The use of the MET-labeled hairpin primers of the present invention eliminates the risk of carry-over contamination, since the reaction may be performed and monitored (in real time, if necessary) in a closed-tube format.

The use of bisulfite treatment in the methods of the invention is not limited to those methods employing PCR; other amplification methods may alternatively be employed. The invention thus provides a method of assaying the methylation status of DNA using an amplification reaction of the invention, with hairpin or linear primers. The method comprises: prior to conducting an amplification reaction, contacting a sample containing purified nucleic acids with an amount of bisulfite sufficient to convert unmethylated cytosines in the sample to uracil; and conducting the amplification reaction in the presence of a primer pair specific for preselected target sequences. Pairs of primers, used in separate reaction vessels, are preferably specific for bisulfite-treated methylated, bisulfite-treated unmethylated, and nonbisulfite-treated (wild type) nucleic acids, respectively. Conclusions about the methylation status of the nucleic acids in the sample can be drawn depending on which primer pair(s) give amplification product. In a preferred embodiment, the amplification reaction is PCR sing one or more hairpin primers.

5.7. KITS FOR THE AMPLIFICATION AND DETECTION OF SELECTED TARGET DNA SEQUENCES

An additional aspect of the present invention relates to kits for the detection or measurement of nucleic acid amplification products. In specific embodiments, the kits comprise one or more primer oligonucleotides of the invention, such as a hairpin primer, including but not limited to a universal hairpin primer, and/or linear primers, in one or more containers. The kit can further comprise additional components for carrying out the amplification reactions of the invention. Where the target nucleic acid sequence being amplified is one implicated in disease or disorder, the kits can be used for diagnosis or prognosis. In a specific embodiment, a kit is provided that comprises, in one or more containers, forward and reverse primers of the invention for carrying out amplification, and optionally, a DNA polymerase or two DNA polymerases respectively with and without exonuclease activity. A kit for triamplification can further comprise, in one or more containers, a blocking oligonucleotide, and optionally DNA ligase.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers. Multiplex kits are also provided, containing more than one pair of amplification (forward and reverse) primers, wherein the signal being detected from each amplified product is of a different wavelength, e.g., wherein the donor moiety of each primer pair fluoresces at a different wavelength. Such multiplex kits contain at least two such pairs of primers.

In a specific embodiment, a kit comprises, in one or more containers, a pair of primers preferably in the range of 10–100 or 10–80 nucleotides, and more preferably, in the range of 20–40 nucleotides, that are capable of priming amplification [e.g., by polymerase chain reaction (see e.g., Innis et al., 1990, PCR Protocols, Academic Press, Inc., San Diego, Calif.), for example, competitive PCR and competitive reverse-transcriptase PCR (Clementi et al., 1994, Genet. Anal. Tech. Appl. 11(1):1–6; Siebert et al., 1992, Nature 359:557–558); triamplification, NASBA, strand displacement, or other methods known in the art, under appropriate reaction conditions, of at least a portion of a selected target nucleic acid.

In another embodiment, a kit for the detection of a selected target DNA target sequence comprises in one or more containers (a) PCR primers, one or both of which are hairpin primers labeled with fluorescent and quenching moieties that can perform MET; and optionally: (b) a control DNA target sequence; (c) an optimized buffer for amplification; (d) appropriate enzymes for the method of amplification contemplated, e.g., a DNA polymerase for PCR or triamplification or SDA, a reverse transcriptase for NASBA; (d) a set of directions for carrying out amplification, e.g., describing the optimal conditions, e.g., temperature, number of cycles for amplification. Optionally, the kit provides (e) means for stimulating and detecting fluorescent light emissions, e.g., a fluorescence plate reader or a combination thermocycler-plate-reader to perform the analysis.

In yet another embodiment, a kit for triamplification is provided. The kit comprises forward and reverse extending primers, and a blocking oligonucleotide. Either the forward or reverse primer is labeled with one moiety of a pair of MET moieties, and the blocking oligonucleotide is labeled with the other MET moiety of the pair. One embodiment of such a kit comprises, in one or more containers: (a) a first oligonucleotide; (b) a second oligonucleotide, wherein said first and second oligonucleotides are linear primers for use in a triamplification reaction; (c) a third oligonucleotide that is a blocking oligonucleotide that comprises a sequence complementary and hybridizable to a sequence of said first oligonucleotide, said first and third oligonucleotides being labeled with a first and second moiety, respectively, that are members of a molecular energy transfer pair consisting of a donor moiety and an acceptor moiety, such that when said first and third oligonucleotides are hybridized to each other and the donor moiety is excited and emits energy, the acceptor moiety absorbs energy emitted by the donor moiety; and (d) in a separate container, a nucleic acid ligase.

Another embodiment of a kit comprises in a container a universal hairpin primer, optionally also comprising a second container containing cyanogen bromide or a nucleic acid ligase (e.g., DNA ligase, for example, T4 DNA ligase).

A kit for carrying out a reaction such as that shown in FIG. 5 comprises in one or more containers: (a) a first oligonucleotide primer; (b) a second oligonucleotide primer, wherein the first and second oligonucleotide primers are forward and reverse primers for DNA synthesis in an amplification reaction to amplify a nucleic acid sequence, and wherein said second oligonucleotide primer comprises (i) a 5' sequence that is not complementary to a preselected target sequence in said nucleic acid sequence, and (ii) a 3' sequence that is complementary to said preselected target sequence; and (c) a third oligonucleotide primer that comprises in 5' to 3' order (i) a first nucleotide sequence of 6–30 nucleotides, wherein a nucleotide within said first nucleotide sequence is labeled with a first moiety selected from the group consisting of a donor moiety and an acceptor moiety of a molecular energy transfer pair, wherein the donor moiety emits energy of one or more particular wavelengths when excited, and the acceptor moiety absorbs energy at one or more particular wavelengths emitted by the donor moiety; (ii) a second, single-stranded nucleotide sequence of 3–20 nucleotides; (iii) a third nucleotide sequence of 6–30 nucleotides, wherein a nucleotide within said third nucleotide sequence is labeled with a second moiety selected from the group consisting of said donor moiety and said acceptor moiety, and said second moiety is the member of said group not labeling said first nucleotide sequence, wherein said third nucleotide sequence is sufficiently complementary in reverse order to said first nucleotide sequence for a duplex to form between said first nucleotide sequence and said third nucleotide sequence such that said first moiety and second moiety are in sufficient proximity such that, when the donor moiety is excited and emits energy, the acceptor moiety absorbs energy emitted by the donor moiety; (iv) at the 3' end of said third oligonucleotide primer, a fourth nucleotide sequence of 10–25 nucleotides that comprises at its 3' end a sequence identical to said 5' sequence of said second oligonucleotide primer. Where such kit is used for triamplification, a blocking oligonucleotide can also provided.

Another kit of the invention comprises in one or more containers: (a) a first oligonucleotide; (b) a second oligonucleotide, said first and second oligonucleotide being hybridizable to each other; said first oligonucleotide being labeled with a donor moiety said second oligonucleotide being labeled with an acceptor moiety, said donor and acceptor moieties being a molecular energy transfer pain, wherein the donor moiety emits energy of one or more particular wavelengths when excited, and the acceptor moiety absorbs energy at one or more particular wavelengths emitted by the donor moiety; and (c) in a separate container, a nucleic acid ligase.

6. EXAMPLES: GENERAL EXPERIMENTAL METHODS

The following experimental methods were used for all of the experiments detailed below in the Examples, Sections 7–13, except as otherwise noted. In all of the Examples, the experiments were carried out using either triamplification or PCR.

6.1. OLIGONUCLEOTIDE SEQUENCES: SYNTHESIS AND MODIFICATION

Three oligodeoxynucleotides complementary to segments of human prostate specific antigen (PSA) DNA were synthesized (FIG. 12). Reverse primer contained a 2'-O-methyl moiety at a position complementary to the 5'-end of the blocker. This modification was essential for prevention of strand displacement during the amplification process (see Section 5.2.2.1) The blocker had biotin on its 3' end, in order to protect it from 3'-5' exonuclease hydrolysis and from undesirable extension during amplification. During the synthesis of blocker and forward primer, the primary amino group was incorporated on the modified T-base (Amino-Modifier C6 dT) as described by Ju et al. (1995, Proc. Natl. Acad. Sci. USA 92:4347–4351). These modifications were used for subsequent incorporation of fluorescent dyes into designated positions of the oligonucleotides. Synthesized oligonucleotides were desalted and FAM (as a donor) and rhodiamine (as an acceptor) were attached to a modified thymidine residue of the reverse primer and blocker, respectively, by the method published by Ju et al. (1995, Proc. Natl. Acad. Sci. USA 92:4347–4351). Labeled oligonucleotides were purified on a 15% denaturing polyacrylamide gel.

The absorption spectra of the primers were measured on a Hewlett Packard 8452A diode array spectrophotometer and fluorescence emission spectra were taken on a Shimadzu RF-5000 spectrofluorophotometer.

6.2. AMPLIFICATION OF PROSTATE SPECIFIC ANTIGEN (PSA) TARGET DNA

Triamplification was performed in 120 $\mu$l of 20 mM tris-HCl (pH 8.5), 10 mM $(NH_4)_2SO_4$, 0.1 mg/ml BSA, 2 mM NAD 0.1% Triton X100, 2 mM $MgCl_2$, 200 $\mu$M each dNTP, $10^{-11}$M template, 250 nM forward primer, 250 nM reverse primer labeled with FAM, 500 nM blocker labeled with Rhod, 6 units of Pfu-exo$^-$ DNA polymerase (polymerase without 3'-5' exonuclease activity; Stratagene)

and 30 units of Amp DNA ligase (Epicentre Tech). PCR amplification was performed using the same conditions, except that blocker and ligase omitted from the PCR reaction mixture. Thermal cycling was performed using denaturation for 5 min at 94° C., followed by 35 cycles of 30 sec at 95° C. and 2 min 60° C. The PCR was completed with a final 6 min extension at 60° C.

As a first control, a similar triamplification reaction was performed in the absence of DNA template. As a second control, the reaction mixture was not incubated in the thermocycler.

6.3. 3'-5' EXONUCLEASE TREATMENT

Four units of T4 DNA polymerase that had 3'-5' exonuclease activity were added to the amplified DNA or control probe in 120 µl of the amplification buffer and incubated at 37° C. for 15 min, unless otherwise indicated.

6.4. ENERGY TRANSFER MEASUREMENTS

Energy transfer measurements were made on a Shimadzu RF-5000 spectrofluorophotometer. The excitation wavelength was 488 nm and the emission spectra were taken between 500 and 650 nm.

7. EXAMPLE 1: DNA POLYMERASE COPIES A DNA TEMPLATE WITH RHODAMINE MODIFICATION

This experiment (FIG. 13A) was conducted to determine the effects of modification of a DNA template with rhodamine on the activity of DNA polymerase. If rhodamine labeling of the reverse primer were to block the incorporation of dNTP, elongation of the forward primer would stop at the base opposite the modification. In this case, the two strands of amplified product would be of different sizes: the one with incorporated forward primer would be shorter.

A PCR amplification (FIG. 13A) was performed using the conditions for triamplification described in Section 6, but without using blocker. As illustrated in FIG. 13B, the strands synthesized in the presence of modified and unmodified reverse primer were of the same size, indicating that rhodamine-labeling did not interfere with amplification.

The effects of rhodamine labeling on the yield of the amplification reaction were also estimated. PCR amplification was performed and as a control, unmodified reverse primer was used. As shown on the agarose gel of FIG. 13C, the amount of product was similar when rhodamine-reverse primer or non-modified reverse primer was present.

These results lead to the conclusion that the modifications in the DNA template do not affect the elongation reaction catalyzed by DNA polymerase.

8. EXAMPLE 2: MODIFICATION OF A REVERSE PRIMER DOES NOT AFFECT THE REACTION CATALYZED BY DNA LIGASE

Since triamplification uses thermostable DNA-ligase for amplification, it was important to determine whether the modification of primers affects ligation efficiency. Triamplification was performed as described in Section 6 with rhodamine-labeled reverse primer. As shown in FIG. 14A, the blocker had four nucleotides plus biotin on its 3'-end that extended it beyond the reverse primer sequence.

In cases in which the extended forward primer was ligated to the blocker, the resulting strand would be expected to be approximately 4 nucleotides longer than the opposite strand, which would have incorporated the extended reverse primer. If no ligation took place and instead the blocker was displaced, then both strands would be expected to be of the same length. By using [$^{32}$P]-labeled forward or reverse primer in parallel experiments, the efficiency of ligation was estimated.

As shown in FIG. 14B, most of the product with labeled forward primer was longer than the strand with labeled reverse primer, indicating that there was no significant effect of modification on the ligation reaction.

9. EXAMPLE 3: EXONUCLEASE CAN REMOVE A NUCLEOTIDE RESIDUE LABELED WITH RHODAMINE

Exonuclease hydrolysis of a [$^{32}$P]-labeled reverse primer labeled with rhodamine (FIG. 15A) was performed in an amplification reaction mixture in a PCR amplification using the methods described in Section 6. T4 DNA polymerase with 3'-5' exonuclease activity was used. Products of hydrolysis were analyzed on a 15% denaturing polyacrylamide gel. The results presented in FIG. 15B demonstrate nearly quantitative hydrolysis of the modified oligonucleotide after 5 minutes. Similar results were obtained when a [$^{32}$P]-labeled reverse primer labeled with rhodamine was in complex with blocker.

10. EXAMPLE 4: DETECTION OF AMPLIFICATION PRODUCT BY ENERGY TRANSFER AFTER NUCLEASE TREATMENT

To detect the triamplification product blip FRET between the reverse primer labeled with FAM and the blocker labeled with rhodamine, the triamplification and the subsequent exonuclease treatment were performed as described in Section 6. As a control, the triamplification reaction was also performed in the absence of DNA template.

Emission spectra are presented in FIG. 16. The FRET signal at 605 nm was emitted by the double-stranded amplification product (FIG. 16, Spectrum 1) whereas no FRET signal was emitted from the control reaction run without DNA template (FIG. 16, Spectrum 2).

11. EXAMPLE 5: DETECTION OF AMPLIFICATION PRODUCT BASED ON DIFFERENT THERMOSTABILITY OF AMPLIFIED PRODUCT AND BLOCKER/REVERSE PRIMER COMPLEX

The goal of this experiment was to determine whether a specific temperature could be found at which free blocker and reverse primer were no longer in duplex, so that no energy transfer could occur between them. At this temperature, however, the double-stranded triamplification product would still remain in duplex, so that the primers incorporated into it would generate a FRET signal.

Triamplification was performed as described in Section 6. A control reaction was run in the absence of DNA template. After amplification, reaction mixtures were heated to 75° C. and emission spectra were taken. The results indicate that at this temperature, there was no signal from non-amplified primers (FIGS. 17A–B). However, emission of rhodamine at 605 nm (i.e., a FRET signal) from the amplified product could be clearly detected.

12. EXAMPLE 6: CLOSED-TUBE FORMAT USING HAIRPIN PRIMERS FOR AMPLIFICATION AND DETECTION OF DNA BASED ON ENERGY TRANSFER

12.1. SUMMARY

A new method for the direct detection of PCR-amplified DNA in a closed system is described. The method is based on the incorporation of fluorescence resonance energy transfer-labeled primers into the amplification product. The PCR primers contain hairpin structures on their 5' ends with donor and acceptor moieties located in close proximity on the hairpin stem. The primers are designed in such a way that a fluorescent signal is generated only when the primers are incorporated into an amplification product. A signal to background ratio of 35:1 was obtained using the hairpin primers labeled with FAM as a donor and DABCYL as a quencher. The modified hairpin primers do not interfere with the activity of DNA polymerase, and both thermostable Pfu and Taq polymerase can be used. This method was applied to the detection of cDNA for prostate specific antigen. The results demonstrate that the fluorescent intensity of the amplified product correlates with the amount of incorporated primers, and as little as ten molecules of the initial template can be detected. This technology eliminates the risk of carry-over contamination, simplifies the amplification assay, and opens up new possibilities for the real-time quantification of the amplified DNA over an extremely wide dynamic range.

12.2. INTRODUCTION

Polymerase chain reaction (PCR) and other nucleic acid amplification techniques provide a tool for the geometric amplification of minute amounts of initial target sequences (reviewed in Mullis and Faloona, 1987, Methods in Enzymology, 155: 335–350; Landegren, 1993, Trends Genet. 9: 199–204). The extreme sensitivity of DNA/RNA amplification methods has encouraged the development of diagnostics for the early detection of cancer and infectious agents. However, drawbacks to the clinical use of nucleic acid amplification include the possibility of false-positive results due to carry-over contamination, and false-negative results caused by unsuccessful reactions and/or nonstandardized reaction conditions (Orrego, 1990, in Innis et al. (eds.), PCR Protocols, A guide to methods and applications, Academic Press, San Diego, Calif., pp. 447–454).

A major source of carry-over contamination are amplification products from previous amplification reactions. Due to the extreme sensitivity of PCR, even minimal contamination can generate a false positive result, and accordingly, several approaches have been devised to deal with this problem. These include incorporation of dUTP with subsequent treatment with uracil N-glycosylase (Longo et al., 1990, Gene 93: 125–128), incorporation of ribonucleotides into the PCR primers followed by base treatment (Walder et al., 1993, Nucleic Acids Res. 21: 4339–4343) or the use of isopsoralen derivatives which undergo a cycloaddition reaction with thymidine residues upon exposure to UV light (Cimino et al., 1991, Nucleic Acids Res., 19: 88–107). However, a simpler and more certain solution to the problem would be a closed system, where both the amplification reaction and the detection step take place in the same vessel, so that the reaction tube is never opened after amplification. In addition, the "closed tube" format significantly simplifies the detection process, eliminating the need for post-amplification analysis by such methods as gel electrophoresis or dot blot analysis.

The method described infra is designed to measure directly amplified DNA by incorporation of labeled oligonucleotide primers into the reaction product. The conformational transitions that the primers undergo serve as switches for energy transfer between two labels. In this method, the donor and acceptor (quencher) moieties are both attached to a hairpin structure on the 5' end of the amplification primer. The primers are designed in such a way that the fluorescent signal is generated only when the labeled oligonucleotides are incorporated into the double-stranded amplification product. This highly sensitive method may be used to obtain quantitative or qualitative results. Applications for this system to the detection of a specific DNA sequence include, in addition to PCR, triamplification, nucleic acid sequence-based amplification (NASBA), and strand displacement amplification.

12.3. MATERIALS AND METHODS

Oligonucleotide primers

The following oligodeoxynucleotides complementary to the 172 bp segment of human prostate specific antigen (PSA) cDNA were chemically synthesized: 5'-CCCTCAGAAGGTGACCAAGTTCAT (SEQ ID NO:11), as an upstream primer, and 5'-GGTGTACAGGGAAGGCCTTTCGGGAC (SEQ ID NO:12), as a downstream primer. The structures of the upstream hairpin primers with energy transfer labels are shown in FIGS. 24A–G. FAM was incorporated into the 5' end of hairpin primers by using FAM phosphoramidite in the last step of the chemical synthesis. A modified T-base was introduced into a designated position by the use of Amino-Modifier C6 dT (Glen Research), and the DABCYL was attached to the primary amino group as described by Ju et al. (1995, Proc. Natl. Acad. Sci. USA, 92: 4347–4351). Labeled oligonucleotides were purified by HPLC.

Preparation of PSA cDNA

The human PSA-expressing LNCaP cell line (American Type Culture Collection) was used in the experiments. LNCaP cells were diluted with lymphocytes isolated from whole blood at ratios ranging from 1 LNCaP cell to $10^2$ lymphocytes to 1 LNCaP cell to $10^6$ lymphocytes. Messenger RNA was isolated using the Dynal purification kit. cDNA was synthesized from the isolated mRNA using reverse transcriptase (Appligene) and oligodT$_{12-18}$ primers (Pharmacia) according to the recommended protocol.

PCR conditions

Amplification of the PSA cDNA was performed in 100 $\mu$l of 20 mM Tris-HCl (pH 8.5), 50 mM KCl, 2 mM MgCl$_2$, 200 $\mu$M each dNTP, 500 nM each of the upstream and the downstream primers, and 5 units of the Pfu$^{exo-}$ DNA polymerase (which lacks 3'-5' exonuclease activity; Stratagene). Thermal cycling was performed with a 5 min denaturation at 94° C., followed by 20–40 cycles of 30 sec at 95° C., 45 sec at 60° C. and 1.5 min at 72° C., and completed with a final 5 min extension at 72° C.

The PCR product was purified using QIAquick Spin PCR Purification Kit (Qiagen) and cloned into pUC19 plasmid. MDE™ gels (FMC BioProducts) were used for the gel-based detection of the PCR products. Electrophoresis in a 6% polyacrylamide gel with 7M urea, and subsequent quantification on a PhosphorImager-SP (Molecular Dynamics) was used to estimate the amount of primer incorporated into the amplification product.

Fluorescence detection

A Shimadzu RF-5000 spectrofluorophotometer was used to measure the fluorescence spectra of the individual samples. The 100 $\mu$l reaction mixture was diluted to 500 $\mu$l with 20 mM Tris-HCl, pH 8.5, 50 mM NaCl, and 2 mM MgCl$_2$, and placed into a 10×3 cuvette (NSG Precision Cells, Inc.) at room-temperature. For the FAM/DABCYL (4-(4'-dimethylaminophenylazo) benzoic acid) FRET pair, a 488 nm excitation wavelength was used and a spectrum was taken between 500 and 650 nm. The fluorescent PCR product was also visualized by placing the tube directly against a UV transilluminator image analysis system (Appligene), and photographed with a mounted camera using a D540/40 filter (Chroma Technology).

12.4. RESULTS
Experimental design of PCR with hairpin primers

In this method, a hairpin structure is present on the 5' end of one (or both) of the PCR primers (FIG. 1). The sequence of the hairpin stem and loop may be partially complementary to the target DNA sequence, but this is not necessary. There are two moieties attached to the stem sequence of the hairpin: a quencher on the 5' end of the hairpin and a fluorophore on the opposite side of the hairpin stem. The positions of the fluorophore and the quencher may be switched, depending on the availability of the commercial precursors of these moieties. DABCYL is a non-fluorescent chromophore whose absorption spectrum overlaps with the emission spectrum of FAM. When stimulated by light of peak wavelength of 488 nm, FAM emits fluorescence of peak wavelength 516 nm. However, when DABCYL is located sufficiently close to the donor fluorophore, the energy can be transferred to DABCYL and dissipated as heat. Therefore, when the modified primer is in a "closed" configuration (hairpin), the FAM and DABCYL are in close proximity, and the emission of the fluorescein is quenched by DABCYL.

During the first cycle of PCR (FIG. 2), the primers are extended and become templates during the second cycle. Since the hairpin structures are very stable (Varani, 1995, Annu. Rev. Biophys. Biomol. Struct., 24: 379–404), the stems are unlikely to be melted during the annealing step of the PCR on every target molecule. In this case, when the DNA polymerase lacking 5'-3' exonuclease activity reaches the 5' end of the hairpin stem, it will displace it and copy the sequence. Thus, the hairpin primer will be linearized by incorporation into the double-stranded helical structure during PCR, the donor and acceptor will be about 20 nucleotides (~70 Å) apart, resulting in no significant energy transfer between them (Selvin, 1995, Methods Enzymol., 246: 300–334), and the fluorescence from the FAM will be markedly enhanced.

Sequence and spectroscopic properties of the hairpin primer

The structure of the hairpin primer for the amplification of cDNA for prostate specific antigen (PSA) is shown in FIG. 18A (SEQ ID NO:10). The primer consists of a 12 nucleotide long single-stranded priming sequence, a 7 bp stem, and a 6 nucleotide loop. The fluorescent moiety (FAM) is located on the 5' end of the primer and a quencher (DABCYL) is across from FAM on the opposite strand of the stem sequence. FIG. 18B presents the emission spectra of the FAM labeled hairpin primer before and after the incorporation of DABCYL. With no quencher present, FAM that is excited at a wavelength of 488 nm emits a peak wavelength of 516 nm. When the same oligonucleotide is also labeled with DABCYL, the fluorescence energy is transferred to the quencher and a much lower peak is detected at 516 nm. The residual fluorescence of the FAM/DABCYL-labeled oligonucleotide is partially caused by the presence of small quantities of oligonucleotides labeled with FAM alone. Therefore an extensive HPLC purification of the labeled oligonucleotides was very important for the low background in subsequent experiments.

Similar results were obtained with rhodamine as a quencher (data not presented). As a quencher, however, DABCYL has an advantage of being a non-fluorescent chromophore: it absorbs the energy of the fluorescein without emitting light itself. As a result, the emission of the fluorescein may be detected more precisely, without interference from the emission of the acceptor.

Use of hairpin-oligonucleotides as PCR primers

PCR of the fragment of PSA cDNA was performed using thermostable pfu$^{exo-}$ DNA polymerase. Total cDNA from human PSA-expressing LNCaP cells mixed with lymphocytes was used for amplification. The preliminary experiments using ethidium bromide-stained gels for the assay showed that one PSA cell per $10^5$ lymphocytes could be detected. For quantification purposes, the PCR product was cloned and used to compare the efficiency of amplification in the presence of the hairpin primer with that for the control primer, which lacks the hairpin structure and modifications. FIG. 19 shows that the amount of amplified product was similar for the control primer, the hairpin primer containing FAM alone and the hairpin primer labeled with the FAM/DABCYL FRET pair.

A crucial requirement for the method is the linearization of the hairpin primer during amplification. Therefore DNA polymerase must be able to synthesize the strand complementary to the hairpin primer all the way through the hairpin to its 5' end. The following experiment was conducted to determine whether modifications of the structure of the hairpin primer affect the subsequent synthesis of the full-length PCR product. PCR amplification of PSA cDNA was performed with two primers: an upstream FAM/DABCYL-labeled hairpin primer and a downstream primer labeled with $^{32}$P on its 5' end (FIG. 20A). An upstream primer without the hairpin structure was used as a control.

If the structure and/or the modifications of the hairpin primer creates an obstacle for DNA polymerase, this primer will not be copied all the way to its 5' end, and the [$^{32}$P]-labeled strand will be shorter than the corresponding strand synthesized in the presence of the control primer.

To estimate the length of the individual strands, denaturing gel electrophoresis was performed. As illustrated by the results in FIG. 20B, the [$^{32}$P]-labeled strand that was synthesized in the presence of the hairpin primer was longer than the corresponding strand made with the control primer, indicating that DNA polymerase was able to read through the hairpin structure and synthesize a full-length product.

Another important aspect of this method is the thermostability of the hairpin primer. If the oligonucleotide phosphodiester bonds or the linker arms through which donor and/or acceptor are tethered to the oligonucleotide are cleaved as a result of high temperature, the quencher will be separated from the fluorophore and the background will increase. Indeed, when 50 pmoles of the hairpin primer was incubated in a 100 μl reaction for 40 cycles, the background signal increased from 3.8 units to 12 units of fluorescence intensity. However, the observed background was still very low: it comprised only 6% of the fluorescence emitted by 50 pmoles of fluorescein-labeled oligonucleotides (200 units), which was the amount used in the assays.

Monitoring of PCR with hairpin primers

To demonstrate that the fluorescence of the PCR product could be used to monitor the reaction, total cDNA from the mixture of 1 human PSA-expressing LNCaP cell per $10^4$ lymphocytes was amplified with the FAM/DABCYL-labeled hairpin primer. After different numbers of cycles, the fluorescence intensity of the amplified product was determined using a spectrofluorophotometer (FIG. 21A). The results show that after only 20 cycles, the fluorescence intensity increased five times compared to the non-amplified reaction mixture, and a thirty-five-fold increase was detected after 40 cycles of amplification. The same samples were also analyzed by denaturing gel electrophoresis with subsequent quantification on the PhosphorImager to determine the fraction of [$^{32}$P]-labeled primers incorporated into the product. The results in FIG. 21B demonstrate that the fluorescence intensity of the reaction mixture correlates with the amount of primers incorporated into the product.

In another experiment, the sensitivity of this method was explored. For quantification purposes, cloned PSA cDNA was used as a template. 40 cycles of PCR were performed with 0, 10, $10^2$, $10^3$, $10^4$, $10^5$, or $10^6$ molecules of cloned PSA cDNA per reaction. The results in FIG. 22 demonstrate that the method is sensitive enough to detect 10 molecules of the initial DNA template with a spectrofluorophotometer. The fluorescent PCR product was also visualized by placing the tube directly on a UV transilluminator equipped with a mounted camera and D540/40 filter. This filter permits the detection of the emission in a narrow wavelength window: between 515 and 560 nm. As shown in FIG. 23, the fluorescence of the PCR reaction performed with $10^4$, $10^5$ and $10^6$ molecules of the initial template could easily be detected by visual inspection of the tubes.

Effect of the structure of labeled hairpin primer on the amplification and detection Several hairpin primers with varying sizes of stem, loop and 3' single-stranded sequences were synthesized to estimate how these parameters might affect the efficiency of the PCR and the signal-to-background ratio. The structures and the relative fluorescent intensities are presented in FIGS. 24A–G. All primers tested had at least an 18-nucleotide sequence complementary to the target, which comprised a 3' single-stranded priming sequence, a 3' stem sequence and part of the loop (highlighted in bold in FIGS. 24A–G).

The length of the 3' single-stranded priming sequence was found to be very important for the efficiency of the hairpin primers in the PCR reaction. Almost no product was detected when the length of the priming sequence was decreased from twelve nucleotides in Structure A to six nucleotides in Structure G (FIG. 24). A possible explanation for this result is that the hairpin structure is the preferred conformation of this oligonucleotide, even at the 60° C. annealing temperature, and that the nucleotides in the stem and loop of the hairpin are not available for hybridization to the target DNA. In this case, the only part of the molecule not involved in the secondary structure is the 3' single-stranded sequence; however, the six nucleotide sequence on the 3' end of Structure G is not long enough to be an efficient PCR primer.

Only minor variations in the amount of product generated were found when the sizes of stem and loop were changed slightly. The PCR was slightly less efficient when the length of the stem was greater than 7 bp. Stabilization of the stem by replacement of an AT-base pair at the 3' end with GC increased the signal-to-background ratio by 10%.

12.5. DISCUSSION

The method for detection of amplification products in a "closed tube" format is an important step towards a PCR-based automated diagnostic system, since it not only reduces the complexity of the reaction, but also eliminates the chances of carry-over contamination and, consequently minimizes the chances of false-positive results. The amplification primer contains a hairpin structure with two labels on its stem that can undergo fluorescence resonance energy transfer. One label is a fluorophore donor and another is a quencher that can absorb energy emitted by the fluorophore. A thirty-five-fold quenching of the fluorescence was observed when the oligonucleotide primers were in the hairpin conformation, so that less than 3% of maximum fluorescence is detected when the primers are not incorporated into the product. The switch from the hairpin to linearized conformation occurs as a result of replication: the 5' end of the stem is displaced by DNA polymerase, a complementary strand is synthesized and the hairpin can no longer be formed. In the incorporated primers, the distance between the fluorophore and the quencher is around 20 base pairs, which is close to 70 Å, the distance at which energy transfer is negligible (Selvin, 1995, Methods Enzymol. 246: 300–334) and so the quantitative emission of the fluorophore can be detected.

The main advantage of this method is the generation of the fluorescent signal by the product itself, rather than by the hybridized probe, as in previous methods (Holland, et al., 1991, Proc. Natl. Acad. Sci. USA, 88: 7276–7280; Lee et al., 1993, Nucleic Acids Res., 21; 3761–3766; Tyagi and Kramer, 1996, Nature Biotechnol., 14: 303–309). This keeps background low and allows the real-time quantification of the amplified DNA over an extremely wide dynamic range. In addition, the detection does not require special buffer or temperature conditions that are necessary for methods involving hybridization. The discrimination between a long double-stranded DNA product and the short hairpin primer is so efficient that the signal-to-background ratio will be the same over a wide temperature range under a variety of reaction conditions.

This method can be applied to many amplification systems in which a single-stranded oligonucleotide is incorporated into the double-stranded product, and is compatible with any thermostable DNA polymerase. The present example used Pfu$^{exo-}$ DNA polymerase, an enzyme without 5'-3' and 3'-5' exonuclease activity. Similar results were obtained with Taq polymerase, which has 5'-3' exonuclease activity (data not shown). 5'-3' exonuclease activity is a part of the excision-repair function of some DNA polymerases, and it will not attack a free primer. However, if the extended hairpin primer still maintains its hairpin conformation when annealed to the template DNA, then DNA polymerase will hydrolyze the 5' end of the hairpin stem, and the 5' nucleotide with the tethered donor or acceptor will be released into the solution. In either case, replication or hydrolysis, the donor fluorophore will be separated from the acceptor, quenching will be eliminated, and the fluorescence signal from the amplification product will be detected, allowing any thermostable DNA polymerase to be used for the proposed amplification/detection method.

The thirty-five-fold signal-to-background ratio presented in this example can probably be increased even further. Published data suggest that when the fluorophore and the quencher are covalently linked to each other, 200-fold quenching may be achieved (Wang et al., 1990, Tetrahedron Lett., 31: 6493–6496). This implies that placing FRET labels in closer proximity to one another on the stem structure will increase the efficiency of quenching. This goal may be achieved by several approaches, such as variation of the linker arms, changing the positions of the labels, or using FRET pairs in which the donor and acceptor have some affinity to each other. Another way to improve the system is to increase the thermostability of the FRET-labeled oligonucleotides to prevent an increase in the background during amplification due to the spontaneous release of the labels into the solution.

The method described presented in this example can be applied to any diagnostic procedure in which the presence of the target nucleic acid is to be detected either qualitatively or quantitatively. It may be applied to the detection of infectious disease agents and microorganism contamination of food or water, as well as to the detection of some forms of cancer. An important step in the development of any application of this method is optimization of the structure of the primers and cycling conditions, since any side product can give a signal. However, optimization is facilitated by the fact that the size and purity of the product can be confirmed by gel electrophoresis, since the DNA amplified with the labeled hairpin primers can be analyzed by any of the traditional methods.

The present example demonstrates the utility of this method for the detection of cDNA of prostate specific antigen. The results show that the specificity and the sensitivity of detection are comparable to that of other amplification-based methods: as few as ten molecules of the initial target can be detected. This method can also be used for a "multiplex" analysis in which several targets are amplified in the same reaction. For this purpose, hairpin primers labeled with different fluorophores can be used. For clinical applications, in which a large number of samples are to be tested, a fluorescence plate reader could be used to read the assay results, either separately or coupled with the PCR machine.

13. EXAMPLE 7: ASSAY FOR THE METHYLATION STATUS OF CpG ISLANDS USING PCR WITH HAIRPIN PRIMERS

13.1. MATERIALS AND METHODS

Genomic DNA was obtained from OH3 (unmethylated P16 DNA) and HN 12 (methylated P16 DNA) cell lines (acquired from Drs. S. B. Baylin and D. Sidransky, The Johns Hopkins Medical Institutions) and treated with bisulfite (Herman et al., 1996, Proc. Natl. Acad. Sci., USA, 93: 9821–9826).

Three sets. of PCR primers (FIG. 26) that amplify respectively bisulfite-treated unmethylated DNA (Uup and Ud (SEQ ID NOS:19 and 20, respectively)), bisulfite-treated methylated DNA (Mup and Md) (SEQ ID NOS:21 and 22, respectively), and the DNA not treated with bisulfite (wild type, WT) (Wup and Wd) (SEQ ID NOS:23 and 24, respectively) were chemically synthesized. One or the two primers in each set had a hairpin structure at its 5' end, labeled with FAM/DABCYL.

PCR was performed in 40 $\mu$l of 10 mM Tris-HCl (pH 8.3), 50 mM KCl, 2 mM MgCl$_2$, 0.25 mM each dNTP, 0.5 $\mu$M each primer, 100 ng of the corresponding DNA template and 1 unit of GoldTaq polymerase (Perkin Elmer). Thermal cycling was performed using denaturation for 12 min at 94° C. (these conditions were also required for the activation of the GoldTaq polymerase), followed by 35 cycles of 45 sec at 95° C., 45 sec at 65° C. and 1 min at 72° C. The PCR was completed with a final 5 min extension at 72° C.

13.2. RESULTS

The reaction products were analyzed as described in Section 6. After PCR amplification, the fluorescence intensities of the reaction mixtures were measured. The fluorescence intensity of the reaction mixture amplified in the presence of DNA template (+) differed significantly from the fluorescence intensity of the reaction mixture amplified in the absence of DNA template (−) (Table 2). For example, when a U-primer set (for amplification of a sequence of U (bisulfite-treated unmethylated) DNA, see Table 2) was used with U DNA, it was amplified and the intensity of signal differed significantly from the intensity of the reaction mixture with no template. Similarly, use of an M-primer set led to amplification of M (bisulfite-treated methylated) DNA, and use of a W-primer set led to amplification of W (wild-type chemically unmodified) DNA.

TABLE 2

The fluorescence intensity (expressed as fluorescence units) in 20 $\mu$l of the reaction mixture after PCR in the presence (+) and in the absence (−) of DNA template. U, unmethylated genomic DNA that underwent chemical modification with bisulfite; M, methylated genomic DNA that underwent chemical modification with bisulfite; W, genomic DNA that did not undergo chemical modification.

| U DNA | | M DNA | | W DNA | |
|---|---|---|---|---|---|
| + | − | + | − | + | − |
| 18 | 6 | 20 | 6 | 23 | 9 |

13.3. CONCLUSION

The results show that MET-labeled hairpin primers may be used in an amplification reaction to detect, reliably and sensitively, methylated or unmethylated DNA.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. An oligonucleotide for use as a primer in detecting a target nucleotide sequence, said oligonucleotide comprising:
   (a) a first nucleotide sequence complementary to a sequence flanking said target sequence;
   (b) a second nucleotide sequence at the 5' end of said first sequence;
   (c) a third nucleotide sequence at the 5' end of said second sequence;
   (d) a fourth nucleotide sequence at the 5' end of said third sequence, said fourth sequence being complementary to said second sequence so as to form a double stranded duplex, and
   (e) means for emitting a detectable signal when the strands of said duplex are separated.

2. The oligonucleotide according to claim 1 wherein said signal emitting means comprises an energy donor moiety and an energy acceptor moiety, each bound to said oligonucleotide and spaced such that said signal is detectable only when the strands of said duplex are separated.

3. The oligonucleotide according to claim 2 wherein said energy donor moiety is a fluorophore and said energy acceptor moiety is a fluorophore quencher.

4. A method for the amplification and detection of a target nucleotide sequence in a sample comprising the steps of:
   (a) providing a pair of primers each complementary to said target nucleotide sequence, at least one member of said primer pair comprising the detecting oligonucleotide of claim 1;
   (b) separating the strands of the nucleic acid containing the target nucleotide sequence;
   (c) annealing said pair of primers to the opposite strands of said separated nucleic acid;
   (d) synthesizing new strands of nucleic acid complementary to the strands of said separated nucleic acid;
   (e) separating said new strands from their complementary strands; and
   (f) repeating steps (c)-(e) wherein the synthesis of new strands separates the duplex strands of said oligonucleotide, thereby causing said detectable signal to be emitted.

5. A kit for use in detecting a target nucleotide sequence comprising:
   (a) first and second oligonucleotide primers at least one of which comprises:
       (i) a 3' nucleotide sequence that is complementary to a sequence flanking said target nucleotide sequence;
       (ii) a 5' nucleotide sequence that is not complementary to a sequence flanking said target sequence; and
   (b) a third oligonucleotide primer comprising:
       (i) a first sequence identical to said 5' sequence;
       (ii) a second sequence at the 5' end of said first sequence;
       (iii) a third nucleotide sequence at the 5' end of said second sequence;
       (iv) a fourth nucleotide sequence at the 5' end of said third sequence, said fourth sequence being complementary to said second sequence so as to form a double stranded duplex, and
       (v) means for emitting a detectable signal when the strands of said duplex are separated.

6. The kit according to claim 5 wherein said 5' nucleotide sequence is not a naturally occurring sequence.

7. The oligonucleotide of claim 2 wherein said energy donor and acceptor moieties are spaced a distance in the range of about 10–40 nucleotides.

8. The oligonucleotide of claim 2 wherein said acceptor moiety is a fluorophore that emits fluorescent light at a wavelength different than that emitted by said donor moiety.

9. The oligonucleotide of claim 1 wherein said target nucleotide sequence is selected from the group consisting of genomic DNA, cDNA, mRNA, and chemically synthesized DNA.

10. The oligonucleotide of claim 1 wherein said target nucleotide sequence is a sequence of an infectious disease agent.

11. The oligonucleotide of claim 1 wherein said target nucleotide sequence is a wild-type human genomic sequence, mutation of which is implicated in the presence of a human disease or disorder.

12. The oligonucleotide of claim 2 wherein said donor moiety is selected from the group consisting of fluorescein, 5-carboxyfluorescein (FAM), rhodamine, 5-(2'-aminoethyl) aminonapthalene-1-sulfonic acid (EDANS), anthranilamide, coumarin, terbium chelate derivatives, and Reactive Red 4; and said acceptor moiety is selected from the group consisting of DABCYL, rhodamine, tetramethyl rhodamine, pyrene butyrate, eosine nitrotyrosine, ethidium, fluorescein, Malachite green, and Texas Red.

13. The oligonucleotide of claim 12 wherein said donor moiety is fluorescein or a derivative thereof, and said acceptor moiety is DABCYL.

14. The oligonucleotide of claim 1 wherein said first or third nucleotide sequence further comprises a restriction endonuclease recognition site.

15. The oligonucleotide of claim 2 wherein said energy donor moiety and said energy acceptor moiety are situated on complementary nucleotides that are opposite each other in said duplex.

16. The oligonucleotide of claim 2 wherein said energy donor moiety and said energy acceptor moiety are situated on opposite strand nucleotides that are five nucleotides apart in said duplex.

17. A kit comprising in one or more containers:
    (a) a first oligonucleotide; and
    (b) a second oligonucleotide, wherein said first and second oligonucleotides are primers for use in a nucleic acid amplification reaction to amplify a preselected target nucleic acid sequence, and at least one of said first and second oligonucleotides is the oligonucleotide of claim 1.

18. The kit of claim 17 which further comprises a blocking oligonucleotide comprising a sequence complementary and hybridizable to a sequence of said first or said second oligonucleotide.

19. The kit of claim 17 which further comprises in one or more containers:
    (c) an optimized buffer for said amplification reaction;
    (d) a control nucleic acid comprising the preselected target sequence; and
    (e) a DNA polymerase.

20. A kit comprising in one or more containers:
    (a) a first oligonucleotide;
    (b) a second oligonucleotide, wherein said first and second oligonucleotides are primers for use in a nucleic acid amplification reaction to amplify a first preselected target nucleic acid sequence, and at least one of said first and second oligonucleotides is the oligonucleotide of claim 3;
    (c) a third oligonucleotide, and
    (d) a fourth oligonucleotide, wherein said third and fourth oligonucleotides are primers for use in said nucleic acid amplification reaction to amplify a second preselected target sequence, and at least one of said third and fourth oligonucleotides is an oligonucleotide of claim 3, and wherein said donor moiety of said first and second oligonucleotide emits fluorescent light of a different wavelength than said donor moiety of said third or fourth oligonucleotide.

21. The kit of claim 17 wherein said amplification reaction is selected from the group consisting of the polymerase chain reaction, strand displacement, triamplification and NASBA.

22. An oligodeoxynucleotide, the sequence of which consists of:
5'-ACCTTCTACCCTCAGAAGGTGACCAAGTTCAT-3' (SEQ ID NO:13), wherein fluorescein or a derivative thereof is attached to the 5' A and DABCYL is attached to the T at nucleotide number 20.

23. An oligodeoxynucleotide, the sequence of which consists:
5'-CACCTTCACCCTCAGAAGGTGACCAAGTTCAT-3' (SEQ ID NO:18), wherein fluorescein or a derivative thereof is attached to the 5' C and DABCYL is attached to the T at nucleotide number 20.

24. The kit of claim 17 wherein said first and second oligonucleotides are oligodeoxynucleotides.

25. A method for detecting or measuring a product of a nucleic acid amplification reaction comprising:
    (a) contacting a sample comprising nucleic acids with at least two oligonucleotide primers, said oligonucleotide primers being adapted for use in said amplification reaction such that said primers are incorporated into an amplified product of said amplification reaction when a preselected target sequence is present in the sample; at least one of said oligonucleotide primers being the oligonucleotide of claim 2;
    (b) conducting the amplification reaction;
    (c) stimulating energy emission from said donor moiety; and
    (d) detecting or measuring energy emitted by said acceptor moiety.

26. The method of claim 25 wherein said donor moiety is a fluorophore.

27. The method of claim 26 wherein said acceptor moiety is a quencher of light emitted by said fluorophore.

28. The method of claim 26 wherein said acceptor moiety emits fluorescent light of a wavelength different from that emitted by said donor moiety.

29. The method of claim 25 wherein said preselected target sequence is selected from the group consisting of genomic DNA, cDNA and mRNA.

30. The method of claim 25 wherein said donor moiety is selected from the group consisting of fluorescein, 5-carboxyfluorescein (FAM), rhodamine, 5-(2'-aminoethyl) aminonapthalene-1-sulfonic acid (EDANS), anthranilamide, coumarin, terbium chelate derivatives, and Reactive Red 4; and said acceptor moiety is selected from the group consisting DABCYL, rhodamine, tetramethyl rhodamine, pyrene butyrate, eosine nitrotyrosine, ethidium, Malachite green, fluorescein and Texas Red.

31. The method of claim 25 wherein said donor moiety is fluorescein or a derivative thereof, and said acceptor moiety is DABCYL.

32. The method of claim 25 wherein the oligonucleotide is a oligodeoxynucleotide.

33. The method of claim 30 wherein said donor moiety and said acceptor moiety are situated on complementary nucleotides that are opposite each other in said duplex.

34. The method of claim 30 wherein said donor moiety and said acceptor moiety are situated on opposite strand nucleotides that are five nucleotides apart in said duplex.

35. The method of claim 30 wherein said oligonucleotide primers comprise a plurality of different oligonucleotides, each oligonucleotide comprising at its 3' end a said sequence complementary to different preselected target sequence whereby said different oligonucleotides are incorporated into different amplified products when each said target sequence is present in said sample, each said oligonucleotide being labeled with a donor moiety that emits light of a different wavelength than that emitted by the other donor moieties, and wherein step (d) of said method comprises detecting or measuring light emitted by each of the donor moieties.

36. The method of claim 30 wherein said amplification reaction is selected from the group consisting of polymerase chain reaction, allele-specific polymerase chain reaction, triamplification, strand displacement, and NASBA.

37. The kit of claim 17 which further comprises in a separate container DNA ligase.

38. The method of claim 25 which further comprises prior to said conducting step, contacting said nucleic acids with an amount of bisulfite sufficient to convert unmethylated cytosines in the sample to uracil.

* * * * *